US009022983B2

(12) United States Patent
Ueda et al.

(10) Patent No.: US 9,022,983 B2
(45) Date of Patent: May 5, 2015

(54) INFUSION PUMP

(75) Inventors: Mitsutaka Ueda, Osaka (JP); Ryoichi Akai, Osaka (JP); Hidenori Takahashi, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 14/122,084

(22) PCT Filed: May 22, 2012

(86) PCT No.: PCT/JP2012/063079
§ 371 (c)(1),
(2), (4) Date: Nov. 25, 2013

(87) PCT Pub. No.: WO2012/161194
PCT Pub. Date: Nov. 29, 2012

(65) Prior Publication Data
US 2014/0100526 A1    Apr. 10, 2014

(30) Foreign Application Priority Data

May 26, 2011  (JP) .................................. 2011-118135
May 26, 2011  (JP) .................................. 2011-118136
May 31, 2011  (JP) .................................. 2011-122190

(51) Int. Cl.
*A61M 5/168*   (2006.01)
*A61M 5/142*   (2006.01)
(Continued)

(52) U.S. Cl.
CPC ........... *A61M 5/16813* (2013.01); *A61M 5/142* (2013.01); *F04B 43/0081* (2013.01); *F04B 43/082* (2013.01); *F04B 43/1223* (2013.01);
(Continued)

(58) Field of Classification Search
USPC ...................... 604/65, 67, 131, 151; 417/476, 417/477.1–477.14
See application file for complete search history.

(56) References Cited

U.S. PATENT DOCUMENTS 5,567,120 A   10/1996  Hungerford et al.
6,261,262 B1   7/2001  Briggs et al.
(Continued)

FOREIGN PATENT DOCUMENTS

CA    2 292 602    1/2009
EP    0 984 814    11/2004
(Continued)

OTHER PUBLICATIONS

International Search Report issued Aug. 21, 2012 in corresponding International Application No. PCT/JP2012/063079.

*Primary Examiner* — Theodore Stigell
*Assistant Examiner* — Amber Stiles
(74) *Attorney, Agent, or Firm* — Wenderoth, Lind & Ponack, L.L.P.

(57) ABSTRACT

An infusion pump includes a pump body for holding a roller clamp 7, and a roller movement mechanism 3 for moving a roller 72 of the roller clamp 7 and operating in coordination with manipulation of a door lock mechanism. When the door lock mechanism is in an unlocked state, an infusion tube T is blocked by the roller clamp 72. This configuration reliably prevents free flow even if a door is not closed completely or if the door is accidentally left unlocked. After the finish of infusion treatment, the infusion tube T is blocked by the roller clamp 7 at the moment when the door lock mechanism is unlocked before the opening of the door. This configuration avoids a trouble of removing the infusion tube T from the infusion pump while a user forgets to block the infusion tube by the roller clamp 7.

5 Claims, 51 Drawing Sheets

(51) Int. Cl.
*F04B 43/00* (2006.01)
*F04B 43/08* (2006.01)
*F04B 43/12* (2006.01)
*F04B 49/10* (2006.01)
*A61M 39/28* (2006.01)

(52) U.S. Cl.
CPC ............ *F04B 49/10* (2013.01); *A61M 39/285* (2013.01); *A61M 2205/14* (2013.01); *A61M 39/286* (2013.01)

(56) References Cited

U.S. PATENT DOCUMENTS

2003/0009131 A1 * 1/2003 Van Antwerp et al. ....... 604/111

2009/0306592 A1 12/2009 Kasai et al.

FOREIGN PATENT DOCUMENTS

| EP | 2 272 552 | | 1/2011 | |
|---|---|---|---|---|
| JP | 2002-508685 | | 3/2002 | |
| JP | 2004-057577 | | 2/2004 | |
| JP | 2004057577 | * | 2/2004 | ............ A61M 5/168 |
| JP | 2007-167316 | | 7/2007 | |
| JP | 2007-222485 | | 9/2007 | |
| JP | 2008-113726 | | 5/2008 | |
| JP | 2009-119161 | | 6/2009 | |
| WO | 98/56453 | | 12/1998 | |
| WO | 2009/133705 | | 11/2009 | |

* cited by examiner

FIG.14
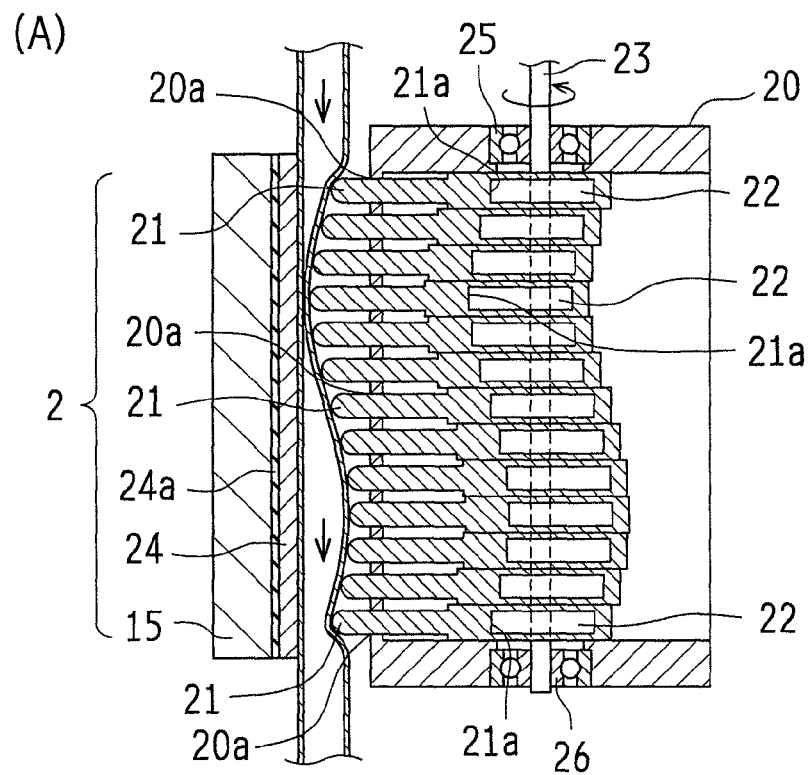
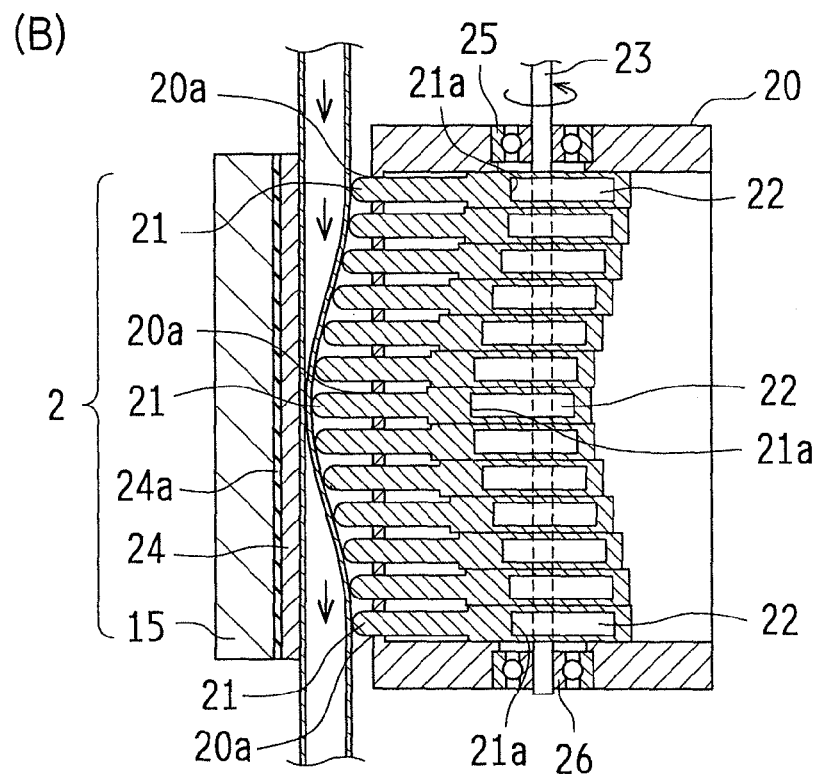

FIG.15
(A)
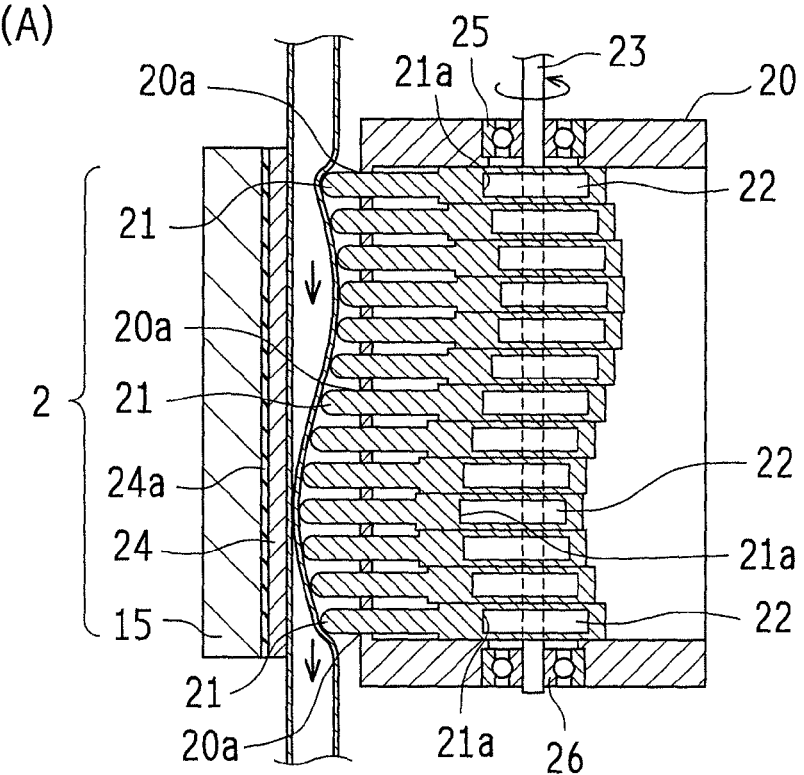
(B)
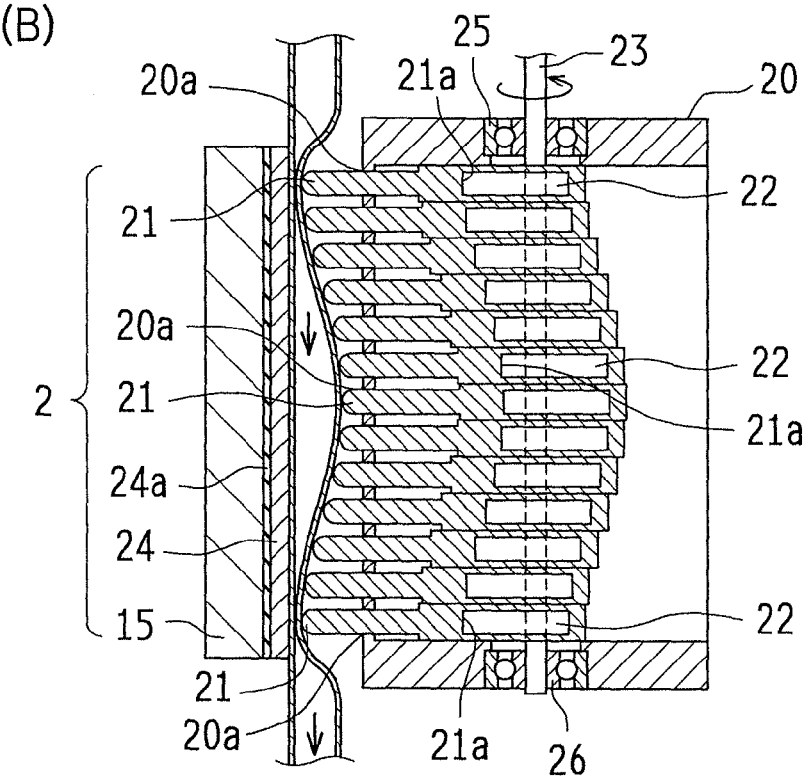

FIG.16
(A) Origin position
(A-1) when the clamp blocks the tube
(A-2) when the clamp releases the tube
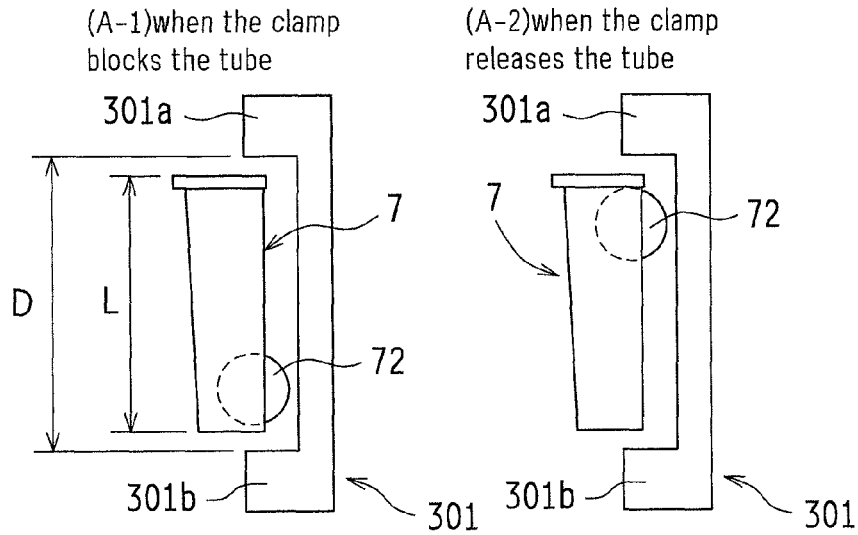
(B) Tube release position
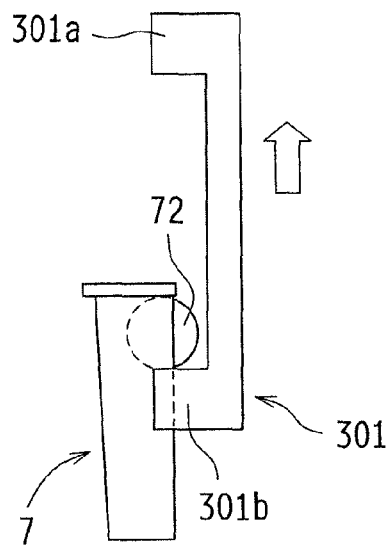
(C) Tube block position
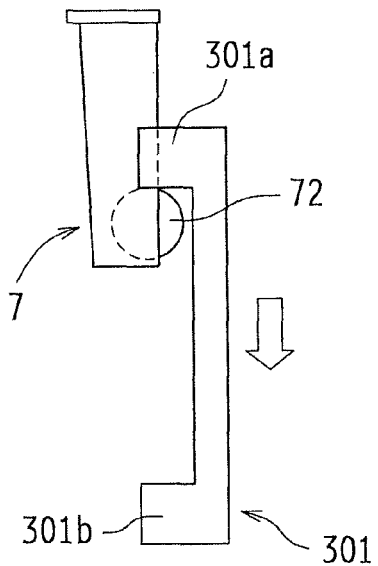

FIG. 24
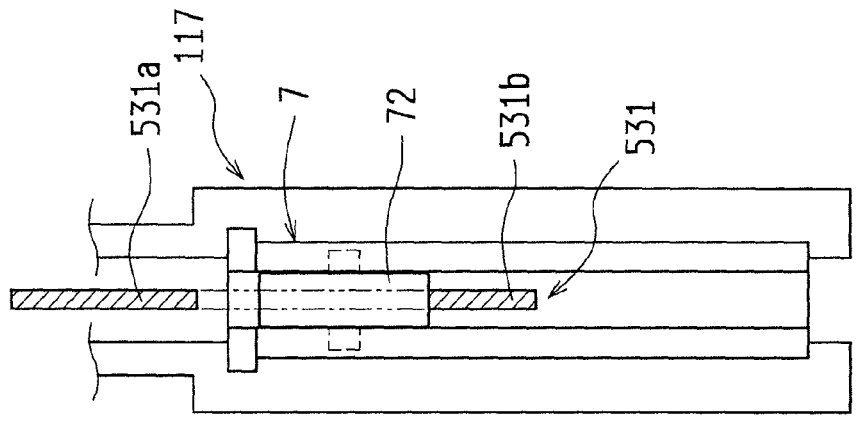
(B) Tube release action
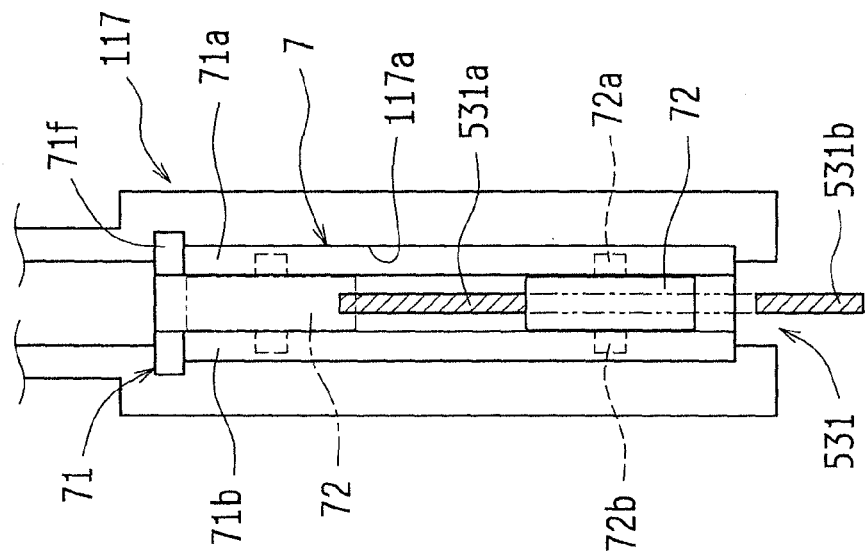
(A) Tube block action

FIG.25
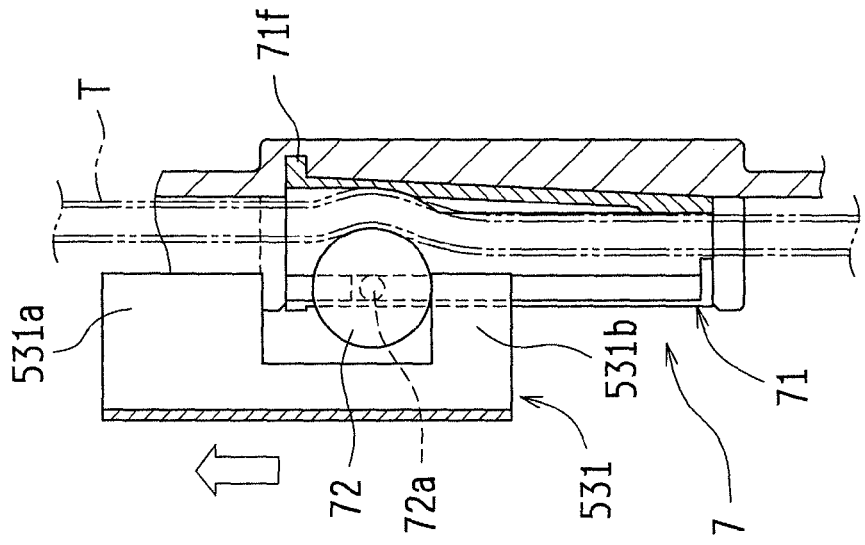
(A) Tube block action
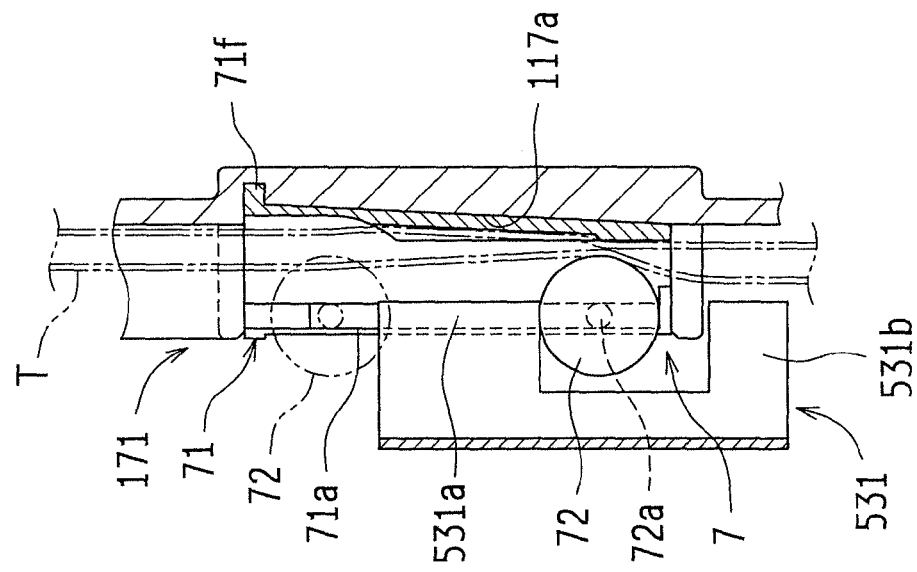
(B) Tube release action

FIG. 40
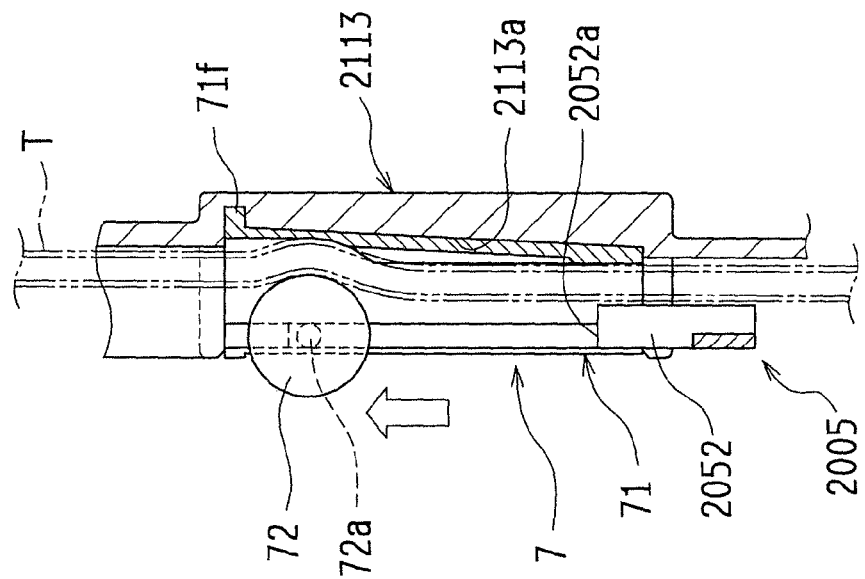
(A) Tube block action
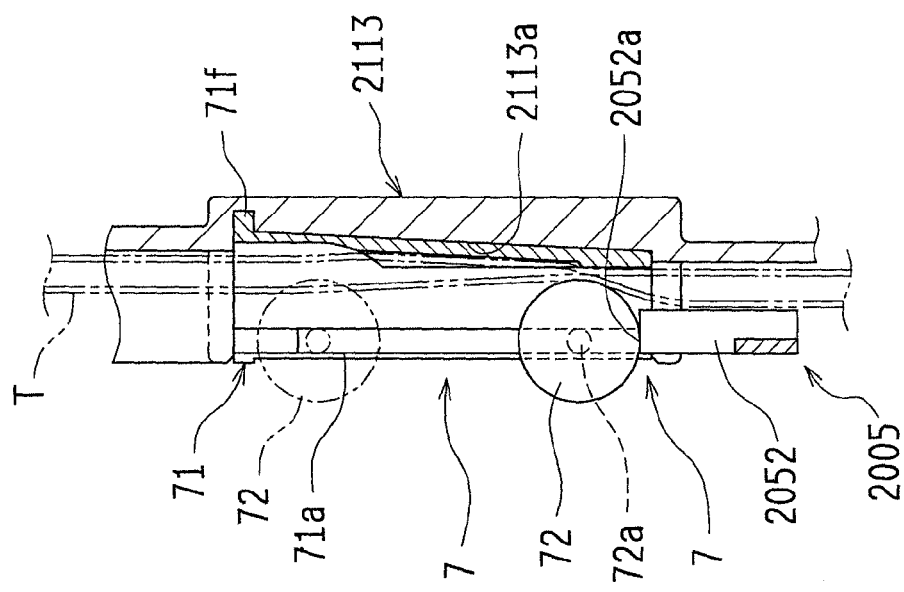
(B) Tube release action

FIG.44
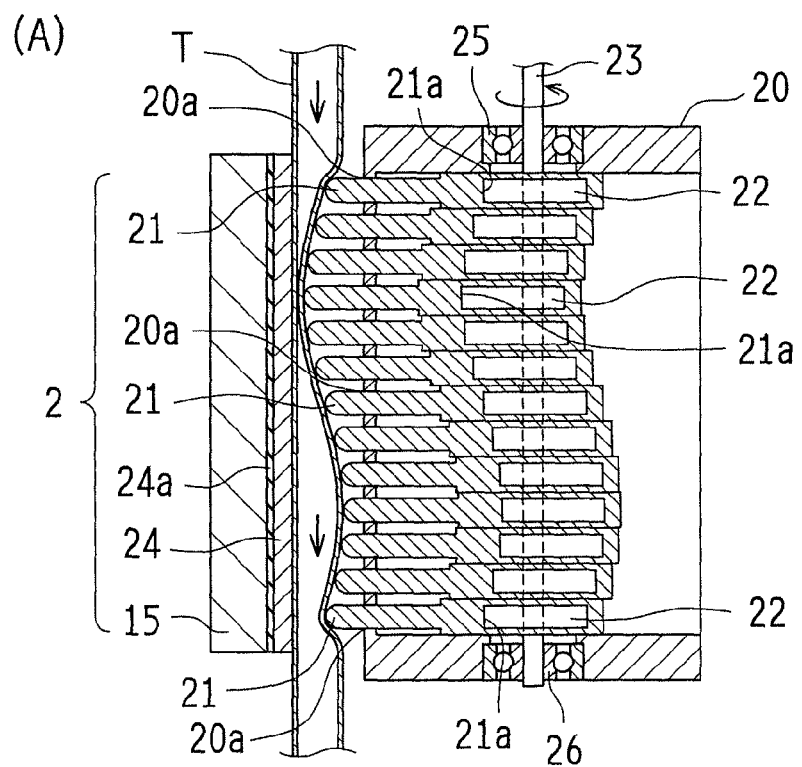
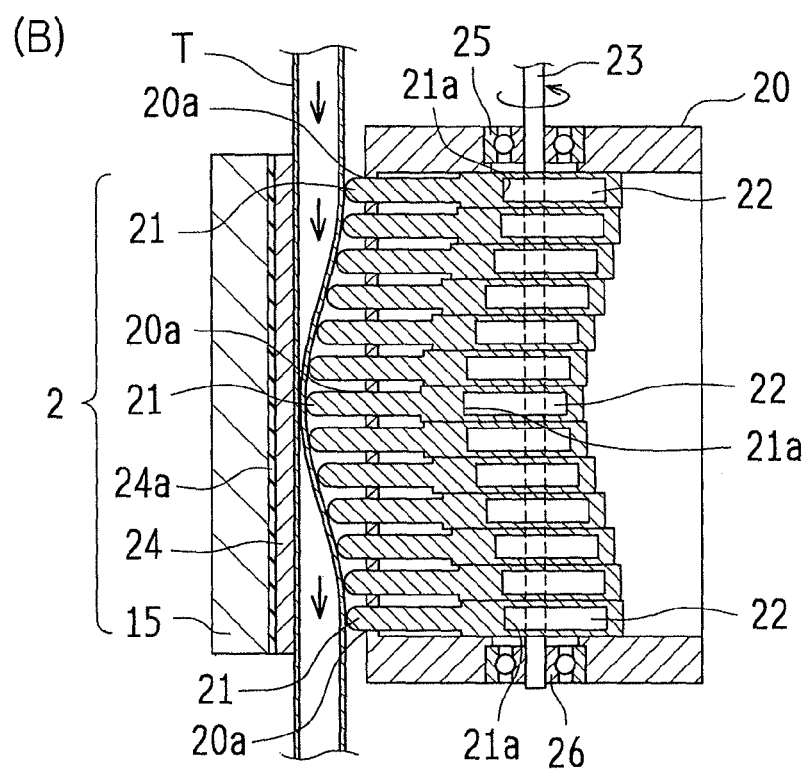

FIG.45
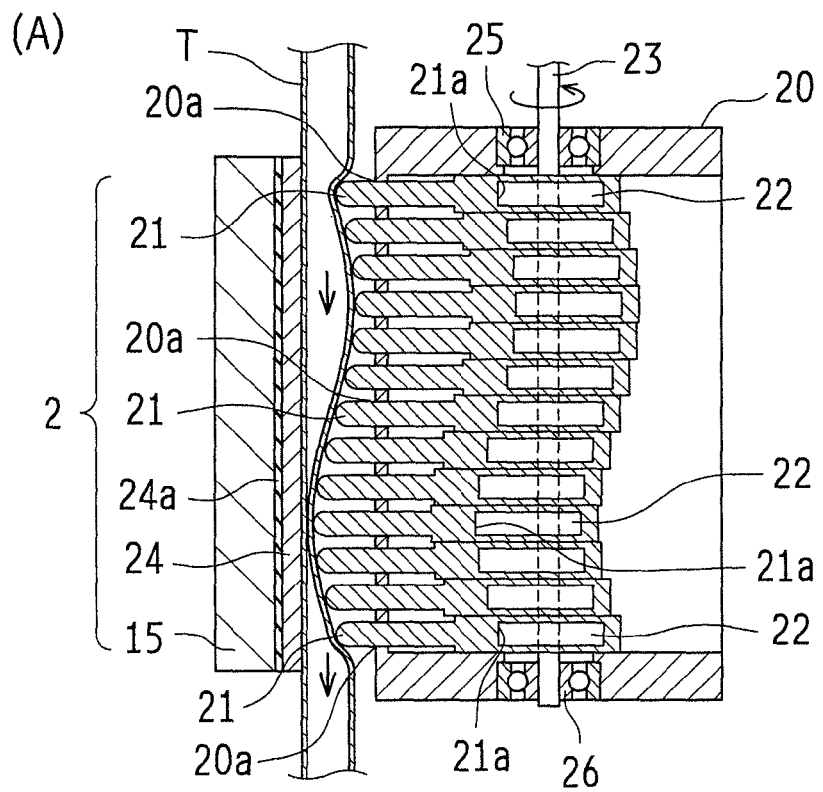
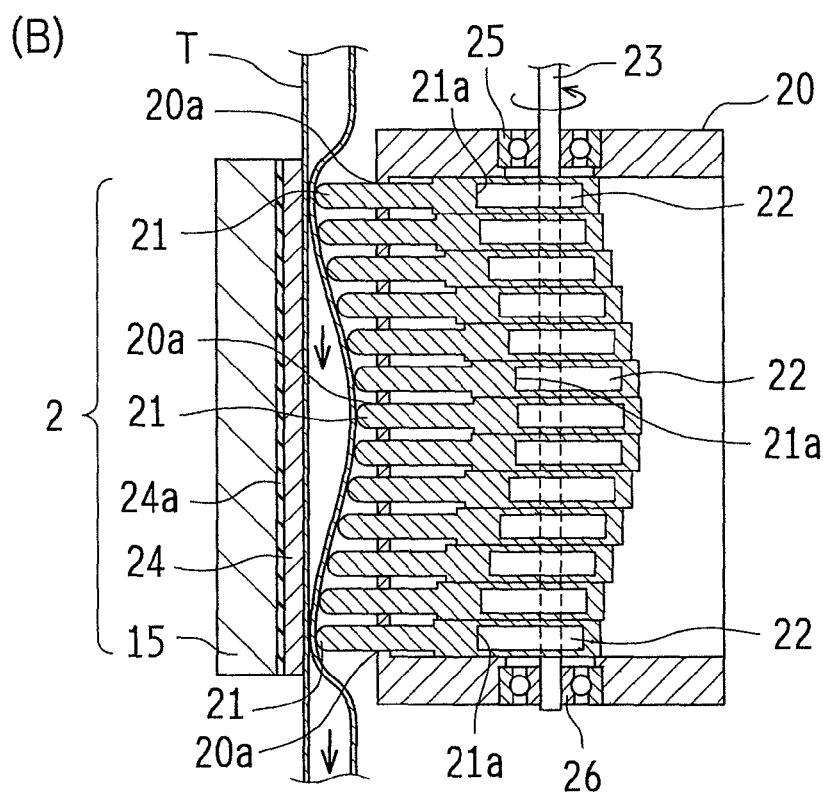

FIG.57
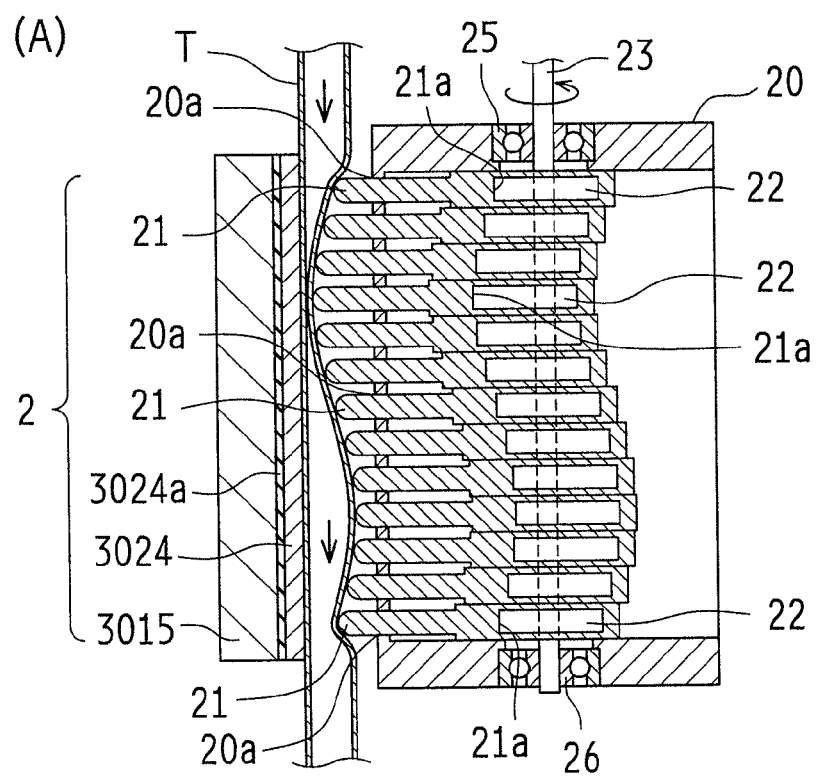
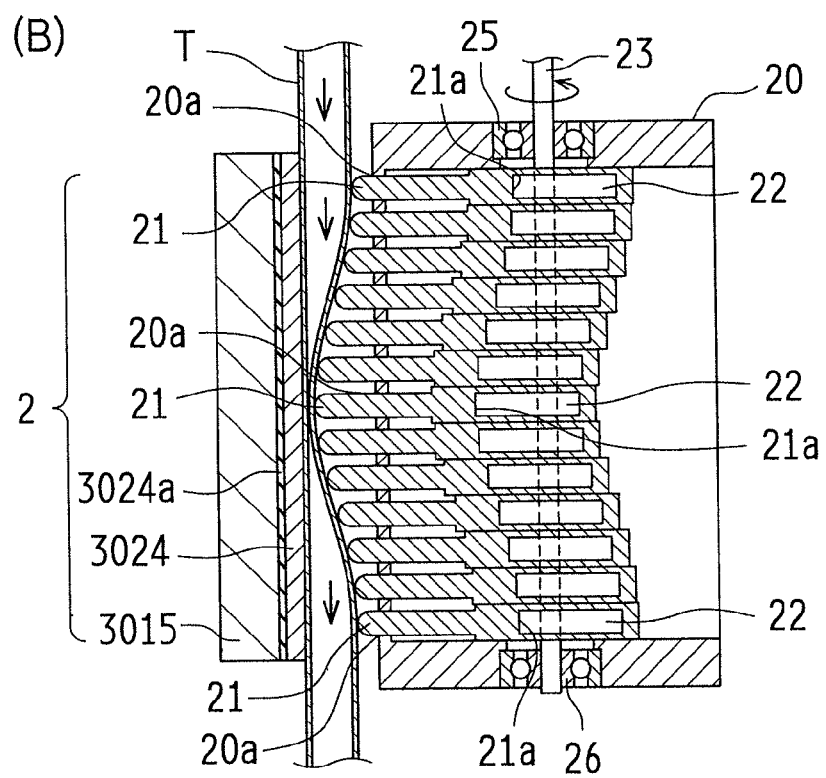

INFUSION PUMP

FIELD OF THE INVENTION

The present invention relates to infusion pumps.

BACKGROUND ART

As infusion pumps employed to infuse medical drug solution into a patient's body, various types of infusion pumps are known, including mechanical infusion pumps, gravity infusion pumps which entirely depend on gravity, and precompression-type infusion pumps.

Mechanical infusion pumps include syringe infusion pumps in which a piston of a syringe is pressed to feed infusion liquid, and peristaltic infusion pumps. Peristaltic infusion pumps include roller infusion pumps in which an infusion tube is pressed by a roller-equipped rotor or the like to feed infusion liquid, and finger infusion pumps.

Among these infusion pumps, a peristaltic finger infusion pump is equipped with a pump mechanism having, for example, a plurality of fingers aligned in one direction (along an infusion tube), cams for advancing and retracting the fingers independently, a door of the pump, and a pressing plate provided on the door in a manner opposed to tips of the fingers while the door is closed. With an infusion tube being connected to an infusion bag and attached between the plurality of fingers and the pressing plate, the cams cause the fingers to advance and retract independently. By such finger movements, the infusion tube is pressed successively by each of the fingers, so that infusion liquid is fed by a peristaltic action (see, for example, Patent Literature 1 and Patent Literature 2).

Infusion treatment using such an infusion pump poses a risk of "free flow". Free flow, an incident that infusion liquid falls under gravity and is administered to a patient in an excessive amount, may occur when an infusion tube is removed from the infusion pump or in other occasions. A conventional anti-free flow safeguard is to block an infusion tube by a roller clamp. A specific example of this safeguard is described below.

Generally, an infusion set for administering infusion liquid is composed of an infusion tube to be connected to an infusion bag, a drip chamber provided along the infusion tube, a roller clamp, a needle (an intravenous needle) connected to a patient's end of the infusion tube, and the like. A procedure for attaching the infusion tube of this infusion set to the infusion pump includes: blocking the infusion tube by the roller clamp, then attaching the infusion tube to a pump body (a pump mechanism unit) while the door of the infusion pump is kept open, and finally closing the door of the infusion pump. At this time (i.e. when the door is closed), at least one part of the infusion tube is blocked in the pump mechanism unit of the infusion pump. After the infusion tube is attached in this manner, a procedure for starting infusion treatment includes: releasing the roller clamp, and thereafter driving the infusion pump to start prescribed infusion treatment. A procedure after the finish of infusion treatment includes: stopping the infusion pump, then blocking the infusion tube by the roller clamp, opening the door of the infusion pump in this state (an anti-free flow state), and removing the infusion tube. These operational procedures can prevent free flow during preparation of infusion treatment and during removal of the infusion tube from the infusion pump.

As the examples of anti-free flow safeguards, Patent Literature 3 and Patent Literature 4 mentioned below disclose use of special clamps with an anti-free flow function.

PRIOR ART REFERENCES

Patent Literature

[Patent Literature 1] JP 2008-113726 A
[Patent Literature 2] JP 2007-167316A
[Patent Literature 3] JP 2004-057577A
[Patent Literature 4] JP 2009-119161A

SUMMARY OF THE INVENTION

Problems to be Solved by the Invention

However, the above-mentioned operational procedures for preventing free flow with use of a roller clamp of the infusion set may still cause free flow, if the roller clamp is released by mistake after the infusion tube is attached to the infusion pump but before the door of the infusion pump is closed. Further, free flow may occur even after the door is closed, if the roller clamp is released while the door is left unlocked by mistake, namely, while the infusion tube is incompletely blocked at the pump mechanism unit of the infusion pump. Furthermore, free flow may occur even after the finish of infusion treatment, if the door of the infusion pump is opened by mistake before the infusion tube is blocked by the roller clamp. Besides, an infusion pump may also cause free flow, if the door of the infusion pump is opened accidentally during infusion treatment.

Thus, conventional infusion sets have a risk of free flow due to operational errors by health-care professionals such as nurses or due to some other causes, and a remedy for this problem has been desired.

The present invention has been made in view of the situations, and intends to provide an infusion pump which can reliably prevent free flow.

Means to Solve the Problems

The present invention concerns an infusion pump which includes a pump mechanism for pressing an infusion tube and feeding infusion liquid in the infusion tube in one direction, a pump body equipped with the pump mechanism, a door for covering an infusion tube attachment position in the pump body in a freely opening and closing manner, and a door lock mechanism for locking the door closed. In this infusion pump, the pump body includes a clamp holding part for holding a roller clamp equipped with a roller, and roller movement means for moving the roller of the roller clamp held by the clamp holding part, the roller clamp being configured to block or release the infusion tube in response to movement of the roller. The roller movement means, operating in coordination with manipulation of the door lock mechanism, is characterized by locating the roller of the roller clamp at a position for releasing the infusion tube when the door lock mechanism is in a locked state, and locating the roller of the roller clamp at a position for blocking the infusion tube when the door lock mechanism is in an unlocked state.

According to this invention, the roller clamp is held in the pump body, and the roller movement means is configured to move the roller of the roller clamp in coordination with manipulation of the door lock mechanism. When the door lock mechanism is in an unlocked state, the roller of the roller clamp is configured to stay at a position for blocking the infusion tube. Hence, even after the door of the infusion pump is closed, the infusion tube is kept blocked by the roller clamp unless the door is locked. This configuration can reliably prevent free flow that may occur when the door is closed incompletely or left unlocked by accident.

When the door lock mechanism is manipulated to open the closed door, this manipulation causes the roller clamp to block the infusion tube. Hence, even if the door is opened by mistake during infusion treatment or in other situations, free flow is avoided. Further, after the finish of infusion treatment, at the moment when the door lock mechanism is manipulated to the unlocked state before the door is opened, the infusion tube is blocked by the roller clamp without fail. Therefore, this invention also avoids a trouble of "removing the infusion tube from the infusion pump while a user forgets to block the infusion tube by the roller clamp".

Accordingly, the present invention can reliably prevent free flow due to operational errors by health-care professionals such as nurses or due to some other causes.

As a specific configuration of this invention, the roller movement means includes a movement mechanism (for example, a rack-and-pinion mechanism) for allowing the roller of the roller clamp held by the clamp holding part to move between the infusion tube release position and the infusion tube block position, an actuator (an electric motor) for activating the movement mechanism, a lock detection sensor for detecting whether the door lock mechanism is at a locked position, and a control unit. The control unit controls activation of the actuator based on a detection result by the lock detection sensor. The control unit is configured to locate the roller of the roller clamp at the infusion tube release position when the door lock mechanism is at the locked position, and is configured to locate the roller of the roller clamp at the infusion tube block position when the door lock mechanism is not at the locked position.

As another specific configuration of this invention, the door lock mechanism is configured to lock or unlock the door in response to turning manipulation of a lock lever. The roller movement means includes a manipulation force transmission mechanism (for example, a lock piece having an arc-like gear, and a rack gear) which converts a turning manipulation force of the lock lever into a force for moving the roller of the roller clamp held by the clamp holding part. The roller movement means is configured to locate the roller of the roller clamp at the infusion tube release position when the lock lever of the door lock mechanism is manipulated to a locked position, and to locate the roller of the roller clamp at the infusion tube block position when the lock lever of the door lock mechanism is manipulated to an unlocked position.

The present invention further concerns an infusion pump including a pump mechanism for pressing an infusion tube and feeding infusion liquid in the infusion tube in one direction, a pump body equipped with the pump mechanism, and a door for covering an infusion tube attachment position in the pump body in a freely opening and closing manner. The pump body includes a clamp holding part for holding a roller clamp equipped with a roller, the roller clamp being configured to block or release the infusion tube in response to movement of the roller. This infusion pump is configured to expose a part of the roller of the roller clamp to an outside through an opening (a roller through hole) formed in the door, while the roller clamp is held by the clamp holding part and the door is closed. This infusion pump further includes a door lock mechanism for locking the door closed. As one of the technical features, the door lock mechanism includes a lock piece and an engagement member which are engageable with each other. This door lock mechanism is configured to allow the lock piece and the engagement member to be engaged with each other and thereby to lock the door closed, while the door is closed and the roller of the roller clamp held by the clamp holding part is located at a tube release position. The door lock mechanism is also configured to allow the lock piece and the engagement member to be disengaged from each other and thereby to unlock the door, while the door is closed and the roller of the roller clamp held by the clamp holding part is located at a tube block position.

According to the infusion pump of this invention, the lock piece and the engagement member of the door lock mechanism is kept engaged (locked), unless the roller of the roller clamp is manipulated to the tube block position while the door is closed (locked). Even if someone tries to open the door by mistake during infusion treatment, this configuration prohibits the door from being opened, and thus can prevent free flow due to an operational error. In addition, after the finish of infusion treatment, if someone tries to open the door before the infusion tube is blocked by the roller clamp, this configuration prohibits the door from being opened. Eventually, the infusion pump of this invention can also avoid a trouble of removing the infusion tube from the infusion pump while a user forgets to block the infusion tube by the roller clamp (the situation where free flow may occur).

Accordingly, the infusion pump according to this invention can reliably prevent free flow due to operational errors by health-care professionals such as nurses or due to some other causes.

As an specific example of the door lock mechanism applied to the infusion pump according to this invention, the door lock mechanism includes a lock lever which is capable of turning around a fulcrum axis and which has the lock piece at an end of the lock lever, an actuator which is provided at another end of the lock lever and which is capable of contacting the roller of the roller clamp held by the clamp holding part, and a lock spring for biasing the lock lever to a locked position at which the lock piece and the engagement member are engaged with each other. While the actuator of the lock lever is free, the lock piece is located at the locked position at which the lock piece and the engagement member are engaged with each other by an elastic force of the lock spring. While the door is closed and when the roller of the roller clamp held by the clamp holding part is manipulated to move to the tube block position, the actuator of the lock lever abuts the roller during the movement of the roller and is displaced against the elastic force of the lock spring, and the lock piece is located at an unlocked position.

According to the infusion pump in this configuration, while the door is open, the lock piece of the lock lever stays at the locked position by the elastic force of the lock spring. Hence, if the roller clamp is held by the clamp holding part but the roller of the roller clamp is not at the tube block position, the door cannot be closed, despite an attempt to do so, because of interference between the lock piece and the engagement member (see, for example, FIG. 41).

Also according to the infusion pump in this configuration, while the door is closed (locked), the lock piece stays at the locked position by the elastic force of the lock spring, unless the roller of the roller clamp is manipulated to the tube block position. As far as the lock piece stays at the locked position, the lock piece and the engagement member of the door lock mechanism are kept engaged (locked), thereby prohibiting the door from being opened. Hence, this configuration can prevent free frow that may occur when the door is opened by mistake during infusion treatment. Also in the infusion pump of this configuration, after the finish of infusion treatment, the roller exposed to the outside of the door is rotationally manipulated to block the infusion tube by the roller clamp, thereby unlocking the door and allowing the door to be open.

Effects of the Invention

The present invention can reliably prevent free flow due to operational errors by health-care professionals such as nurses or due to some other causes.

BRIEF DESCRIPTION OF THE DRAWINGS

FIGS. 14(A) and 14(B) explain actions of the pump mechanism.

FIGS. 15(A) and 15(B) explain actions of the pump mechanism.

FIGS. 16(A), 16(B) and 16(C) show other examples of the roller movement mechanism.

FIGS. 24(A) and 24(B) explain actions of the roller movement mechanism.

FIGS. 25(A) and 25(B) explain actions of the roller movement mechanism.

FIGS. 40(A) and 40(B) are vertical cross-sectional views showing the roller clamp held by the clamp holding part in the pump body.

FIGS. 44(A) and 44(B) explain actions of the pump mechanism.

FIGS. 45(A) and 45(B) explain actions of the pump mechanism.

FIGS. 57(A) and 57(B) explain actions of the pump mechanism.

MODE FOR CARRYING OUT THE INVENTION

Embodiments of the present invention are hereinafter described with reference to the drawings.
—Infusion Set—
Prior to the description of the infusion pump, an infusion set for infusion treatment is described with reference to FIG. 27.

Figure 27:
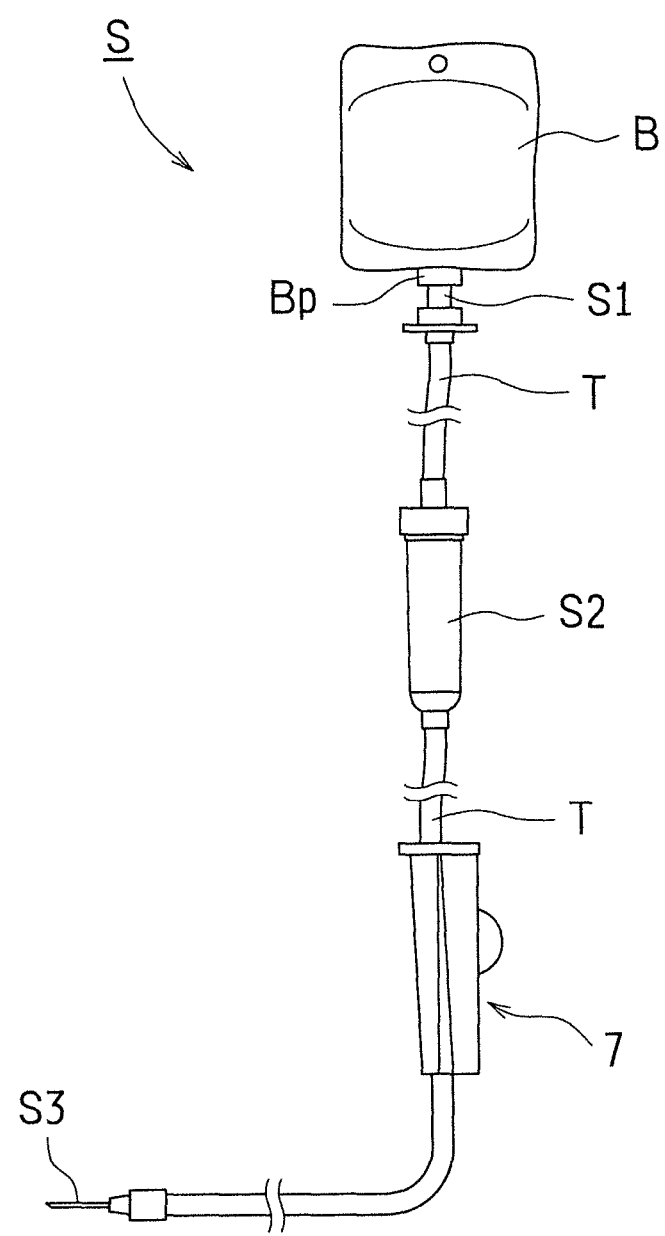
FIG. 27 shows a schematic configuration of an infusion set.

An infusion set S shown in FIG. 27 is composed of an infusion bag B containing a drug solution, a spike S1 to be inserted in a port Bp of the infusion bag B, a drip chamber S2 for visually inspecting the flow rate of the infusion liquid, an upstream infusion tube T for connecting the spike S1 and the drip chamber S2, a downstream infusion tube T connected to the drip chamber S2, a roller clamp 7 provided along the downstream infusion tube T, and a needle (an intravenous needle) S3 connected to a patient's end of the infusion tube T.

Figure 28:
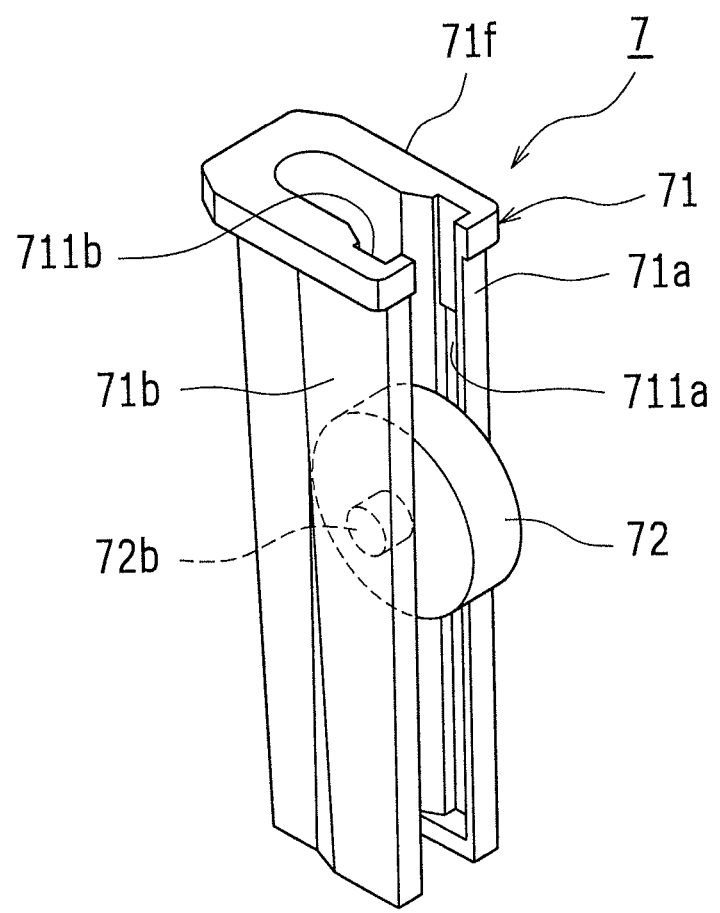
FIG. 28 is a perspective view of a roller clamp.
Figure 29:
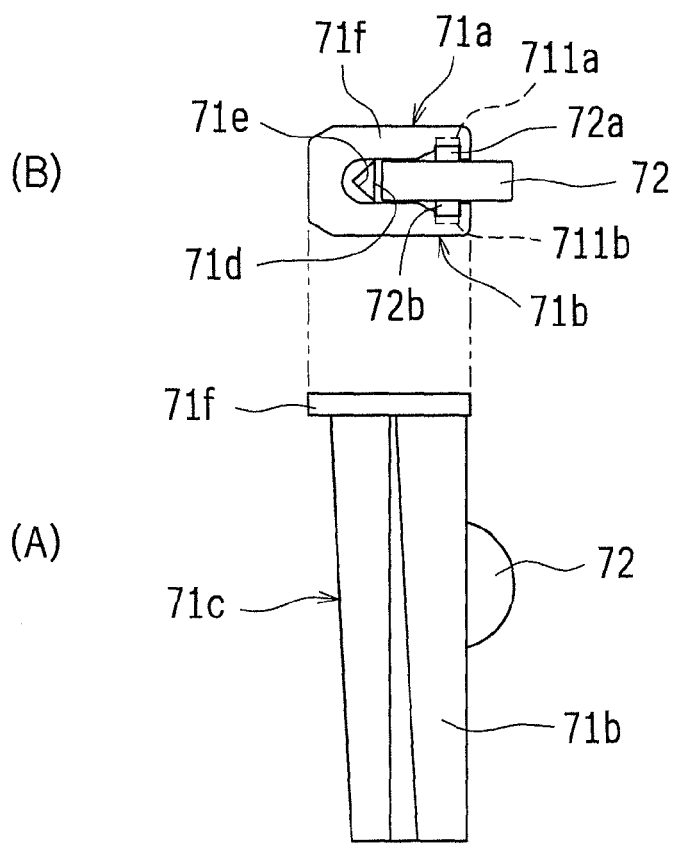
FIG. 29(A) is a side view of the roller clamp.
FIG. 29(B) is a plan view thereof, with the two views being laid out together.
Figure 30:
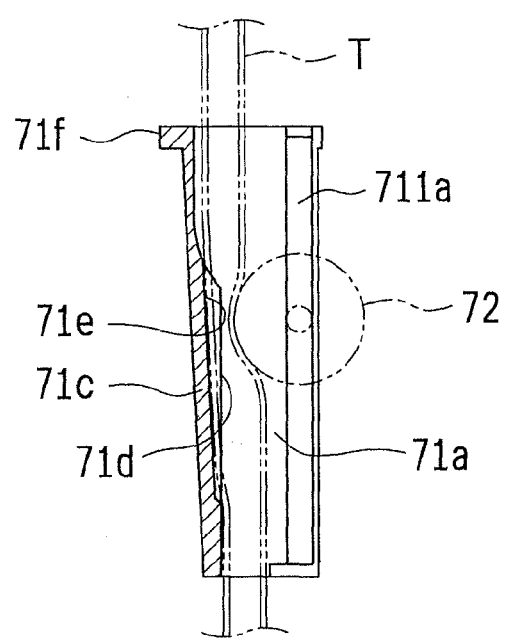
FIG. 30 is a cross-sectional view of the roller clamp.

As illustrated in FIG. 28 to FIG. 30, the roller clamp 7 is composed of a clamp body 71 and a roller 72. The clamp body 71 is a single-piece resin-molded member composed of a pair of side walls 71a, 71b opposed to each other at a predetermined gap, and a bottom plate 71c. In inner surfaces of the side walls 71a, 71b, guide grooves 711a, 711b are provided in order to hold and guide rotation shafts 72a, 72b of the roller 72. A bottom surface 71d (a top surface of the bottom plate 71c) of the clamp body 71 is provided with a V-shaped groove 71e. The bottom surface 71d of the clamp body 71 is inclined relative to the guide grooves 711a, 711b, in such a manner that a distance between the guide grooves 711a, 711b and the bottom surface 71d decreases from one end of the clamp body 71 (an end nearer to the flange 71f) to the other end thereof.

The roller 72 is rotationally movable along the guide grooves 711a, 711b, between one end of the clamp body 71 (the end nearer to the flange 71f) and the other end thereof (the opposite end from the flange 71f). When the roller 72 stays at the movement end nearer to the flange 71f (a release-side movement end), the gap between the outer periphery of the roller 72 and the bottom surface 71d of the clamp body 71 is at the maximum. On the other hand, when the roller 72 stays at the movement end opposite to the flange 71f (a block-side movement end), the gap between the outer periphery of the roller 72 and the bottom surface 71d of the clamp body 71 is at the minimum.

In the roller clamp 7 of this structure, the infusion tube T is blocked and released in the following manner. With the infusion tube T inserted between the bottom surface 71d of the clamp body 71 and the outer periphery of the roller 72, the roller 72 is rotated to the block-side movement end of the clamp body 71 to block the infusion tube T completely. From this state, while the roller 72 is rotated toward the flange 71f of the clamp body 71, the rotational movement of the roller 72 causes a gradual decrease in the degree of pressing (flattening) the infusion tube T and an eventual increase in the amount of infusion liquid allowed to flow through the infusion tube T. When the roller 72 has reached the release-side movement end, the infusion tube T is no longer pressed by the roller 72 (the infusion tube T is fully released).

Embodiment 1-1
—Infusion Pump—
An example of an infusion pump according to the present invention is described with reference to FIG. 1 to FIG. 15.

An infusion pump 1 in this example is a peristaltic finger infusion pump, and is equipped with a pump body (a casing) 11, and a door 12 which closes on a front face (a tube attachment position) of the pump body 11. The door 12 is held swingably (in a freely turning manner) on the pump body 11 by hinges 14, 14, and is capable of swinging between a fully closed position and a fully open position (for example, a 180-degree open position) with respect to the front face of the pump body 11.

At the front face of the pump body 11, there are provided a tube attachment guide 111, a pump unit 112 which is connected to the tube attachment guide 111 and which has an enlarged rectangular shape, and a clamp holding recess 113, in this order from the upstream side in an infusion liquid feed direction. The groove width of the tube attachment guide 111 corresponds to an outer diameter of the infusion tube T of the above-mentioned infusion set. Tips of fingers 21 . . . 21 in the pump mechanism 2 (to be described later) are located in the pump unit 112.

The tube attachment guide 111 has a transversely curved (bent) shape. The door 12 is further provided with a pressing plate 24 at an inner face thereof. The pressing plate 24 is positioned to face the tips of the fingers 21 . . . 21 in the pump mechanism 2 while the door 12 is closed.

Figure 1:
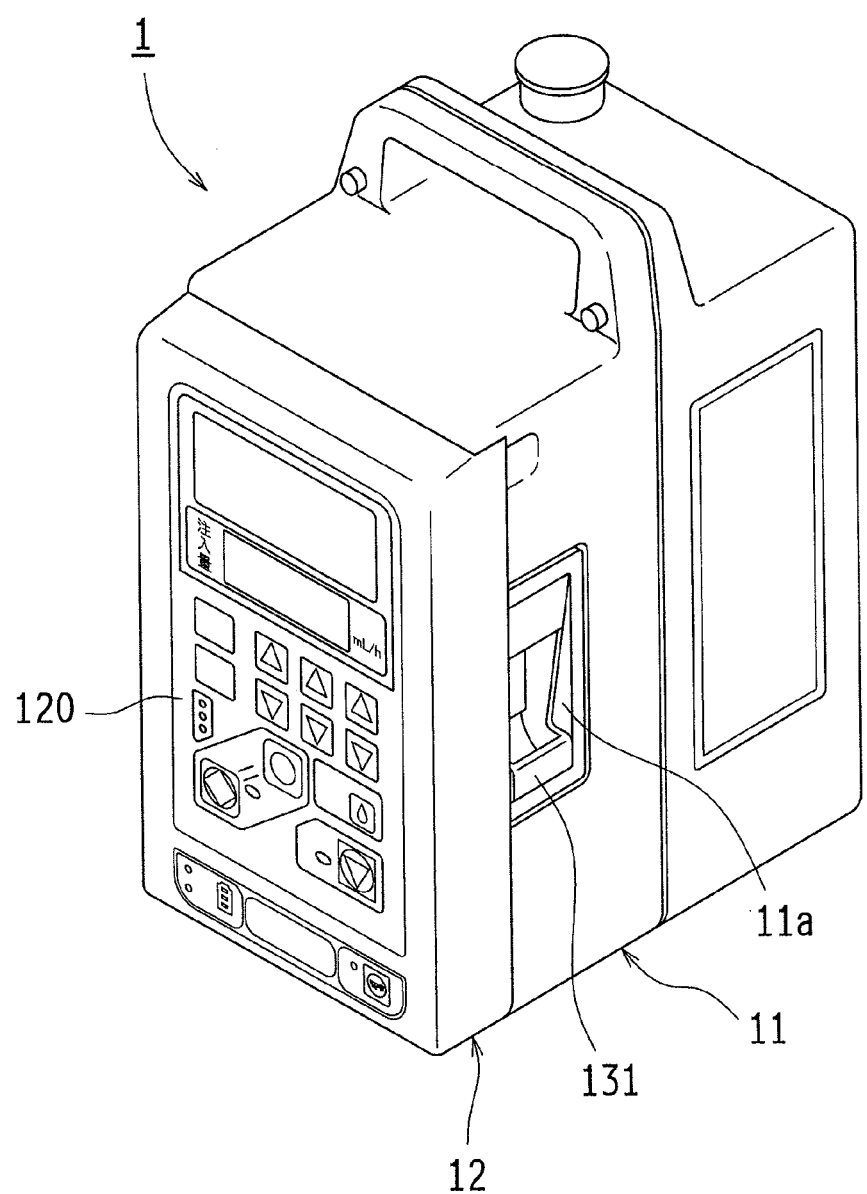
FIG. 1 is a perspective view showing an external appearance of an exemplary infusion pump according to the present invention.
Figure 2:
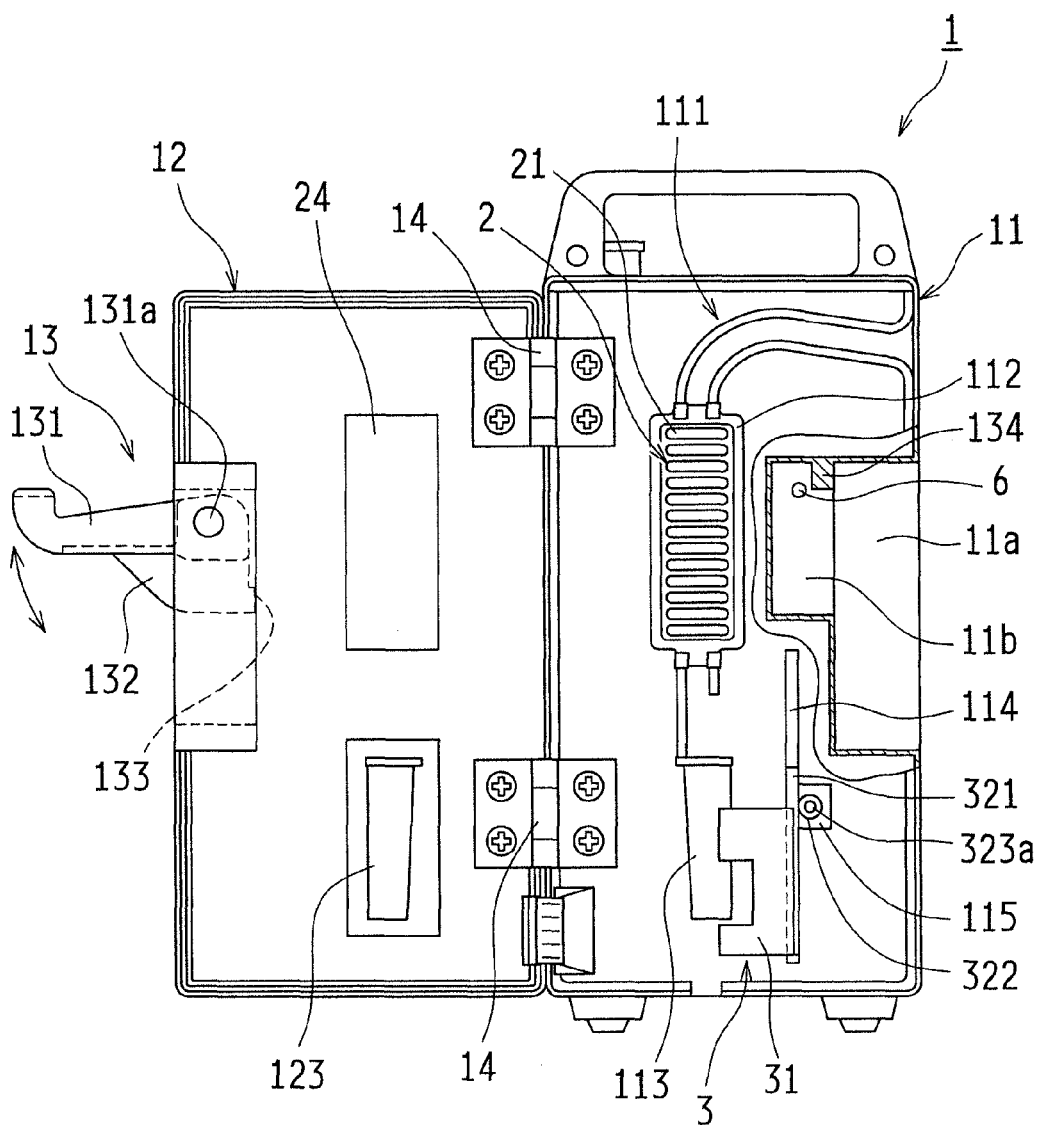
FIG. 2 shows a schematic configuration of an exemplary infusion pump according to the present invention, in a state where the door of the infusion pump is open.
Figure 6:
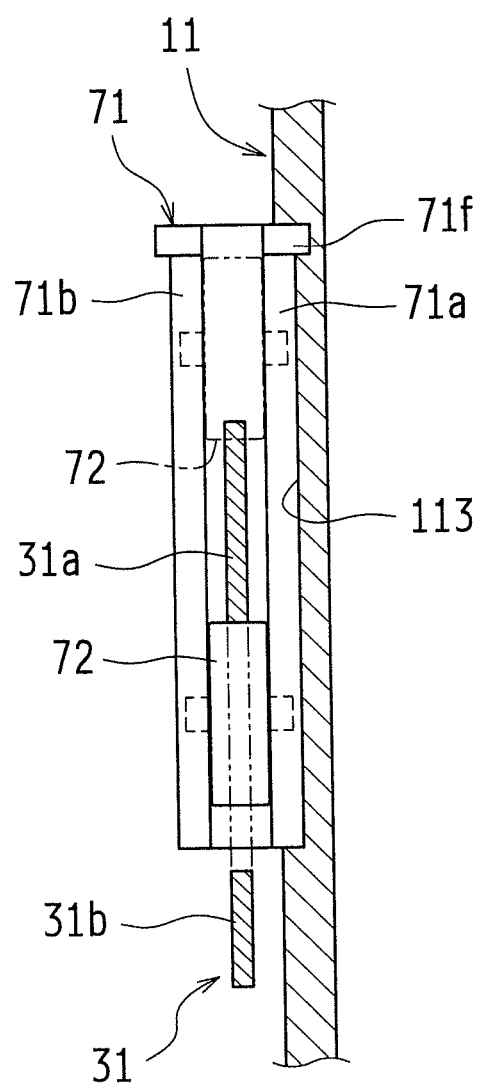
FIG. 6 is a cross-sectional view taken along the line I-I in FIG. 5, showing only around the roller clamp holding part.

As shown in FIG. 2 and FIG. 6, the clamp holding recess 113 is shaped to receive the first side wall 71a of the roller clamp 7 in the above-mentioned infusion set S. With the roller clamp 7 (the clamp body 71) being fitted in the clamp holding recess 113, the infusion tube T is arranged vertically in the infusion pump 1, and can be released and blocked by vertical movements of the roller 72.

Figure 8:
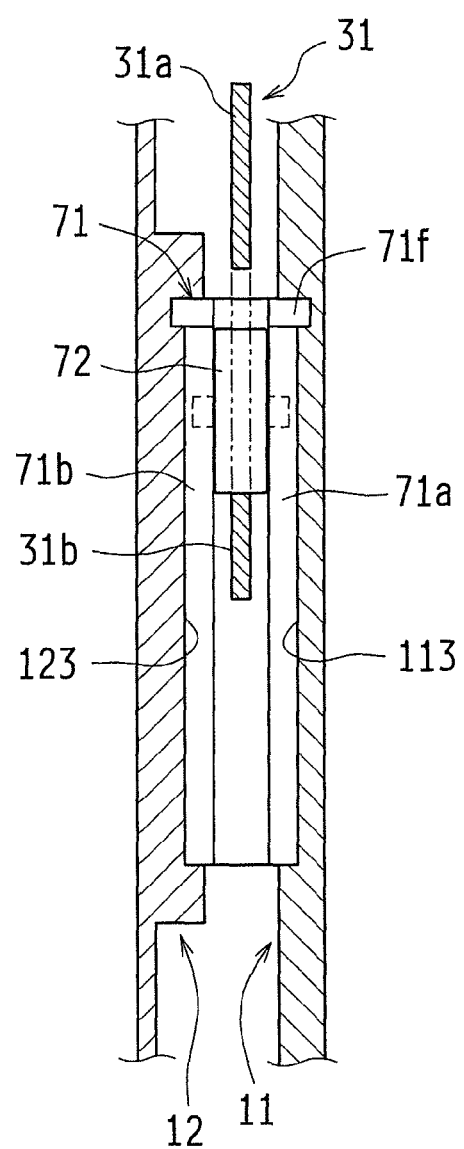
FIG. 8 is a cross-sectional view taken along the line II-II in FIG. 7, showing only around the roller clamp holding part.

In the inner face of the door 12, a clamp holding recess 123 is formed at a position corresponding to the clamp holding recess 113 in the front face of the pump body 11 (at a position opposed to the clamp holding recess 113 while the door 12 is closed). As shown in FIG. 2 and FIG. 8, the clamp holding recess 123 of the door 12 is shaped to receive the second side wall 71b of the roller clamp 7. The roller 72 of the roller clamp 7 held by these clamp holding recesses 113, 123 is allowed to move vertically by a roller movement mechanism 3 to be described later.

Figure 7:
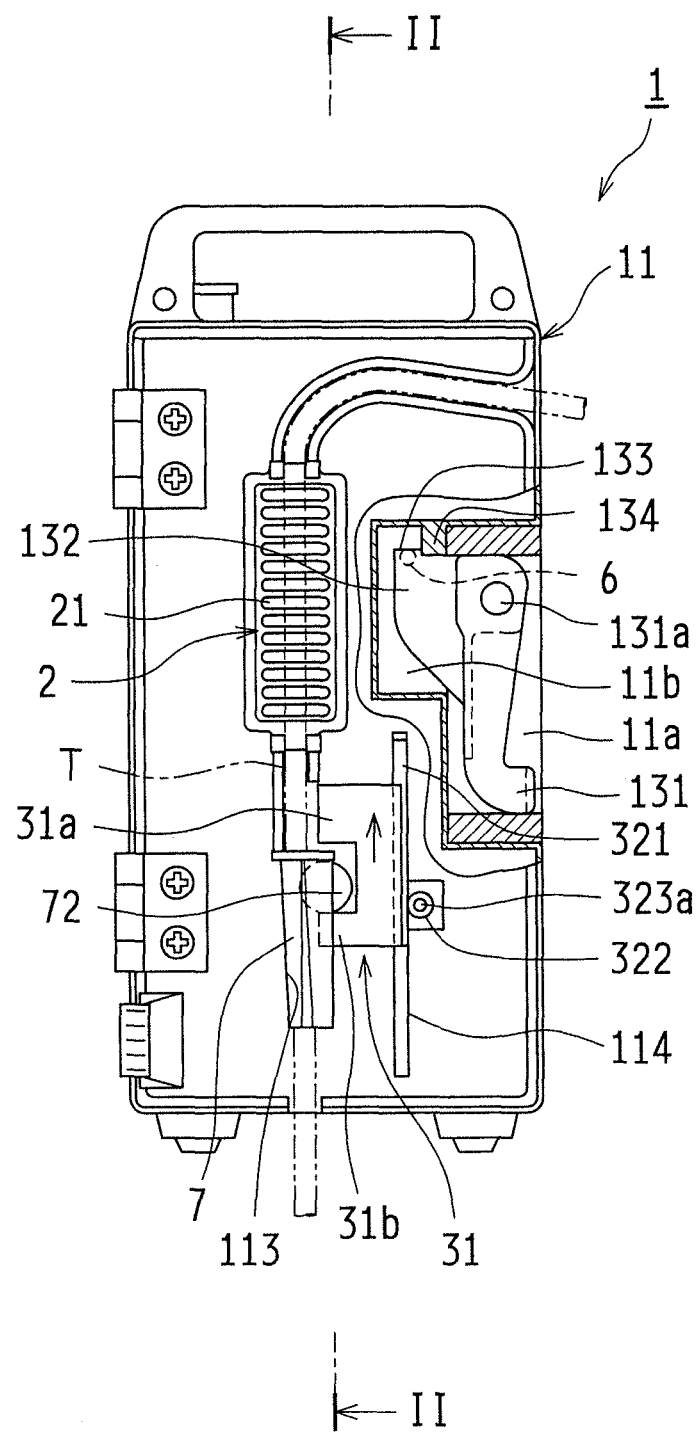
FIG. 7 is a schematic configuration of an exemplary infusion pump according to the present invention, in a state where the door (omitted in this figure) of the infusion pump is closed from the state shown in FIG. 5.

The pump body 11 is further provided with, at a side thereof, a lever housing recess 11a which can accommodate a lock lever 131 of a door lock mechanism 13 to be described later. At an inner side of the lever housing recess 1a, a lock chamber 1b for accommodating a lock piece 132 to be described later is further provided. When the lock piece 132 enters the lock chamber 11b, the swinging movement (turning) of the door 12 is restricted. Provided at an upper part of the lock chamber 11b is an engagement piece 134 for engaging with a lock latch 133 of the lock piece 132. Further provided in the vicinity of the engagement piece 134 is a lock detection sensor 6 for detecting whether the door lock mechanism 13 is at a locked position or not. The lock detection sensor 6 is a known photoelectric sensor (reflective type) composed of a light-emitting element and a light-receiving element. The lock detection sensor 6 outputs a lock detection signal (an ON signal) only when the lock latch 133 of the lock piece 132 is located at a position to engage with the engagement piece 134 (while the door 12 is kept closed), as shown in FIG. 7.

Figure 5:
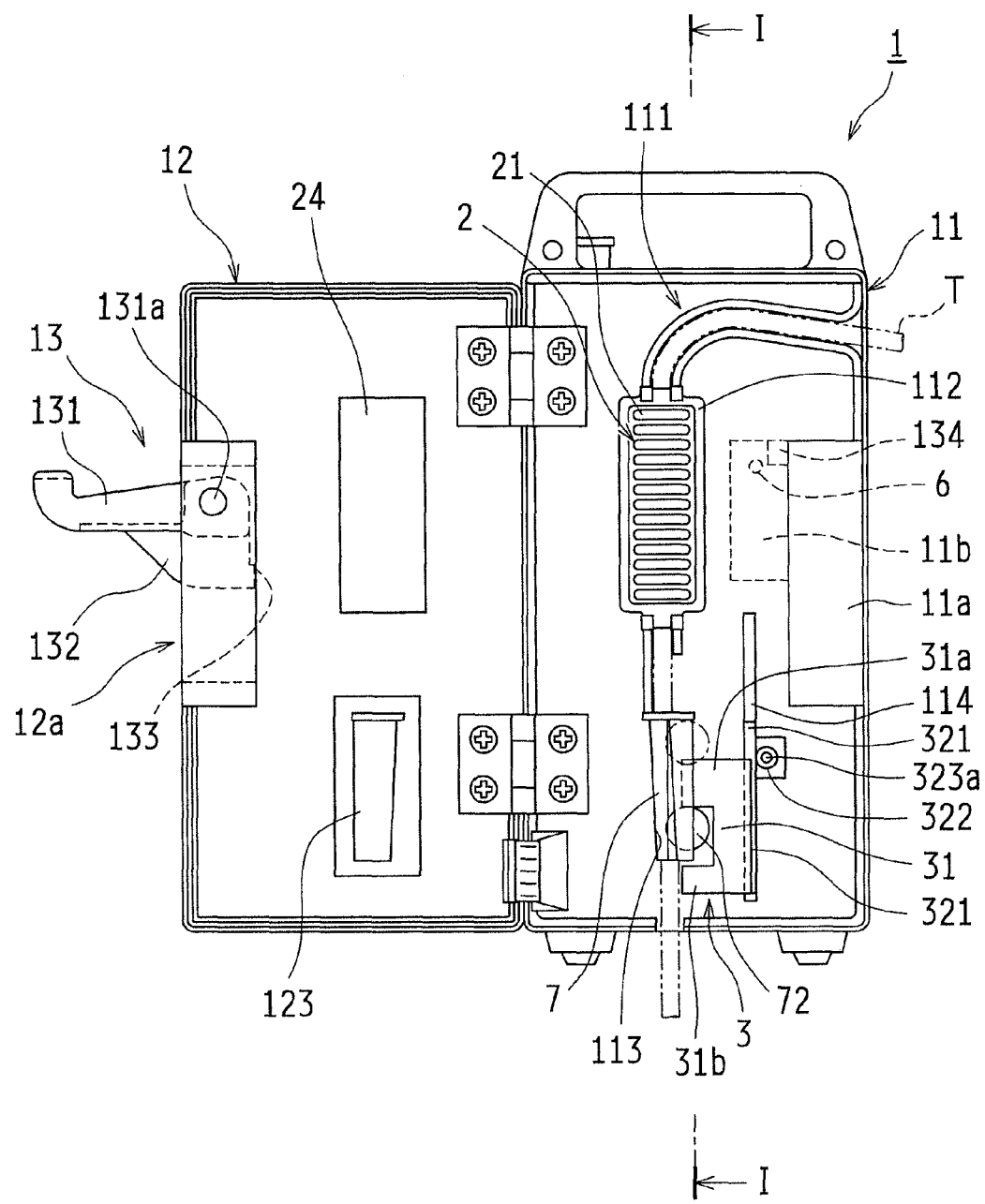
FIG. 5 shows a schematic configuration of an exemplary infusion pump according to the present invention, in a state where the door of the infusion pump is open and the roller clamp is held in the pump body.

A lock lever 131 is provided at a side end of the door 12 (an end opposite to the hinges 14). The lock lever 131 is rotatable around a rotation shaft 131a, and swingable (for example, swingable by about 90 degrees) between a lock release position (an unlocked position) as shown in FIG. 2 and FIG. 5 and a locked position for locking the door 12 (a position shown in FIG. 3 and FIG. 7). The lock lever 131 is integrally formed with a lock piece 132. A lock latch 133 is provided at a tip portion of the lock piece 132. When the lock lever 131 is manipulated to the locked position, the lock latch 133 engages with the above-described engagement piece 134 in the pump body 11, thereby keeping the door 12 fully closed. The lock lever 131, the lock piece 132, and the lock latch 133 in the door 12, and the engagement piece 134 in the pump body 11 constitute a door lock mechanism 13. The door lock mechanism 13 can be located at the locked position or the unlocked position by manipulation of the lock lever 131.

—Pump Mechanism—

Next, a specific example of the pump mechanism 2 is described with reference to FIG. 12 to FIG. 15. Among the elements illustrated in FIG. 12 to FIG. 15, the eccentric cams 22 are not shown in section.

The pump mechanism 2 is composed of a plurality of fingers 21 . . . 21 (13 fingers in the example shown in FIG. 12) aligned in one direction (a direction along the infusion tube T attached to the pump body 11), eccentric cams 22 . . . 22 for independently advancing and retracting the fingers 21, a camshaft 23 for rotating the eccentric cams 22, a pressing plate 24 mentioned above, a retention frame 20, and the like.

A front face of the retention frame 20 is provided with slots 20a . . . 20a which positionally correspond to the fingers 21. Tips of the fingers 21 are located at the front face side (the infusion tube T side) in the retention frame 20 and are configured to project through the slots 20a. Axial movements (movements in axial directions of the camshaft 23) of the fingers 21 . . . 21 are restricted by the retention frame 20. The fingers 21 are plate-like members which can move (advance and retract) independently while effecting sliding movements with respect to each other.

Each finger 21 has a cam hole 21a. A disc-shaped eccentric cam 22 is fitted in the cam hole 21a and is capable of rotating therein. The eccentric cams 22 . . . 22 are mounted on the camshaft 23 in an integrally rotatable manner.

Figure 13:
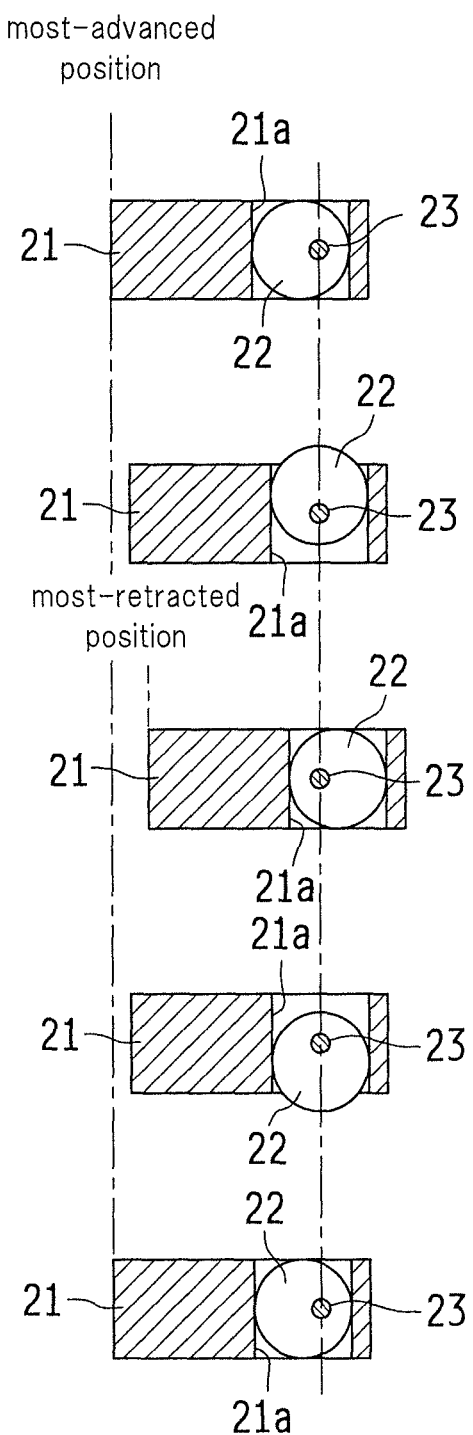
FIG. 13 illustrates a series of actions by a finger in the pump mechanism, wherein the finger is shown in section along a plane orthogonal to a camshaft.

Each of the disc-shaped eccentric cams 22 has its center offset from the camshaft 23. As shown in FIG. 13, one rotation (360-degree rotation) of the camshaft 23 causes the tip of the finger 21 to effect one reciprocating motion between the most-advanced position (a tube block position) and the most-retracted position (a full tube release position). These eccentric cams 22 are mounted on the camshaft 23, with a predetermined phase difference from each other (a phase difference in a rotation direction of the camshaft 23). Specifically, the phase difference between the eccentric cams 22 . . . 22 mounted on the camshaft 23 is such that the tips of the fingers 21 . . . 21 aligned in the axial direction of the camshaft 23 form a substantially sinusoidal wave (Such a phase difference is obtained by dividing 360 degrees by the number of eccentric cams 22.). FIG. 13 shows the positions of a finger 21, with every 90-degree rotation of the camshaft 23.

Figure 12:
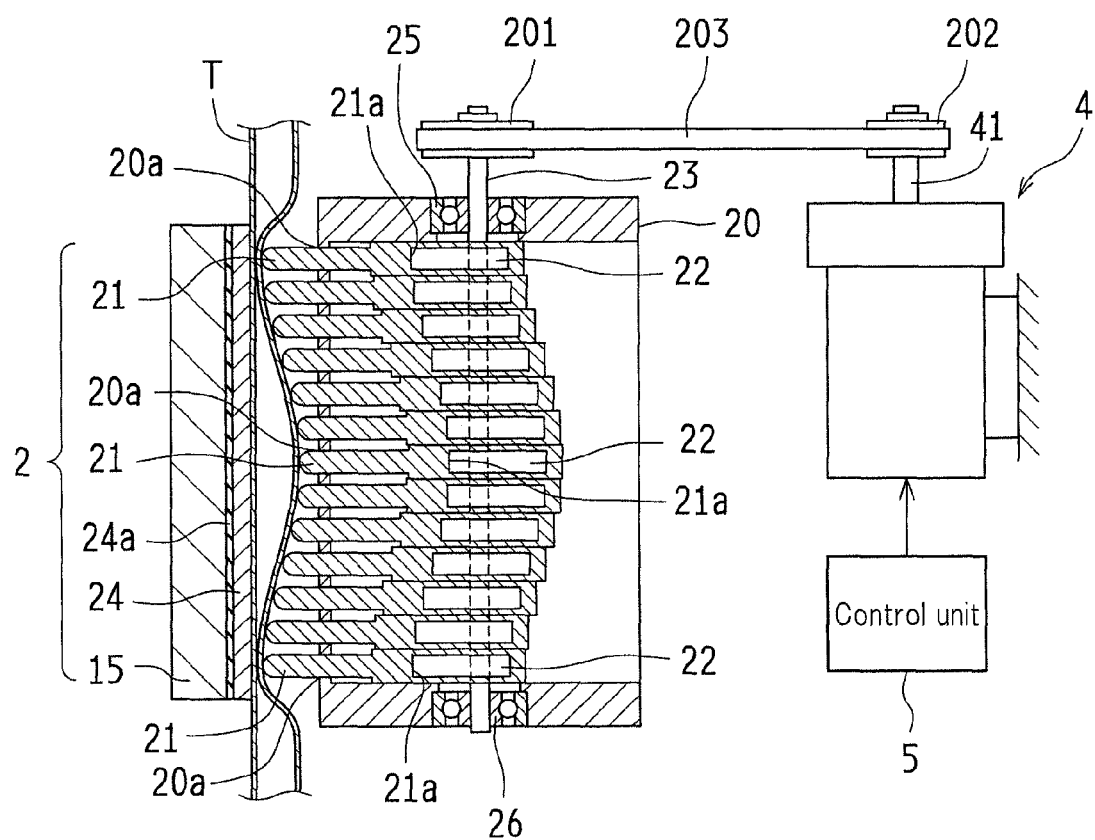
FIG. 12 shows a structure of a pump mechanism applied to the infusion pump according to the present invention.

As shown in FIG. 12, the camshaft 23 of the pump mechanism 2 is oriented vertically (in an alignment direction of the fingers 21 . . . 21). A lower end of the camshaft 23 is rotatably held by a bearing 26 provided in the retention frame 20. An upper part of the camshaft 23 penetrates upwardly through a wall of the retention frame 20. A penetration part of the camshaft 23 is provided with a bearing 25, which rotatably supports the upper part of the camshaft 23.

A timing pulley (an idler pulley) 201 is mounted at an upper end of the camshaft 23 in an integrally rotatable manner. A timing pulley (a drive pulley) 202 is mounted on a rotation shaft 41 of an electric motor (for example, a stepper motor) 4 in an integrally rotatable manner. A timing belt 203 is trained between the timing pulley 201 on the camshaft 23 and the timing pulley 202 on the rotation shaft 41. The camshaft 23 is driven to rotate by the electric motor 4. The drive (the number of revolutions) of the electric motor 4 is controlled by a control unit 5. In this example, the electric motor 4 is powered by a battery built in the infusion pump 1 or by a commercial power source.

When the camshaft 23 is driven to rotate by the electric motor 4, the eccentric cams 22 rotate in the cam holes 21a of the fingers 21. Along with the eccentric rotation of the eccentric cams 22, the fingers 21 advance and retract successively from upstream (upstream in the infusion liquid feed direction) to downstream. Specifically, as shown in FIGS. 14(A), 14(B) and FIGS. 15(A), 15(B), the tips of the fingers 21 move from upstream to downstream in a peristaltic wave-like pattern. Such advance and retraction (reciprocal movements) of the fingers 21 . . . 21 impart peristaltic movements to the infusion tube T positioned between the tips of the fingers 21 . . . 21 and the pressing plate 24, thereby feeding infusion liquid in the infusion tube T from upstream to downstream. In this example, in order to alleviate an overload imposed on the infusion tube T by the fingers 21 . . . 21, a buffer sheet 24a is provided between the pressing plate 24 and a base plate 15.

In this example, the control unit 5 is mainly configured by a microcomputer or the like. The control unit 5 can variably adjust the flow rate of the infusion liquid, for example, by controlling the number of revolutions of the electric motor 4 based on a preset flow rate of the infusion liquid (an amount of feeding the infusion liquid per unit time) that is manually input by an operation panel 120 (see FIG. 1) at a front face of the door 12. For example, the flow rate of the infusion liquid can be set in a range between 1 mL/h and 1200 mL/h, by an increment of [1 mL/h]. The control unit 5 also controls a drive of an electric motor 323 of a roller movement mechanism 3 to be described later. Further, the control unit 5 is configured to indicate operational information such as "flow rate of the infusion liquid (amount of infusion)" and "cumulative infusion time" as well as various alerts including "air-in-line" and "failure: door open" on the operation panel 120.

—Roller Movement Mechanism—

Next, a roller movement mechanism 3 is described with reference to FIG. 2 to FIG. 11.

A roller movement mechanism 3 in this example is a mechanism for moving the roller 72 of the roller clamp 7 between a block position (a block-side movement end) and a release position (a release-side movement end) for the infusion tube T, while the roller clamp 7 is held in the clamp holding recess 113 of the pump body 11 and the clamp holding recess 123 of the door 12.

The roller movement mechanism 3 is composed of a roller slider 31, a rack gear 321, a pinion gear 322, an electric motor (for example, a stepper motor) 323, and the like.

Figure 9:
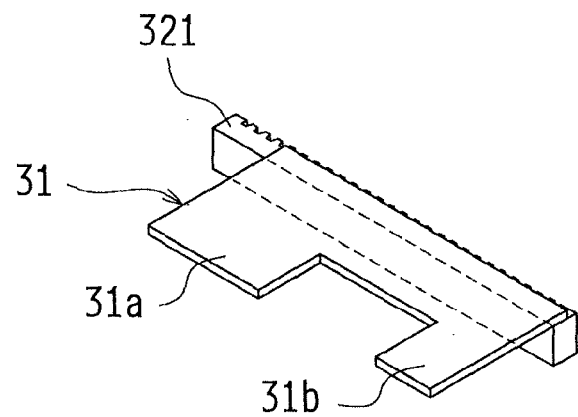
FIG. 9 is a perspective view of a roller slider in a roller movement mechanism.
Figure 10:
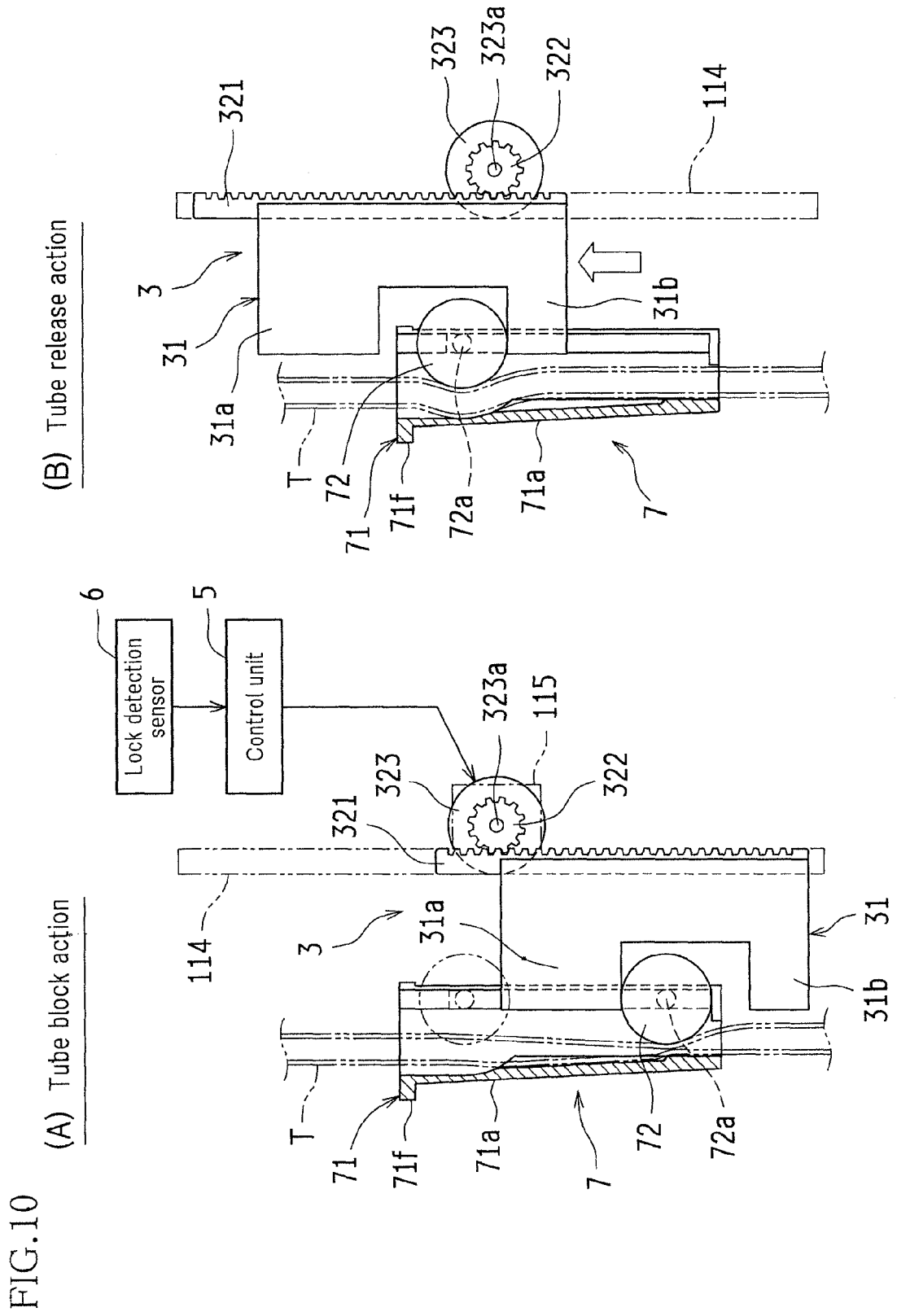
FIGS. 10(A) and 10(B) explain actions of the roller movement mechanism.

As shown in FIG. 9, the roller slider 31 is a plate-like member having a pair of pushing pieces (a block-side pushing piece 31a and a release-side pushing piece 31b) which are opposed to each other with a predetermined gap (a gap greater than the diameter of the roller 72 of the roller clamp 7). The roller slider 31 is oriented parallel to the front face of the pump body 11, and is integrally attached to the rack gear 321.

The roller slider 31 is positioned relative to the clamp holding recess 113 in the following manner. As shown in FIG. 5, FIG. 6, FIG. 10(A), etc., with the roller clamp 7 being held in the clamp holding recess 113, an edge of the block-side pushing piece 31a locates in a middle portion of a gap between the side walls 71a, 71b of the clamp body 71, and the roller 72 of the roller clamp 7 is caught between the block-side pushing piece 31a and the release-side pushing piece 31b. Owing to this positioning, when the roller slider 31 moves upwardly or downwardly, with the roller clamp 7 being held by the clamp holding recess 113, either the block-side pushing piece 31 or the release-side pushing piece 31b comes into contact with the outer periphery of the roller 72 of the roller clamp 7.

The rack gear 321 is slidably provided in a guide groove 114 formed in the front face of the pump body 11. The guide groove 114 extends vertically in the infusion pump 1, namely, in direction of movement by the roller 72 of the roller clamp 7 attached in the clamp holding recesses 113, 123. The rack gear 321 can vertically (in direction of movement by the roller 72) slide along the guide groove 114.

The rack gear 321 meshes with the pinion gear 322. The pinion gear 322 is mounted on a rotation shaft 323a of the electric motor 323 in an integrally rotatable manner. When the electric motor 323 rotates (clockwise in the drawings) to rotate the pinion gear 322, the rack gear 321 moves upwardly along the guide groove 114. By this upward movement, the roller slider 31 moves upwardly in the pump body 11 (toward the pump unit 112). When the electric motor 323 rotates in reverse (counterclockwise in the drawings) to rotate the pinion gear 322, the rack gear 321 moves downwardly along the guide groove 114. By this downward movement, the roller slider 31 moves downwardly in the pump body 11 (away from the pump unit 112). The electric motor 323 is accommodated inside the pump body 11. The rotation shaft 323a of the electric motor 323 is located at the front face side of the pump body 11 through an opening 115, and the pinion gear 322 is attached to the tip end of the rotation shaft 323a. The electric motor 323 is powered by a battery built in the infusion pump 1 or by a commercial power source.

The drive of the electric motor 323 is controlled by the control unit 5. The control unit 5 drives the electric motor 323 in accordance with a detection signal from the lock detection sensor 6.

To be specific, while the door 12 is open and the door lock mechanism 13 is in an unlocked state (when the lock detection sensor 6 produces an OFF signal), the roller slider 31 stays at the position shown in FIG. 5 and FIG. 6 (a tube block position). In this unlocked state, if the door lock mechanism 13 is manipulated to the locked position, the detection signal from the lock detection sensor 6 changes from an OFF signal to an ON signal. Then, the electric motor 323 is driven to move the roller slider 31 to the position shown in FIG. 7 and FIG. 8 (a tube release position). When the roller slider 31 reaches the tube release position, the electric motor 323 is stopped.

Further, in the state shown in FIG. 7 and FIG. 8, if the door lock mechanism 13 is manipulated to the unlocked position, the detection signal from the lock detection sensor 6 changes from an ON signal to an OFF signal. Then, the electric motor 323 is driven to move the roller slider 31 to the position shown in FIG. 5 and FIG. 6 (the tube block position). When the roller slider 31 reaches the tube block position, the electric motor 323 is stopped.

The stop operation for the electric motor 323 at the tube block position and the tube release position may be controlled based on the number of revolutions of the electric motor (a stepper motor) 323 or the motor-driving time (the energization time), or may be controlled with use of a limit switch or the like.

—Description of Operations—

The following description concerns a manner of setting the infusion tube T to the infusion pump 1, and the operation of the roller movement mechanism 3, referring to FIG. 2 to FIG. 11.

(1) First of all, in the infusion set S shown in FIG. 27, the roller 72 of the roller clamp 7 is manipulated to block the infusion tube T. Then, as shown in FIG. 2, while the door 12 of the infusion pump 1 is open, the roller clamp 7 is brought to the front face of the pump body 11, and the first side wall 71a of the roller clamp 7 is fitted into the clamp holding recess 113 of the pump body 11 (see FIG. 5 and FIG. 6). Specifically, the clamp body 71, with the flange 71f oriented to the top, is inserted from a side (the left side in FIG. 2) of the clamp holding recess 113 into the clamp holding recess 113, in such a manner that the edge of the block-side pushing piece 31a of the roller slider 31 is inserted in the gap between the pair of side walls 71a, 71b. At this time, if the infusion tube T is not blocked by the roller clamp 7 by mistake and the roller 72 stays at the release position (the movement end nearer to the flange 71f), the roller 72 interferes with the block-side pushing piece 31a of the roller slider 31 (see two-dot chain lines in FIG. 5 and FIG. 6), and the roller clamp 7 cannot be fitted into the clamp holding recess 113. This arrangement ensures that the infusion tube T is blocked without fail before the infusion tube T is attached to the infusion pump 1.

(2) With the roller clamp 7 being fitted in the clamp holding recess 113, the infusion tube T at the upstream side of the roller clamp 7 is attached to the tube attachment guide 111 and the pump unit 112. After the tube is attached in this manner, the door 12 is closed. Closure of the door 12 causes the second side wall 71b of the roller clamp 7 to be fitted into the clamp holding recess 123 of the door 12 (see FIG. 8). As a result, the roller clamp 7 can be securely held in the infusion pump 1.

Figure 3:
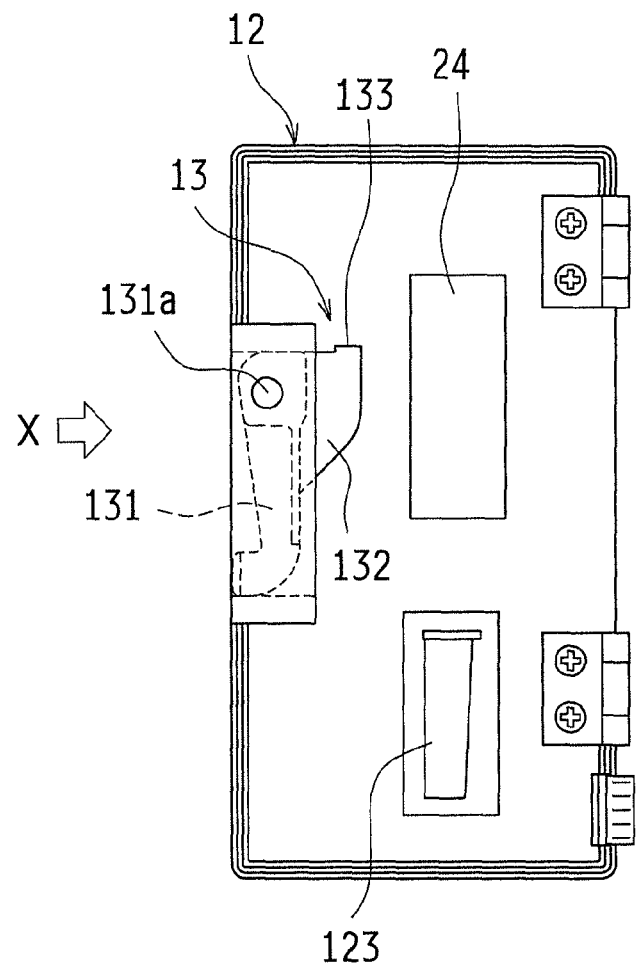
FIG. 3 illustrates the door shown in FIG. 2, with the lock lever being manipulated to a lock side.
Figure 4:
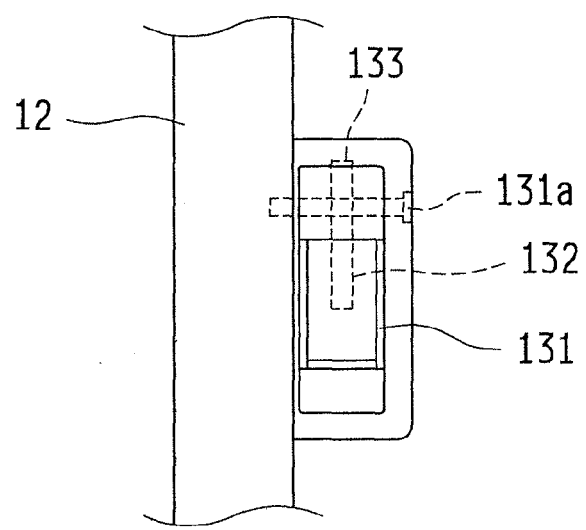
FIG. 4 is a view taken in the direction of Arrow X in FIG. 3.

(3) After the door 12 is closed, the lock lever 131 of the door lock mechanism 13 is turned inwardly of the lever housing recess 11a of the pump body 11 (turned by about 90 degrees) around the rotation shaft 131a. Inward turning of the lock lever 131 causes the lock piece 132 to rotate around the rotation shaft 131a, as shown in FIG. 3 and FIG. 7, until the lock latch 133 at the edge of the lock piece 132 is engaged with the engagement piece 134 of the pump body 11. As a result, the door 12 is kept closed (locked). In addition, at the moment when the lock latch 133 is engaged with the engagement piece 134 (when the lock latch 133 is located at the position of the lock detection sensor 6), the output signal from the lock detection sensor 6 changes from an OFF signal to an ON signal. In accordance with the change in the output signal (OFF to ON) from the lock detection sensor 6, the electric motor 323 of the roller movement mechanism 3 rotates (rotates clockwise), causing the roller slider 31 to move upwardly (toward the pump unit 112) from the position shown in FIG. 6 and FIG. 10(A) (the tube block position). With this upward movement of the roller slider 31, the release-side pushing piece 31b pushes the roller 72 toward the release-side movement end (the end nearer to the flange 71f) of the clamp body 71. When the roller 72 has reached the release-side movement end of the clamp body 71, the infusion tube T is completely released (FIG. 10(B)), and the electric motor 323 of the roller movement mechanism 3 is stopped at this moment. After the infusion tube is set in this manner, the infusion pump 1 is driven to prime the infusion set S. Alternatively, the infusion set S may be primed in advance by a pressure difference before the infusion tube is set to the infusion pump 1.

After the preparation of infusion treatment is completed by the above processes, the infusion pump 1 is driven to start a prescribed infusion treatment (drip infusion).

(4) When the cumulative time (or the cumulative dose) reaches a preset value after the infusion pump 1 started running, the infusion pump 1 is stopped. After the stop of the infusion pump 1 is confirmed, the lock lever 131 of the door lock mechanism 13 is turned to the near side (outwardly of the lever housing recess 11a) (or turned in an opposite direction from the door locking procedure). Outward turning of the lock lever 131 causes the lock piece 132 to turn, until the lock latch 133 is disengaged from the engagement piece 134 of the pump body 11. As a result, the door 12 is unlocked.

Figure 11:
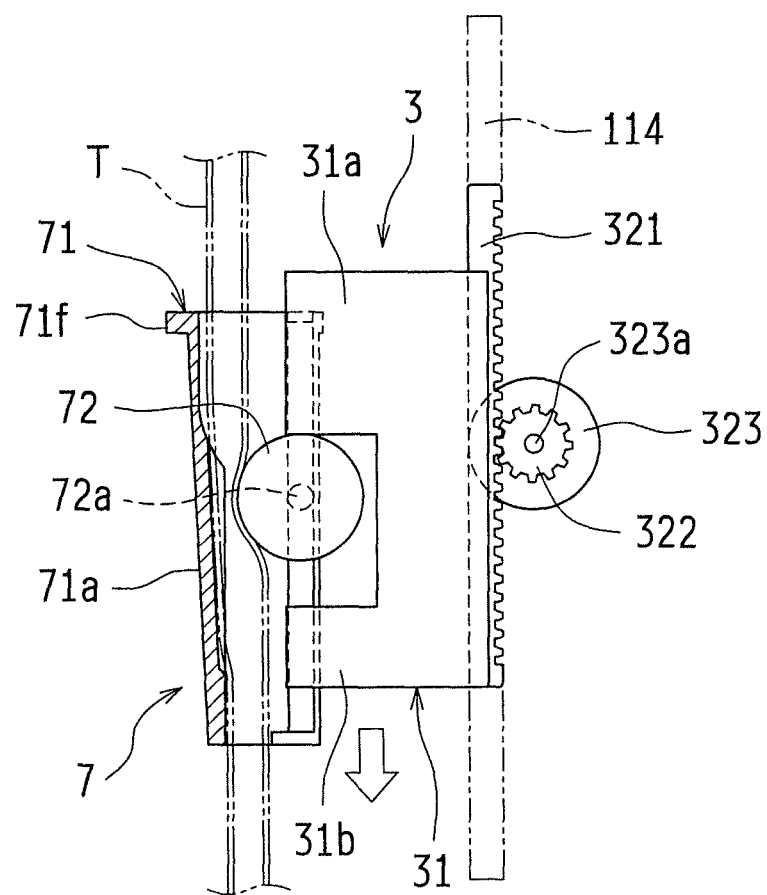
FIG. 11 explains an action of the roller movement mechanism.

When the lock latch 133 is disengaged from the engagement piece 134, the output signal from the lock detection sensor 6 changes from an ON signal to an OFF signal. In accordance with the change in the output signal (ON to OFF) from the lock detection sensor 6, the electric motor 323 of the roller movement mechanism 3 rotates in reverse to the rotation during the door locking procedure, causing the roller slider 31 to move downwardly (away from the pump unit 112) from the position shown in FIG. 8 and FIG. 10(B). During this downward movement of the roller slider 31, the block-side pushing piece 31a of the roller slider 31 comes into contact with the outer periphery of the roller 72, as shown in FIG. 11. From the moment of contact, the roller slider 31 pushes the roller 72 downwardly and rotationally toward the block-side movement end of the clamp body 71 (the opposite end to the flange 71f). When the roller 72 has reached the block-side movement end of the clamp body 71, the infusion tube T is completely blocked (FIG. 10(A)), and the electric motor 323 of the roller movement mechanism 3 is stopped at this moment. Thereafter, the door 12 is opened to remove the infusion tube T and the roller clamp 7 from the infusion pump 1.

As described above, the infusion pump 1 according to this example is configured to hold the roller clamp 7 in the pump body 11 and to include the roller movement mechanism 3 for moving the roller 72 of the roller clamp 7 in coordination with manipulation of the door lock mechanism 13. Specifically, when the door lock mechanism 13 is in the locked state, the roller 72 of the roller clamp 7 is configured to stay at the position to release the infusion tube T. On the other hand, when the door lock mechanism 13 is in the unlocked state, the roller 72 of the roller clamp 7 is configured to stay at the position to block the infusion tube T. Hence, even after the door 12 of the infusion pump is closed, the infusion tube T is kept blocked by the roller clamp 7 as far as the door 12 is unlocked. Eventually, the infusion pump 1 can reliably prevent free flow due to incomplete closure of the door 12 or failure to lock the door 12.

Further, when the door lock mechanism 13 is manipulated to open the closed door 12, this manipulation causes the roller clamp 7 to block the infusion tube T automatically. Therefore, the infusion pump in this example prevents free flow even if the door 12 opens accidentally during infusion treatment or in other situations. Furthermore, after infusion treatment, a user needs to manipulate the door lock mechanism 13 to the unlocked state before opening the door 12, so that the infusion tube T is blocked by the roller clamp 7 without fail. Eventually, the infusion pump in this example avoids a trouble of "removing the infusion tube T from the infusion pump 1, while a user forgets to block the infusion tube T by the roller clamp 7".

Additionally, the infusion pump according to the present invention can prevent free flow by holding the roller clamp 7 of the infusion tube T in the pump body 11, and thus does not require a special clamp. Therefore, this infusion pump can also prevent free flow when employed with a common infusion tube equipped with a roller clamp.

As described above, the infusion pump 1 in this example can reliably prevent free flow due to operational errors by health-care professionals such as nurses or due to some other causes.

In the above-described example, the lock detection sensor 6 (lock detection means) for detecting whether the door lock mechanism 13 is locked or not is a reflective photoelectric sensor composed of a light-emitting element and a light-receiving element. However, this is a non-limiting example, and the lock detection sensor 6 may be a through-beam sensor in which a light-emitting element and a light-receiving element are opposed to each other. In addition to these photoelectric sensors, for example, it is also possible to use other known position/object detection means such as a limit switch which switches on (or switches off) when the lock lever 131, the lock piece 132, and the others are turned to the locked position.

Figure 20:
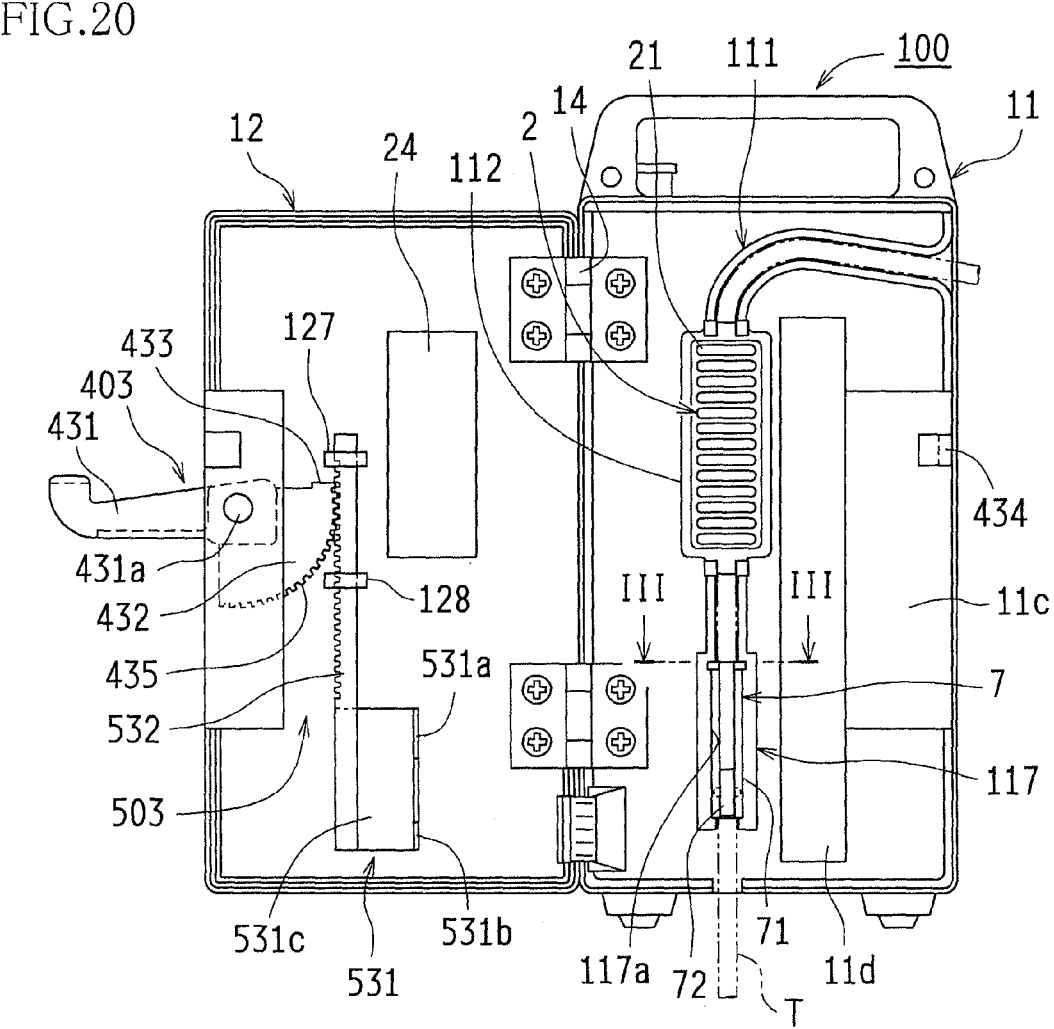
FIG. 20 shows a schematic configuration of another exemplary infusion pump according to the present invention, in a state where the door of the infusion pump is open and the roller clamp is held in the pump body.
Figure 21:
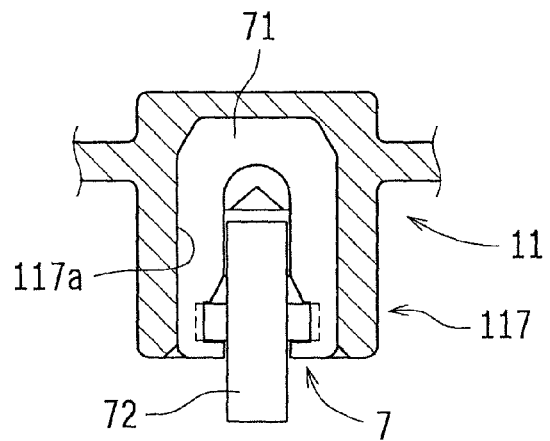
FIG. 21 is a cross-sectional view taken along the line III-III in FIG. 20.

In the above-described example, the roller clamp 7 is held by the pump body 11 in such an orientation that the rotation shafts 72a, 72b of the roller 72 extend vertically to the front face of the pump body 11. However, this is a non-limiting example, and the roller clamp 7 may be held by the pump body 11 in such an orientation as illustrated in FIG. 20 and FIG. 21.

In the above-described example, the roller movement mechanism is provided on the pump body 11, but alternatively may be provided on the door 12.

Embodiment 1-2

Hereinafter, another example of the roller movement mechanism is described with reference to FIG. 16. FIG. 16 shows only the roller slider 301 and omits other components of the roller movement mechanism. Except the arrangements to be described below, Embodiment 1-2 is similar to Embodiment 1-1, and hence detailed description of similar elements is omitted.

The roller slider 301 in this example is characterized in that the distance D between the block-side pushing piece 301a and the release-side pushing piece 301b is greater than the length L of the clamp body 71 of the roller clamp 7.

In this example, while the door 12 of the infusion pump 1 is open, the roller clamp 7 stays at an origin position as shown in FIG. 16(A). The origin position in this context means a position at which the clamp body 71 of the roller clamp 7 held in the clamp holding recess 113 (shown in FIG. 2) stays in a gap between the block-side pushing piece 301a and the release-side pushing piece 301b. Therefore, while the door 12 is open, the roller clamp 7 can be fitted into the clamp holding recess 113, irrespective of the position of the roller 72, namely, irrespective of whether the roller 72 of the roller clamp 7 is located at a tube block position (the block-side movement end) as shown in FIG. 16(A-1) or at a tube release position (release-side movement end) as shown in FIG. 16(A-2).

The roller slider 301 is attached to the rack gear 321 of the roller movement mechanism 3 which has a similar structure to the one employed in Embodiment 1-1. When the door 12 of the infusion pump 1 is closed and the lock lever 131 of the door lock mechanism 13 is manipulated to the locked position, the roller slider 301 is caused to move upwardly (toward the tube releasing-side). During this upward movement, the release-side pushing piece 301b comes into contact with the outer periphery of the roller 72. From the moment of contact, the roller slider 301 pushes the roller 72 upwardly and rotationally toward the release-side movement end of the clamp body 71 (the opposite end to the flange 71f). When the roller 72 has reached the release-side movement end of the clamp body 71 (the end nearer to the flange 71f), the infusion tube T is completely released (FIG. 16(B)).

Further, when the lock lever 131 is manipulated to the unlocked position to unlock the closed door 12, the roller slider 301 is caused to move downwardly (toward the tube block-side) from the state shown in FIG. 16(B). During this downward movement, the block-side pushing piece 301a comes into contact with the outer periphery of the roller 72. From the moment of contact, the roller slider 301 pushes the roller 72 downwardly and rotationally toward the block-side movement end of the clamp body 71 (the end nearer to the flange 71f). When the roller 72 has reached the block-side movement end (the end nearer to the flange 71f) of the clamp body 71, the infusion tube T is completely blocked (FIG. 16(C)). Thereafter, the roller slider 301 returns to the origin position as shown in FIG. 16(A).

Also in this example, the roller clamp 7 is configured to be held by in the pump body 11 and to move in coordination with manipulation of the lock lever 131 of the door lock mechanism 13. Specifically, when the door lock mechanism 13 is in the locked state, the roller 72 of the roller clamp 7 is configured to stay at the position to release the infusion tube T. On the other hand, when the door lock mechanism 13 is in the unlocked state, the roller 72 of the roller clamp 7 configured to stay at the position to block the infusion tube T. This example can also reliably prevent free flow due to operational errors by health-care professionals such as nurses or due to some other causes.

Embodiment 1-3

Another example of an infusion pump according to the present invention is described with reference to FIG. 17 to FIG. 26.

Similar to Embodiment 1-1 described above, an infusion pump 100 in this example is a peristaltic finger infusion pump, and is equipped with a pump body (a casing) 11, and a door 12 which closes on a front face (a tube attachment position) of the pump body 11. The door 12 is swingably held on the pump body 11 by hinges 14, 14, and is capable of swinging between a fully closed position and a fully open position (for example, a 180-degree open position) with respect to the front face of the pump body 11.

Except the arrangements to be described below, the infusion pump 100 in this example is similar to the one described in Embodiment 1-1, and hence detailed description of similar elements is omitted.

—Pump Body—

Also in this example, the pump body 11 is provided with a tube attachment guide 111 and a pump unit 112 at a substantially central part thereof (a widthwise central part). A clamp holding part 117 is provided downstream of the pump unit 112. The clamp holding part 117 has a holding recess 117a into which the clamp body 71 of the roller clamp 7 shown in FIG. 28 to FIG. 30 can be fitted from the bottom plate 71c. With the roller clamp 7 (the clamp body 71) being fitted in the holding recess 117a, the infusion tube T is arranged vertically in the infusion pump 100, and can be released and blocked by vertical movements of the roller 72.

The pump body 11 is further provided with, at a side thereof, a lever housing recess 11c which can accommodate a lock lever 431 of a door lock mechanism 403 to be described later. Provided at an upper part of the lever housing recess 11c is an engagement piece (a hook-shaped member having an L-shaped cross section) 434 for engaging with a lock latch 433 of a lock piece 432 of the door lock mechanism 403. In addition, the pump body 11 is provided with a step 11d for avoiding interference with a rack gear 532 or the other elements of the roller movement mechanism 503 to be described later.

—Door Lock Mechanism—

Next, the door lock mechanism is described with reference to FIG. 17 to FIG. 22.

Figure 17:
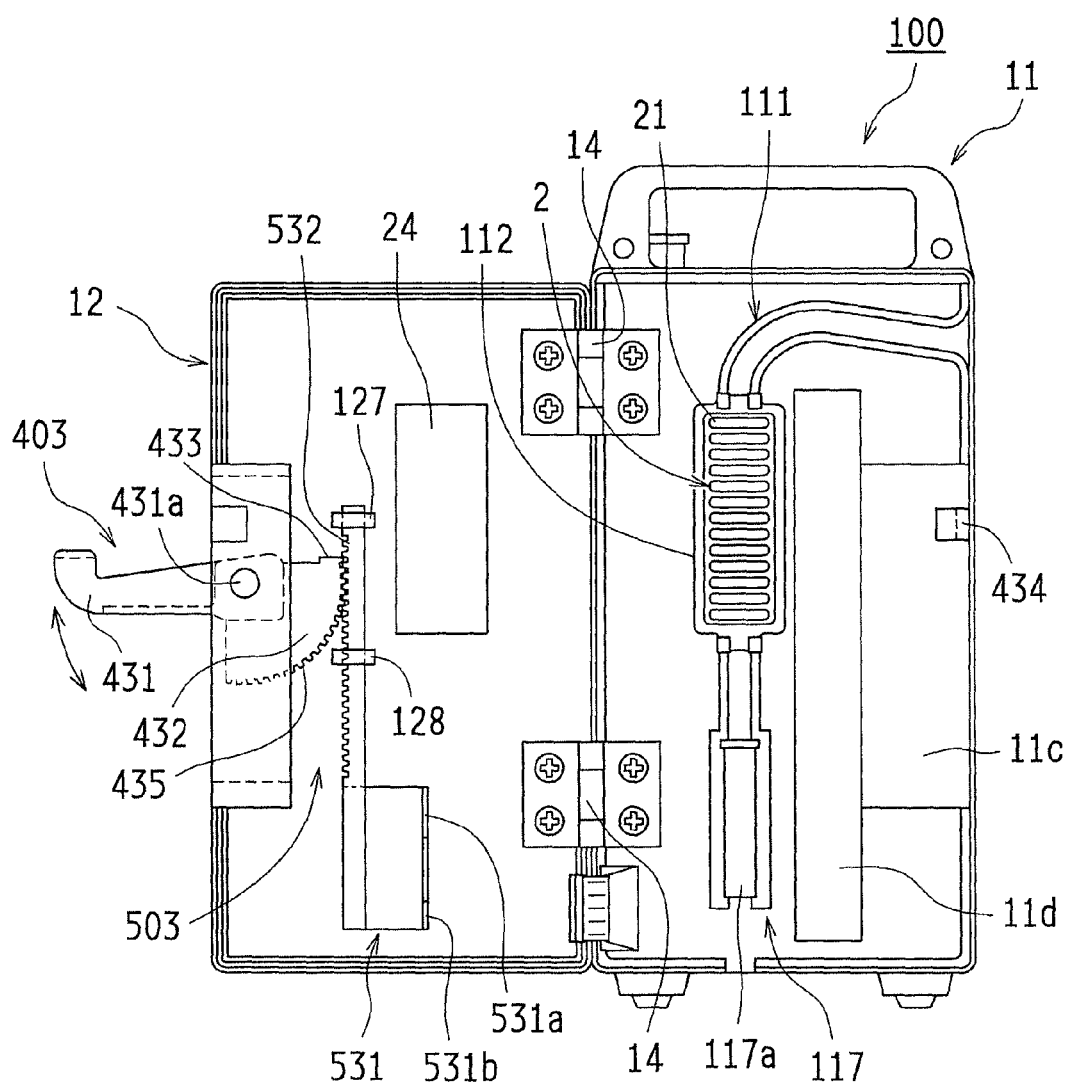
FIG. 17 shows a schematic configuration of another exemplary infusion pump according to the present invention, in a state where the door of the infusion pump is open.

A lock lever 431 is provided at a side end of the door 12 (an end opposite to the hinges 14). The lock lever 431 can turn around a rotation shaft 431a, and swingable (for example, swingable by about 90 degrees) between a lock release position (an unlocked position) as shown in FIG. 17 and a locked position for locking the door 12 (a position shown in FIG. 18 and FIG. 22). The lock lever 431 is integrally formed with a lock piece 432.

The lock piece 432 is a generally quarter-circular member, having a lock latch 433 at an end of an outer circumference thereof. When the lock lever 431 is manipulated to the locked position, the lock piece 432 and the lock latch 433 engage with the above-mentioned engagement piece 434 in the pump body 11, thereby keeping the door 12 fully closed. Additionally, an arc-like gear 435 is formed at the outer circumference of the lock piece 432, and is rotatable around an axial core of the rotation shaft 431a. The arc-like gear 435 meshes with a rack gear 532 of a roller movement mechanism 503 to be described later. The lock lever 431, the lock piece 432, and the lock latch 433 in the door 12, and the engagement piece 434 in the pump body 11 constitute a door lock mechanism 403. The door lock mechanism 403 can be located at the locked position or the unlocked position by manipulation of the lock lever 431.

—Roller Movement Mechanism—

Next, a roller movement mechanism 503 is described with reference to FIG. 17 to FIG. 26.

A roller movement mechanism 503 in this example is a mechanism for moving the roller 72 of the roller clamp 7 between a block position and a release position for the infusion tube T, while the roller clamp 7 is held in the clamp holding part 117 of the pump body 11.

The roller movement mechanism 503 is composed of a roller slider 531 and a rack gear 532 as well as the lock lever 431 and the lock piece 432 (the arc-like gear 435) of the door lock mechanism 403. In addition, the rack gear 532, the lock piece 432 (the arc-like gear 435) and the others constitute a manipulation force transmission mechanism (a mechanism for converting a manipulation force for turning the lock lever 431 into a force for moving the roller 72 of the roller clamp 7 and transmitting the converted force).

Figure 23:
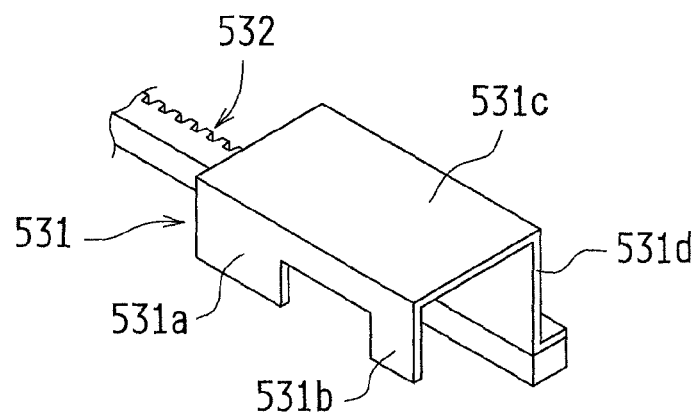
FIG. 23 is a perspective view of a roller slider in a roller movement mechanism.

As shown in FIG. 23, the roller slider 531 is a single-piece member composed of a longitudinal piece 531d integrally attached to the rack gear 532, a transverse piece 531c extending laterally (parallel to the inner face of the door 12) from an edge of the longitudinal piece 531d, and a block-side pushing piece 531a and a release-side pushing piece 531b each extending from an edge of the transverse piece 531c, orthogonally to the inner face of the door 12.

The block-side pushing piece 531a and the release-side pushing piece 531b of the roller slider 531 are positioned along the vertical direction of the door 12. The gap between the block-side pushing piece 531a and the release-side pushing piece 531b is set greater than the diameter of the roller 72 of the roller clamp 7. The positions of the block-side pushing piece 531a and the release-side pushing piece 531b of the roller slider 531 correspond to the position of the above-mentioned holding recess 117a of the clamp holding part 117 in the pump body 11. Due to this positioning, when the door 12 is closed, an edge of the block-side pushing piece 531a and an edge of the release-side pushing piece 531b partially enter a middle part of the holding recess 117a of the clamp holding part 117.

The rack gear 532 is positioned along the vertical direction of the door 12, and is held in a vertically slidable manner by support guides 127, 128 provided at the inner face of the door 12. As described above, the rack gear 532 is in mesh with the arc-like gear 435 of the lock piece 432 in the door lock mechanism 403. When the lock lever 431 of the door lock mechanism 403 is in the open state (the unlocked state) as shown in FIG. 20, the rack gear 532 (the roller slider 531) stays at the bottommost end. In this state, if the lock lever 431 is manipulated to the lock side to bring the lock latch 433 of the lock piece 432 into engagement with the engagement piece 434 of the pump body 11 (the door locked state), the rack gear 532 (the roller slider 531) moves to the uppermost end (the position shown in FIG. 18 and FIG. 22).

As described already, if the door 12 is closed while the lock lever 431 in the open state and the roller slider 531 stays at the bottommost end, the edge of the block-side pushing piece 531a and the edge of the release-side pushing piece 531b partially enter the holding recess 117a of the clamp holding part 117 in the pump body 11. At this moment, if the roller 72 of the roller clamp 7 held by the clamp holding part 117 stays at the block-side movement end (the opposite end from the flange 71f), the roller 72 gets into a gap between the block-side pushing piece 531a and the release-side pushing piece 531b of the roller slider 531 (see FIG. 24(A)). On the other hand, if the roller 72 of the roller clamp 7 stays at the release-side movement end (the end nearer to the flange 71f), the block-side pushing piece 531a interferes with the roller 72, so that the door 12 cannot be closed.

—Description of Operations—

The following description concerns a manner of setting the infusion tube T to the infusion pump 1, and the operation of the roller movement mechanism 503, referring to FIG. 17 to FIG. 26.

(11) First of all, in the infusion set S shown in FIG. 27, the roller 72 of the roller clamp 7 is manipulated to block the infusion tube T. Then, as shown in FIG. 17, while the door 12 of the infusion pump 100 is open, the roller clamp 7 is brought to the front face of the pump body 11, and the clamp body 71 of the roller clamp 7 is fitted into the clamp holding recess 117a of the pump body 11, with the flange 71f being oriented to the top (see FIG. 20 and FIG. 21).

(12) With the roller clamp 7 being fitted in the holding recess 117a of the pump body 11, the infusion tube T at the upstream side of the roller clamp 7 is attached to the tube attachment guide 111 and the pump unit 112. After the tube is attached in this manner, the door 12 is closed.

Once the door 12 is closed, the edge of the block-side pushing piece 531a of the roller slider 531 in the roller movement mechanism 503 gets into the gap between the pair of side walls 71a, 71b of the clamp body 71. Thereby, the roller 72 of the roller clamp 7 stays between the block-side pushing piece 531a and the release-side pushing piece 531b (FIG. 24(A) and FIG. 25(A)).

As described above, in the case where the infusion tube T is not blocked by the roller clamp 7, the door 12 cannot be closed because the roller 72 interferes with the block-side pushing piece 531a of the roller slider 531 (see two-dot chain lines in FIG. 24(A) and FIG. 25(A)). In this manner, it is possible to prevent the infusion tube T from being left released before the infusion tube T is attached to the infusion pump 100.

Figure 18:
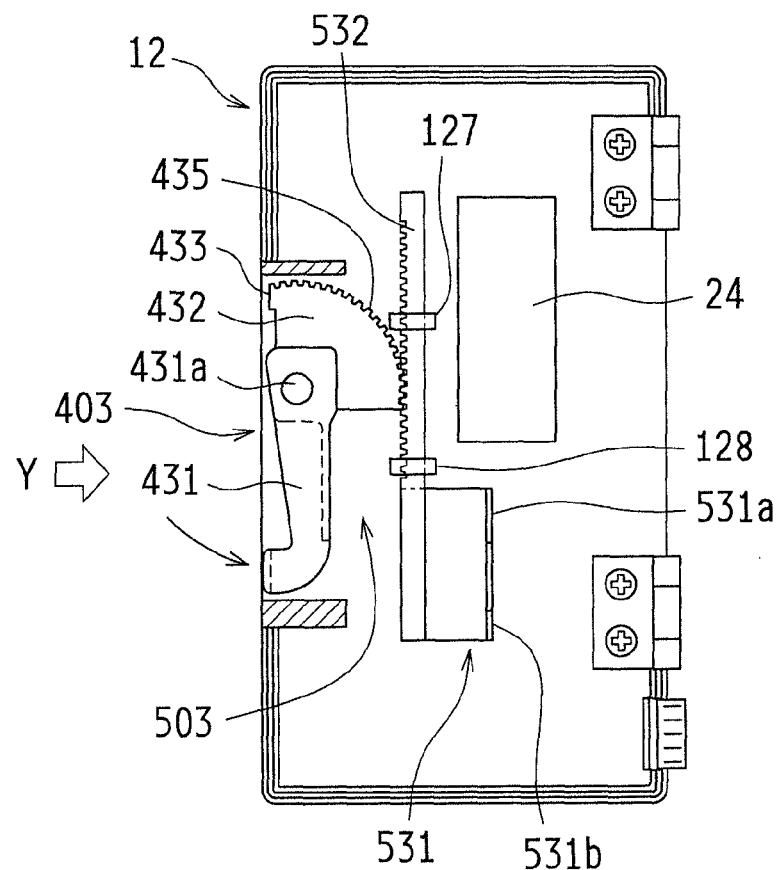
FIG. 18 illustrates the door shown in FIG. 17, with the lock lever being manipulated to a lock side.
Figure 19:
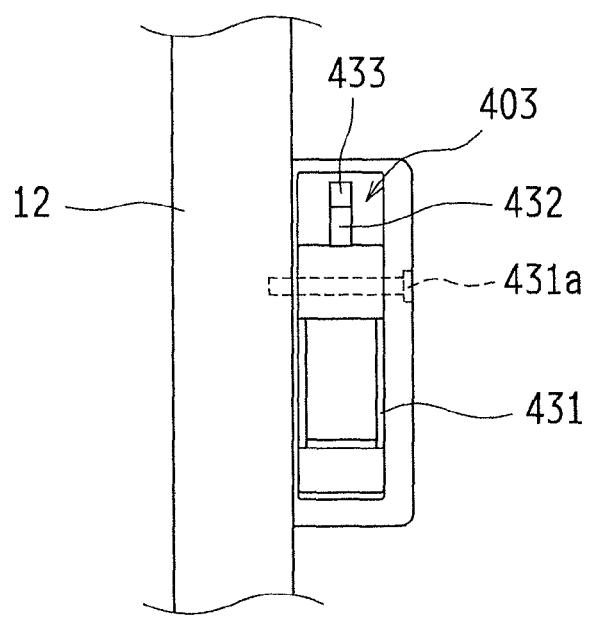
FIG. 19 is a view taken in the direction of Arrow Y in FIG. 18.
Figure 22:
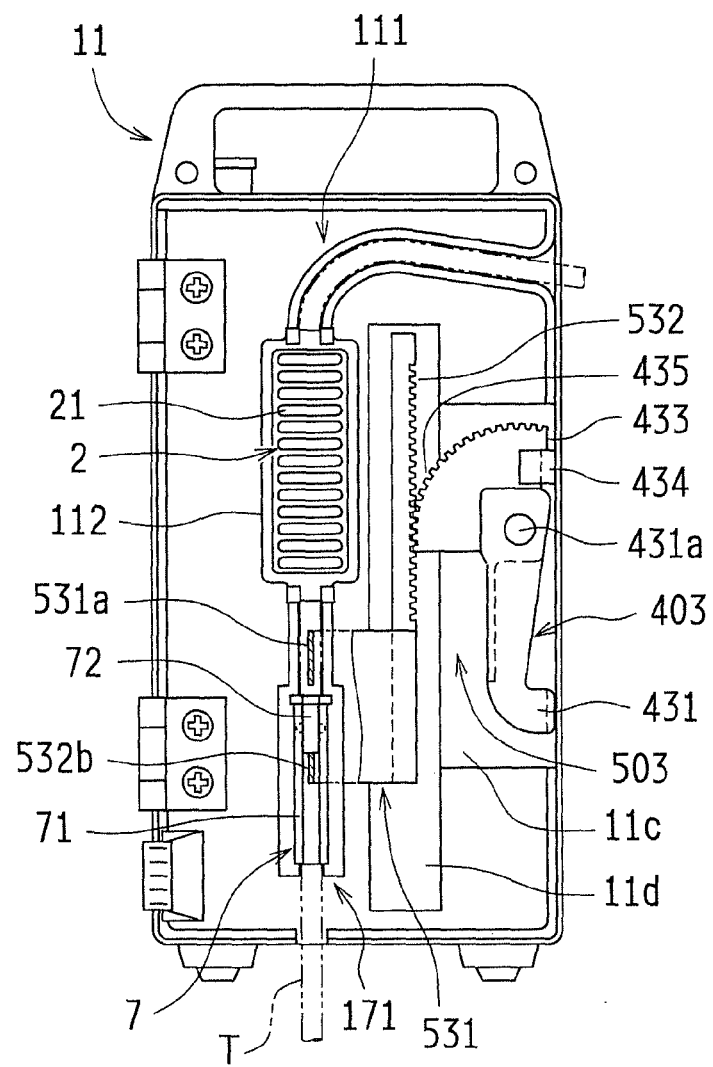
FIG. 22 is a schematic configuration of another exemplary infusion pump according to the present invention, in a state where the door (omitted in this figure) of the infusion pump is closed from the state shown in FIG. 20.

(13) After the door 12 is closed, the lock lever 431 of the door lock mechanism 403 is turned inwardly of the lever housing recess 11c of the pump body 11 (turned by about 90 degrees) around the rotation shaft 431a. Inward turning of the lock lever 431 causes the lock piece 432 to turn around the rotation shaft 431a, as shown in FIG. 18 and FIG. 22, until the lock piece 432 and the lock latch 433 at the edge of the lock piece 432 are engaged with the engagement piece 434 of the pump body 11. As a result, the door 12 is kept closed (locked). Besides, turning of the lock piece 432 around the rotation shaft 431a causes upward movement of the rack gear 532 which is in mesh with the arc-like gear 435 of the lock piece 432, followed by upward movement of the roller slider 531. With this upward movement of the roller slider 531, the release-side pushing piece 531b pushes the roller 72 toward the release-side movement end (the end nearer to the flange 71f) of the clamp body 71. When the roller 72 has reached the release-side movement end of the clamp body 71, the infusion tube T is completely released (FIG. 24(B) and FIG. 25(B)). After the infusion tube is set in this manner, the infusion pump 100 is driven to prime the infusion set S. Alternatively, the infusion set S may be primed in advance by a pressure difference before the infusion tube is set to the infusion pump 100.

After the preparation of infusion treatment is completed by the above processes, the infusion pump 100 is driven to start a prescribed infusion treatment (drip infusion).

Figure 26:
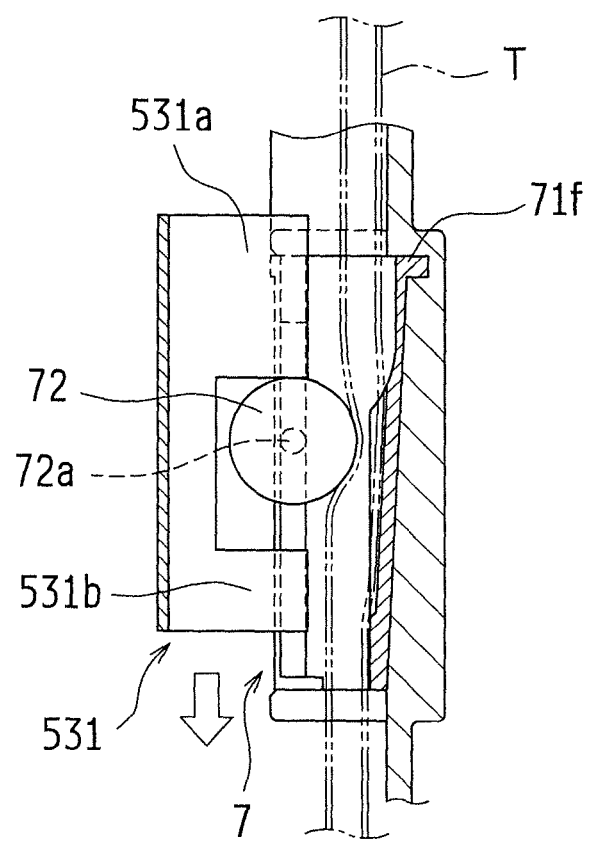
FIG. 26 explains an action of the roller movement mechanism.

(14) When the cumulative time (or the cumulative dose) reaches a preset value after the infusion pump 100 started running, the infusion pump 100 is stopped. After the stop of the infusion pump 100 is confirmed, the lock lever 431 of the door lock mechanism 403 is turned to the near side (outwardly of the lever housing recess 11c) (or turned in an opposite direction from the door locking procedure). Outward turning of the lock lever 431 causes the lock piece 432 to turn, until the lock piece 432 and the lock latch 433 are disengaged from the engagement piece 434 of the pump body 11. Besides, turning of the lock piece 432 causes the rack gear 532, namely, the roller slider 531, to move downwardly from the position shown in FIG. 24(B) and FIG. 25(B). During this downward movement of the roller slider 531, the block-side pushing piece 531a of the roller slider 531 comes into contact with the outer periphery of the roller clamp 7, as shown in FIG. 26. From the moment of contact, the roller slider 531 pushes the roller 72 downwardly and rotationally toward the block-side movement end of the clamp body 71 (the opposite end to the flange 71f). When the lock lever 431 is turned back to the position shown in FIG. 17, the roller 72 reaches the block-side movement end of the clamp body 71, so that the infusion tube T is completely blocked (FIG. 24(A)). Thereafter, the door 12 is opened to remove the infusion tube T and the roller clamp 7 from the infusion pump 100.

As described above, the infusion pump 100 according to this example is configured to hold the roller clamp 7 in the pump body 11 and to include the roller movement mechanism 503 for moving the roller 72 of the roller clamp 7 in coordination with manipulation of the lock lever 431 of the door lock mechanism 403. Specifically, when the door lock mechanism 403 is in the locked state, the roller 72 of the roller clamp 7 is configured to stay at the position to release the infusion tube T. On the other hand, when the door lock mechanism 403 is in the unlocked state, the roller 72 of the roller clamp 7 is configured to stay at the position to block the infusion tube T. Hence, even after the door 12 of the infusion pump is closed, the infusion tube T is kept blocked by the roller clamp 7 as far as the door 12 is unlocked. Eventually, the infusion pump 100 can reliably prevent free flow due to incomplete closure of the door 12 or failure to lock the door 12.

Further, when the door lock mechanism 403 is manipulated to open the closed door 12, this manipulation causes the roller clamp 7 to block the infusion tube T automatically. Therefore, the infusion pump in this example prevents free flow even if the door 12 opens accidentally during infusion treatment or in other situations. Furthermore, after infusion treatment, a user needs to manipulate the door lock mechanism 403 to the unlocked state before opening the door 12, so that the infusion tube T is blocked by the roller clamp 7 without fail. Eventually, the infusion pump in this example avoids a trouble of "removing the infusion tube T from the infusion pump 100, while a user forgets to block the infusion tube T by the roller clamp 7".

Additionally, the infusion pump according to the present invention can prevent free flow by holding the roller clamp 7 of the infusion tube T in the pump body 11, and thus does not require a special clamp. Therefore, this infusion pump can also prevent free flow when employed with a common infusion tube equipped with a roller clamp.

As described above, the infusion pump 100 according to this example can reliably prevent free flow due to operational errors by health-care professionals such as nurses or due to some other causes.

In this example, the roller clamp 7 is held by the pump body 11 in such an orientation that the rotation shafts 72a, 72b of the roller 72 extend parallel to the front face of the pump body 11. However, this is a non-limiting example, and the roller clamp 7 may be held by the pump body 11 in such an orientation as illustrated in FIG. 5 and FIG. 6.

In the above-described example, the roller movement mechanism is provided on the door 12, but alternatively may be provided on the pump body 11.

Embodiment 2-1

The following description is directed to yet another example of the infusion pump according to the present invention.

To start with, an infusion set for infusion treatment according to this example is described with reference to FIG. 46.

Figure 46:
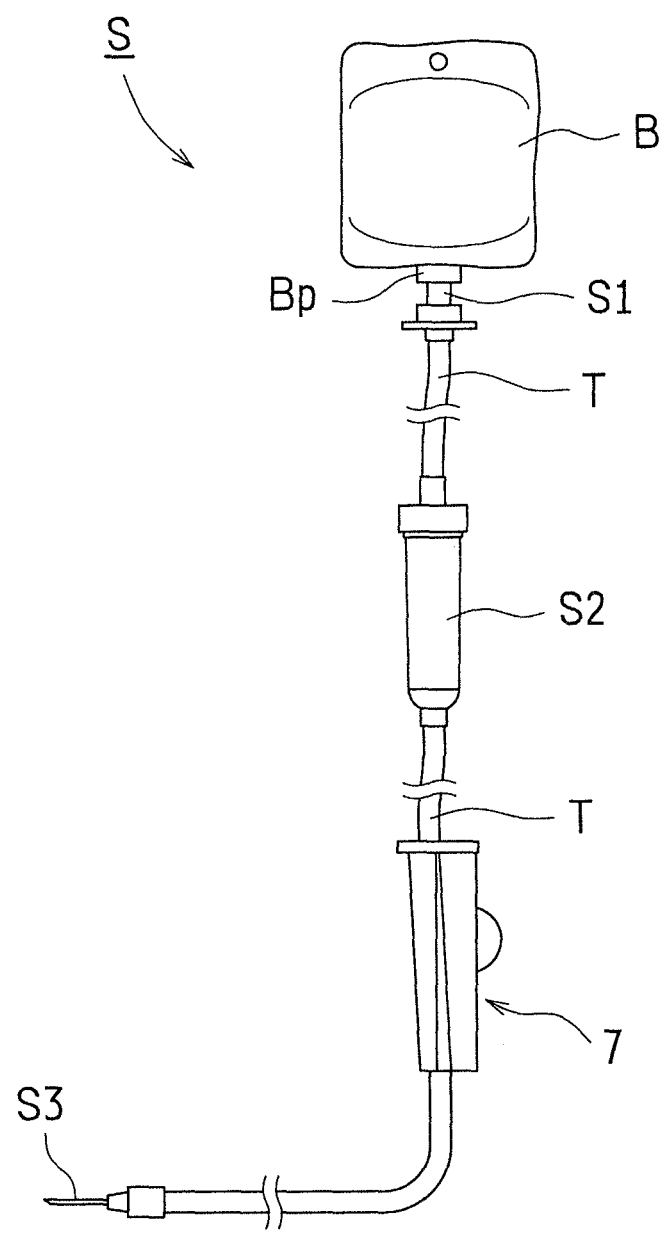
FIG. 46 shows a schematic configuration of an infusion set.

An infusion set S shown in FIG. 46 is similar to the one described in Embodiment 1-1 above, and is composed of an infusion bag B containing a drug solution, a spike S1 to be inserted in a port Bp of the infusion bag B, a drip chamber S2 for visually inspecting the flow rate of the infusion liquid, an upstream infusion tube T for connecting the spike S1 and the drip chamber S2, a downstream infusion tube T connected to the drip chamber S2, a roller clamp 7 provided along the downstream infusion tube T, and a needle (an intravenous needle) S3 connected to a patient's end of the infusion tube T.

Figure 47:
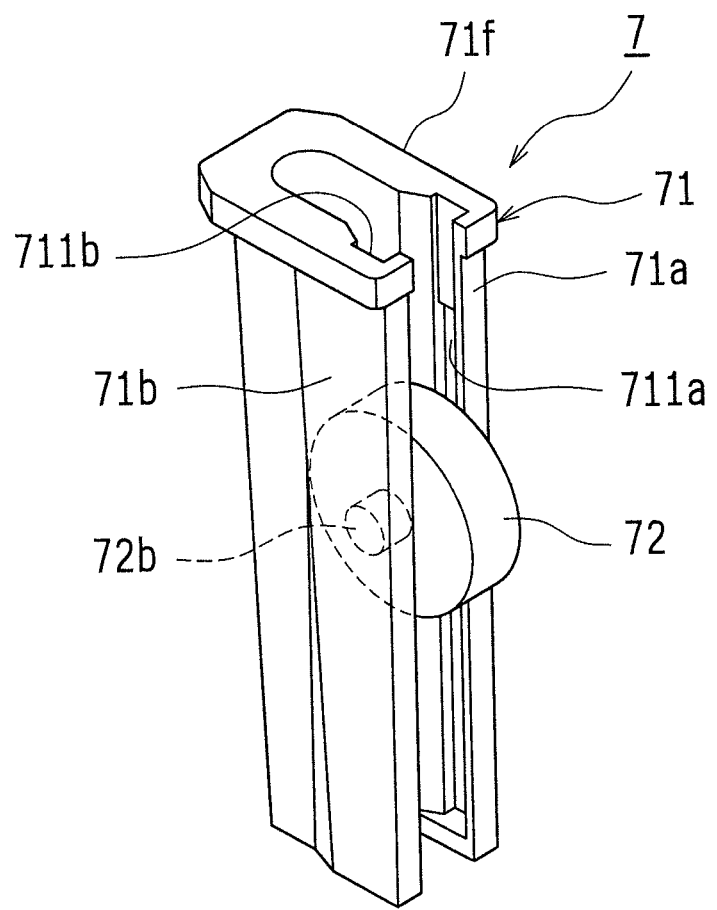
FIG. 47 is a perspective view of a roller clamp.
Figure 48:
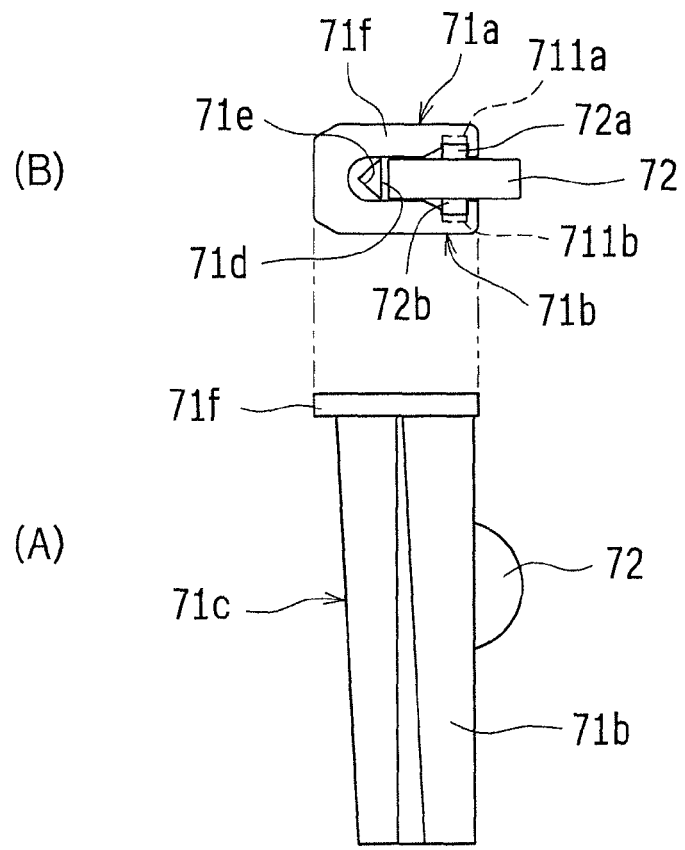
FIG. 48(A) is a side view of the roller clamp.
FIG. 48(B) is a plan view thereof, with the two views being laid out together.
Figure 49:
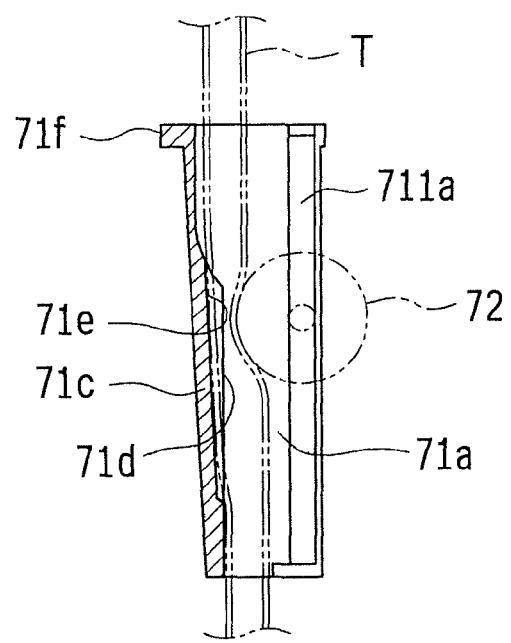
FIG. 49 is a cross-sectional view of the roller clamp.

As illustrated in FIG. 47 to FIG. 49, the roller clamp 7 is composed of a clamp body 71 and a roller 72. The clamp body 71 is a single-piece resin-molded member composed of a pair of side walls 71a, 71b opposed to each other at a predetermined gap, and a bottom plate 71c. In inner surfaces of the side walls 71a, 71b, guide grooves 711a, 711b are provided in order to hold and guide rotation shafts 72a, 72b of the roller 72. A bottom surface 71d (a top surface of the bottom plate 71c) of the clamp body 71 is provided with a V-shaped groove 71e. The bottom surface 71d of the clamp body 71 is inclined relative to the guide grooves 711a, 711b, in such a manner that a distance between the guide grooves 711a, 711b and the bottom surface 71d decreases from one end of the clamp body 71 (an end nearer to the flange 71f) to the other end thereof.

The roller 72 is rotationally movable along the guide grooves 711a, 711b, between one end of the clamp body 71 (the end nearer to the flange 71f) and the other end thereof (the opposite end from the flange 71f). When the roller 72 stays at the movement end nearer to the flange 71f (a release-side movement end), the gap between the outer periphery of the roller 72 and the bottom surface 71d of the clamp body 71 is at the maximum. On the other hand, when the roller 72 stays at the movement end opposite to the flange 71f (a block-side movement end), the gap between the outer periphery of the roller 72 and the bottom surface 71d of the clamp body 71 is at the minimum.

In the roller clamp 7 of this structure, the infusion tube T is blocked and released in the following manner. With the infusion tube T inserted between the bottom surface 71d of the clamp body 71 and the outer periphery of the roller 72, the roller 72 is rotated to the block-side movement end of the clamp body 71 to close the infusion tube T completely. From this state, while the roller 72 is rotated toward the flange 71f of the clamp body 71, the rotational movement of the roller 72 causes a gradual decrease in the degree of pressing (flattening) the infusion tube T and an eventual increase in the amount of infusion liquid allowed to flow through the infusion tube T. When the roller 72 has reached the release-side movement end, the infusion tube T is no longer pressed by the roller 72 (the infusion tube T is fully released).

—Infusion Pump—

An infusion pump according to this example is described with reference to FIG. 31 to FIG. 45.

An infusion pump 2001 in this example is a peristaltic finger infusion pump, and is equipped with a pump body (a casing) 2011, and a door 2012 which closes on a front face (a tube attachment position) of the pump body 2011. The door 2012 is held swingably (in a freely turning manner) on the pump body 2011 by hinges 2014, 2014, and is capable of swinging between a fully closed position and a fully open position (for example, a 180-degree open position) with respect to the front face of the pump body 2011.

At the front face of the pump body 2011, there are provided a tube attachment guide 2111, a pump unit 2112 which is connected to the tube attachment guide 2111 and which has an enlarged rectangular shape, and a clamp holding part 2113, in this order from the upstream side in an infusion liquid feed direction. The groove width of the tube attachment guide 2111 corresponds to an outer diameter of the infusion tube T of the above-mentioned infusion set. Tips of fingers 21 . . . 21 in the pump mechanism 2 (to be described later) are located in the pump unit 2112. The tube attachment guide 2111 has a transversely curved (bent) shape.

The door 2012 is further provided with a pressing plate 24 at an inner face thereof. The pressing plate 24 is positioned to face the tips of the fingers 21 . . . 21 in the pump mechanism 2 while the door 2012 is closed.

The clamp holding part 2113 has a holding recess 2113a in which the clamp body 71 of the roller clamp 7 as shown in FIG. 46 to FIG. 49 can be fitted from a bottom plate 71c thereof. With the roller clamp 7 (the clamp body 71) being fitted in the holding recess 2113a, the infusion tube T is arranged vertically in the infusion pump 2001, and can be released and blocked by vertical movements of the roller 72.

A side end (an opposite end from the hinges 2014) of the pump body 2011 is provided with a lock recess 2011a into which an engagement member 2121 of a door lock mechanism 2005 to be described later can be accommodated. A rectangular slit-like through hole 2110b is formed in a vertical wall (a closed end wall of the recess) 2110a of the lock recess 2011a (see FIG. 36 to FIG. 39). Through this through hole 2110b, a lock piece 2051 of a lock lever 2005A to be described later can project outwardly of the pump body 2011 (into the lock recess 2011a).

Figure 31:
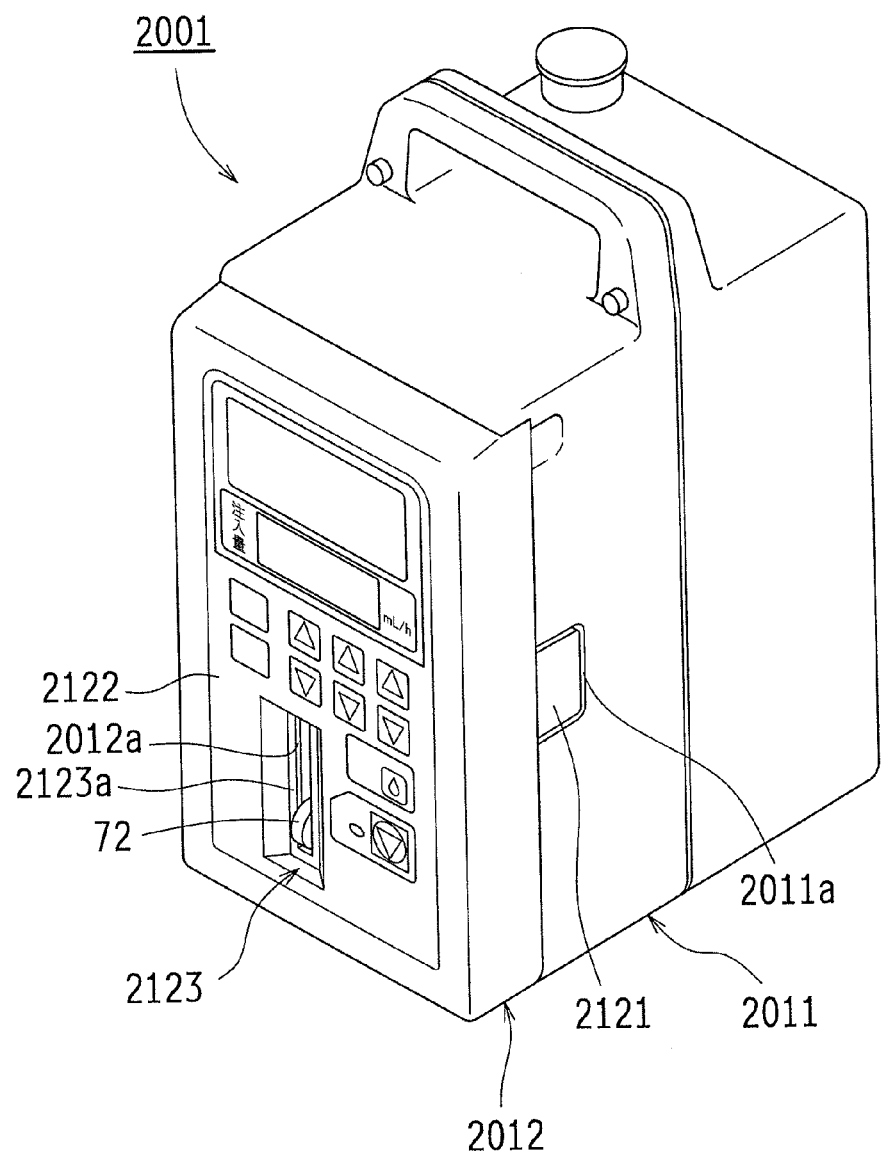
FIG. 31 is a perspective view showing an external appearance of yet another exemplary infusion pump according to the present invention.
Figure 38:
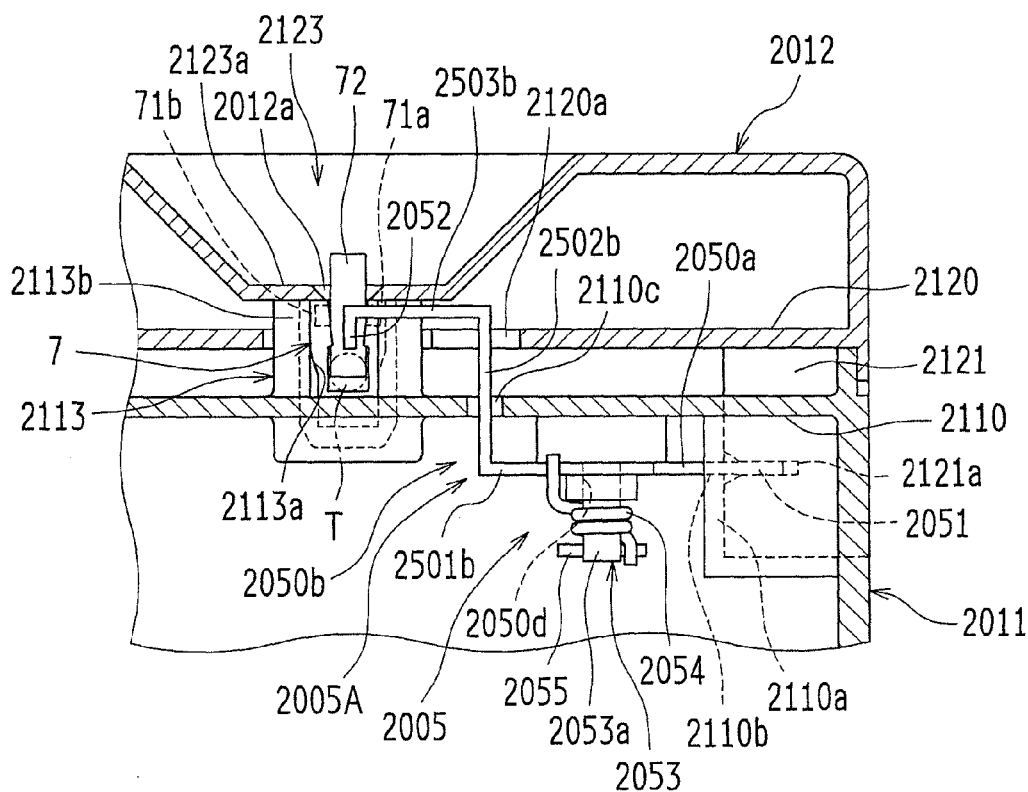
FIG. 38 is a cross-sectional view taken along the line V-V in FIG. 37.
Figure 39:
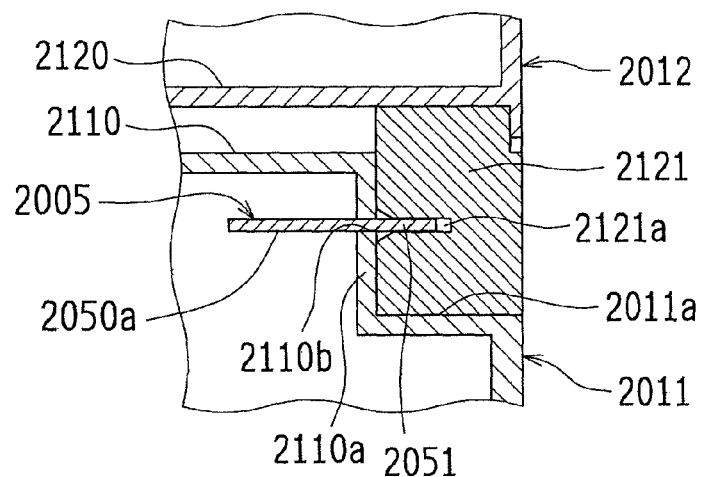
FIG. 39 is a cross-sectional view taken along the line VI-VI in FIG. 37.
Figure 41:
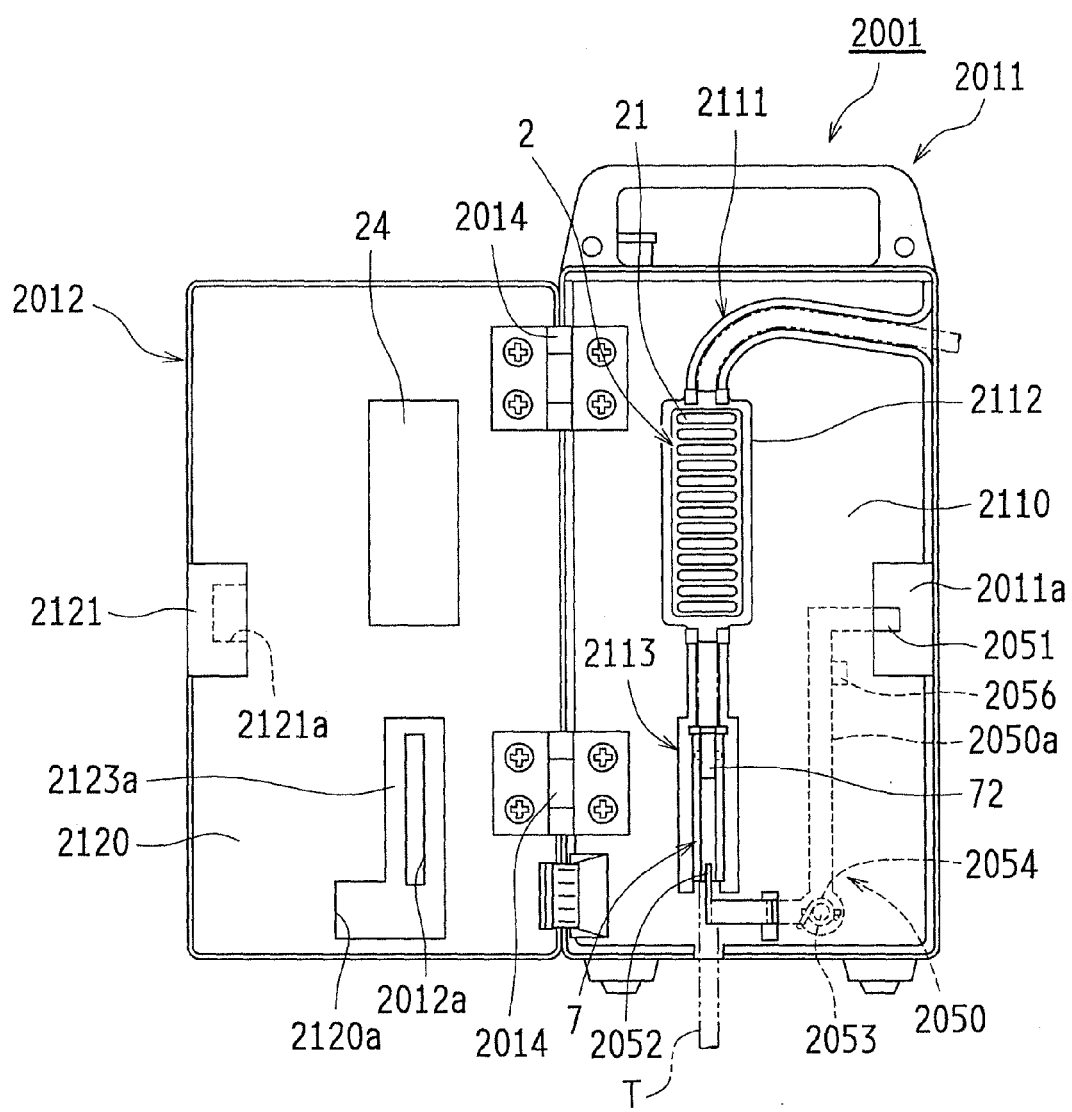
FIG. 41 shows a state where the door of the infusion pump is open and the roller clamp held in the clamp holding part is not blocked.

The door 2012 is provided with an operation recess 2123 at a position corresponding to the clamp holding part 2113 (at a position opposed to the clamp holding part 2113 while the door 2012 is closed) (see FIG. 31, FIG. 38, etc.). While the door 2012 is closed, a vertical wall (a wall parallel to the front face of the door) 2123a on a deep side of the operation recess 2123 makes contact with (or locates close to) front surfaces (top surfaces) of the side walls 71a, 71b of the roller clamp 7 held by the clamp holding part 2113 in the pump body 2011 (see FIG. 38). In order to facilitate rotational manipulation of the roller 72 to be described later, the top, bottom, right and left walls constituting the operation recess 2123 are inclined to expand both vertically and horizontally toward the front face of the door 2012.

The vertical wall 2123a in the operation recess 2123 is provided with a rectangular slit-like roller through hole 2012a. The width of the slit in this roller through hole 2012a is greater by a predetermined value than the thickness (the width in the axial direction) of the roller 72 of the roller clamp 7. The roller through hole 2012a extends along the movement directions (vertical directions) of the roller 72 of the roller clamp 7 held by the clamp holding part 2113. The vertical length of the roller through hole 2012a is set greater than the range of movement by the roller 72 of the roller clamp 7 (the range from the release-side movement end to the block-side movement end).

A structure composed of the operation recess 2123, the roller through hole 2012a and others allows a part of (substantially a half of) the roller 72 of the roller clamp 7 to be exposed to the outside via the roller through hole 2012a, while the roller clamp 7 is held by the clamp holding part 2113 and the door 2012 is closed. Hence, a nurse or someone else can rotate the roller 72 of the roller clamp 7 held inside the infusion pump 2001 by external manipulation (on the front face of the door 2012), and can move the roller 72 between the release-side movement end and the block-side movement end as described above. Namely, the infusion tube T inside the infusion pump 2001 can be released and blocked by external manipulation.

In addition, a side end (an opposite end from the hinges 2014) of the door 2012 is provided with an engagement member 2121, which is a constituent of the door lock mechanism 2005 to be described later. The engagement member 2121 has an engagement hole 2121a into which a lock piece 2051 of a lock lever 2005A to be described later can fit while the door 2012 is closed. While the door 2012 is closed, if the lock piece 2051 of the lock lever 2005A fits into the engagement hole 2121a of the engagement member 2121 by an action to be described later, the lock piece 2051 is engaged with the engagement member 2121. In this engaged state, turning of the engagement member 2121, namely, swinging movement (turning) of the door 2012, around the hinges 2014 is inhibited so as to keep the door 2012 fully closed (locked). Additionally, an opening 2120a is formed in an inner wall 2120 of the door 2012, in order to avoid interference between the lock lever 2005A and an actuator 2052 or other elements.

—Pump Mechanism—

Next, a specific example of the pump mechanism 2 is described with reference to FIG. 42 to FIG. 45. Among the elements illustrated in FIG. 42 to FIG. 45, the eccentric cams 22 are not shown in section.

The pump mechanism 2 is similar to the one described in Embodiment 1-1 above, and is composed of a plurality of fingers 21 ... 21 (13 fingers in the example shown in FIG. 42) aligned in one direction (a direction along the infusion tube T attached to the pump body 2011), eccentric cams 22 ... 22 for independently advancing and retracting the fingers 21, a camshaft 23 for rotating the eccentric cams 22, a pressing plate 24 mentioned above, a retention frame 20, and the like.

A front face of the retention frame 20 is provided with slots 20a ... 20a which positionally correspond to the fingers 21. Tips of the fingers 21 are located at the front face side (the infusion tube T side) in the retention frame 20 and are configured to project through the slots 20a. Axial movements (movements in axial directions of the camshaft 23) of the fingers 21 ... 21 are restricted by the retention frame 20. The fingers 21 are plate-like members which can move (advance and retract) independently while effecting sliding movements with respect to each other.

Each finger 21 has a cam hole 21a. A disc-shaped eccentric cam 22 is fitted in the cam hole 21a and is capable of rotating therein. The eccentric cams 22 ... 22 are mounted on the camshaft 23 in an integrally rotatable manner.

Figure 43:
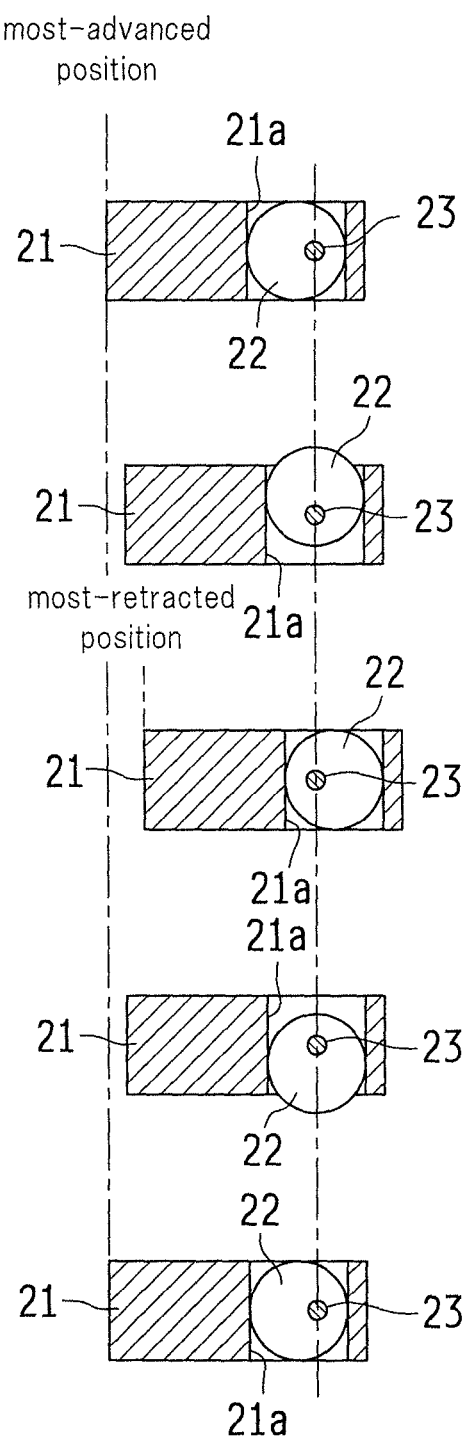
FIG. 43 illustrates a series of actions by a finger in the pump mechanism, wherein the finger is shown in section along a plane orthogonal to a camshaft.

Each of the disc-shaped eccentric cams 22 has its center offset from the camshaft 23. As shown in FIG. 43, one rotation (360-degree rotation) of the camshaft 23 causes the tip of each finger 21 to effect one reciprocating motion between the most-advanced position (a tube block position) and the most-retracted position (a full tube release position). The eccentric cams 22 are mounted on the camshaft 23, with a predetermined phase difference from each other (a phase difference in a rotation direction of the camshaft 23). Specifically, the phase difference between the eccentric cams 22 ... 22 mounted on the camshaft 23 is such that the tips of the fingers 21 ... 21 aligned in the axial direction of the camshaft 23 form a substantially sinusoidal wave (Such a phase difference is obtained by dividing 360 degrees by the number of eccentric cams 22.). FIG. 43 shows the positions of a finger 21, with every 90-degree rotation of the camshaft 23.

Figure 42:
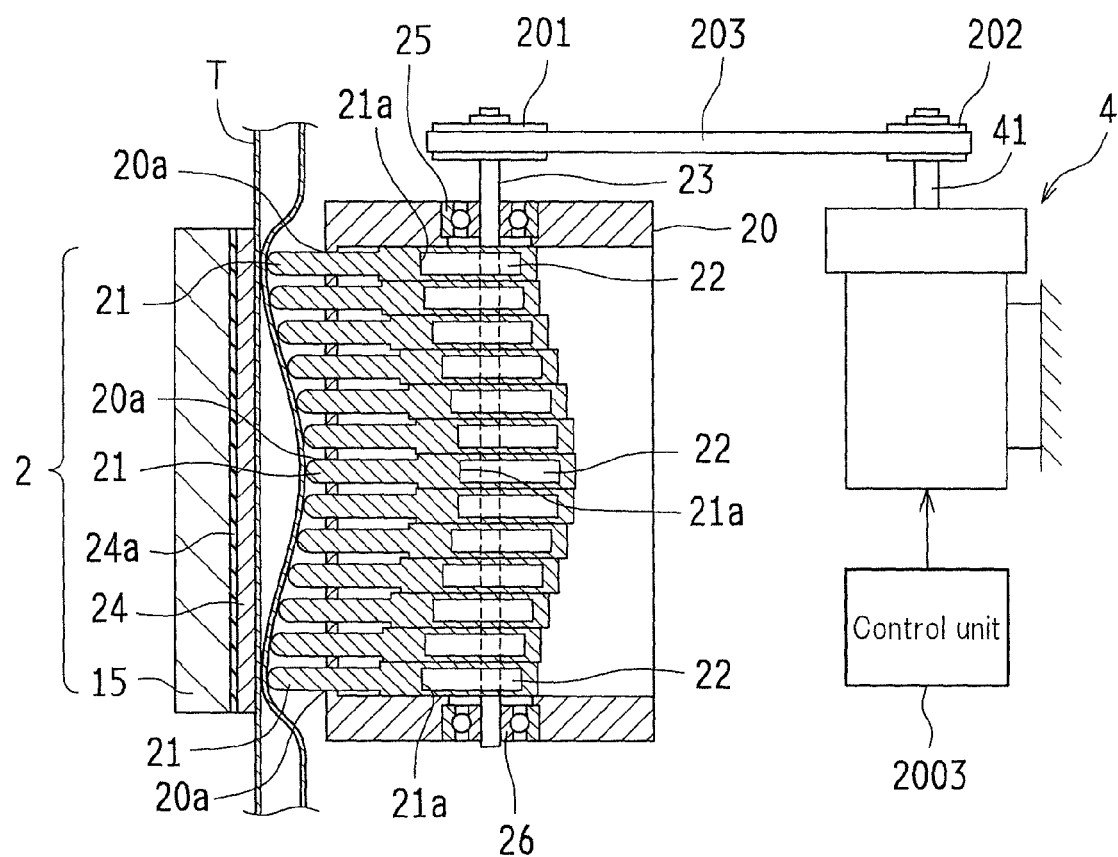
FIG. 42 shows a structure of a pump mechanism applied to an infusion pump.

As shown in FIG. 42, the camshaft 23 of the pump mechanism 2 is oriented vertically (in an alignment direction of the fingers 21 ... 21). A lower end of the camshaft 23 is rotatably held by a bearing 26 provided in the retention frame 20. An upper part of the camshaft 23 penetrates upwardly through a wall of the retention frame 20. A penetration part of the camshaft 23 is provided with a bearing 25, which rotatably supports the upper part of the camshaft 23.

A timing pulley (an idler pulley) 201 is mounted at an upper end of the camshaft 23 in an integrally rotatable manner. A timing pulley (a drive pulley) 202 is mounted on a rotation shaft 41 of an electric motor (for example, a stepper motor) 4 in an integrally rotatable manner. A timing belt 203 is trained between the timing pulley 201 on the camshaft 23 and the timing pulley 202 on the rotation shaft 41. The camshaft 23 is driven to rotate by the electric motor 4. The drive (the number of revolutions) of the electric motor 4 is controlled by a control unit 2003. In this example, the electric motor 4 is powered by a battery built in the infusion pump 2001 or by a commercial power source.

When the camshaft 23 is driven to rotate by the electric motor 4, the eccentric cams 22 rotate within the cam holes 21a of the fingers 21. Along with the eccentric rotation of the eccentric cams 22, the fingers 21 advance and retract successively from upstream (upstream in the infusion liquid feed direction) to downstream. Specifically, as shown in FIGS. 44(A), 44(B) and FIGS. 45(A), 45(B), the tips of the fingers 21 move from upstream to downstream in a peristaltic wave-like pattern. Such advance and retraction (reciprocal movements) of the fingers 21 . . . 21 impart peristaltic movements to the infusion tube T positioned between the tips of the fingers 21 . . . 21 and the pressing plate 24, thereby feeding infusion liquid in the infusion tube T from upstream to downstream. In this example, in order to alleviate an overload imposed on the infusion tube T by the fingers 21 . . . 21, a buffer sheet 24a is provided between the pressing plate 24 and a base plate 15.

In this example, the control unit 2003 is mainly configured by a microcomputer or the like. The control unit 2003 can variably adjust the flow rate of the infusion liquid, for example, by controlling the number of revolutions of the electric motor 4 based on a preset flow rate of the infusion liquid (an amount of feeding the infusion liquid per unit time) that is manually input by an operation panel 2122 (see FIG. 31) at a front face of the door 2012. For example, the flow rate of the infusion liquid can be set in a range between 1 mL/h and 1200 mL/h, by an increment of [1 mL/h]. Further, the control unit 2003 is configured to indicate operational information such as "flow rate of the infusion liquid (amount of infusion)" and "cumulative infusion time" as well as various alerts including "air-in-line" and "failure: door open" on the operation panel 2122.

—Door Lock Mechanism—

Further, the door lock mechanism 2005 is described with reference to FIG. 32 to FIG. 40.

The door lock mechanism 2005 in this example is composed of, for example, a lock lever 2005A, a fulcrum shaft 2053 provided at a rear side of the front wall 2110 of the pump body 2011, a lock spring 2054, and an engagement member 2121 provided at the door 2012.

The lock lever 2005A has a lever piece 2050, a lock piece 2051, and an actuator (an input piece) 2052. The lever piece 2050 is integrally composed of a longitudinal arm 2050a extending vertically in the pump body 2011, and a transverse arm 2050b extending laterally in the pump body 2011 (in a direction orthogonal to the longitudinal arm 2050a).

The lock piece 2051 is integrated with a distal end of the longitudinal arm 2050a (an end of the lock lever 2005A). The lock piece 2051 has a plate-like shape and extends in a direction orthogonal to the longitudinal arm 2050a. As mentioned above, the lock piece 2051 is capable of protruding outwardly from the through hole 2110b formed in the vertical wall 2110a of the lock recess 2011a.

The transverse arm 2050b is integrally composed of a first transverse piece 2501b extending laterally in the pump body 2011, a joint piece 2502b extending from a distal end of the first transverse piece 2501b toward the front face of the pump body 2011 along the front-back directions in the pump body 2011, and a second transverse piece 2503b originating from a distal end of the joint piece 2502b and extending laterally in pump body 2011. The actuator 2052 is integrally formed at a distal end of the second transverse piece 2503b (at the other end of the lock lever 2005A).

The actuator 2052 is a plate-like member extending vertically in the pump body 2011. As shown in FIG. 32 to FIG. 40, the actuator 2052 is positioned at a bottom center of the clamp holding part 2113. With the roller clamp 7 being held by the clamp holding part 2113, an end 2052a of the actuator 2052 is opposed to the outer periphery of the roller 72 of the roller clamp 7. In other words, the actuator 2052 is positioned such that its end 2052a can make contact with the outer periphery of the roller 72 of the roller clamp 7.

Among the various pieces constituting the lock lever 2005A, the longitudinal arm 2050a (the lock piece 2051), the first transverse piece 2501b of the transverse arm 2050b, and a part of the joint piece 2502b are located on the rear side of the front wall 2110 of the pump body 2011, whereas the remaining part of the joint piece 2502b and the second transverse piece 2503b (the actuator 2052) are located on the front side of the front wall 2110 of the pump body 2011. The joint piece 2502b is located on both the front side and the rear side of the front wall 2110 via the through hole 2110c formed in the front wall 2110.

The longitudinal arm 2050a and the transverse arm 2050b are joined orthogonally. A joint 2050c of the longitudinal arm 2050a and the transverse arm 2050b is rotatably held by the fulcrum shaft 2053, allowing the entirety of the lock lever 2005A to turn (swing) around the fulcrum shaft 2053. Turning of the lock lever 2005A allows the lock piece 2051 to move between a locked position shown in FIG. 32, FIG. 34 and FIG. 37 and an unlocked position shown in FIG. 35 and FIG. 36.

Additionally, a positioning member (a projection) 2056 for regulating the amount of projection by the lock piece 2051 into the lock recess 2011a (the amount of movement by the lock piece 2051) is provided adjacent to the longitudinal arm 2050a of the lock lever 2005A. The lock piece 2051 is positioned at the locked position, with the longitudinal arm 2050a of the lock lever 2005A abutting the positioning member 2056.

The fulcrum shaft 2053 is a stepped shaft projecting on the rear side of the front wall 2110 of the pump body 2011 (a shaft vertical to the front wall 2110). A small-diameter part 2053a of this fulcrum shaft 2053 is fitted in a fitting hole (a fulcrum hole) 2050d formed at the joint 2050c of the lever piece 2050. A pin 2055 is attached to a tip end of the small-diameter part 2053a of the fulcrum shaft 2053. A lock spring (a torsion coil spring) 2054 is disposed between the pin 2055 and the lever piece 2050 (the joint 2050c). An end of the lock spring 2054 is latched on the pin 2055, and the other end of the lock spring 2054 is latched on the first transverse piece 2501b of the lever piece 2050. An elastic force by the lock spring 2054 biases the lever piece 2050 in the direction of an arrow in FIG. 2 (in a clockwise direction (to the lock side) as seen from the front of the pump body 2011).

Figure 32:
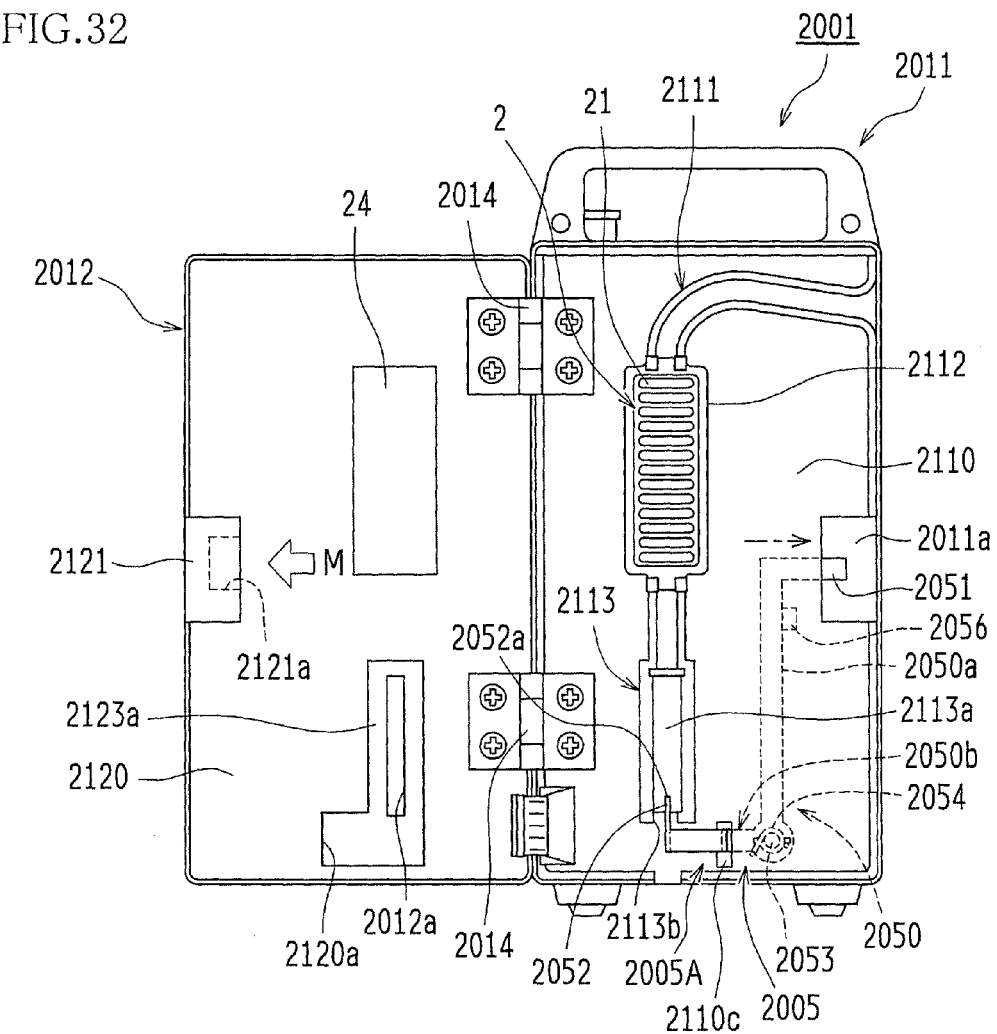
FIG. 32 shows a schematic configuration of yet another exemplary infusion pump according to the present invention, in a state where the door of the infusion pump is open.
Figure 33:
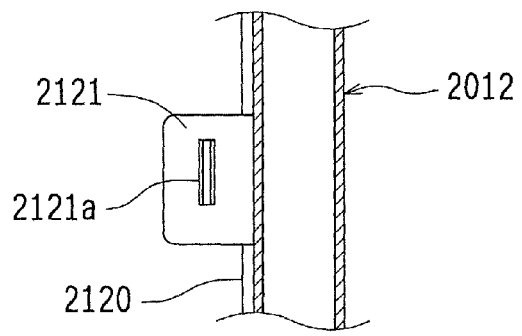
FIG. 33 is a view taken in the direction of Arrow M in FIG. 32.
Figure 34:
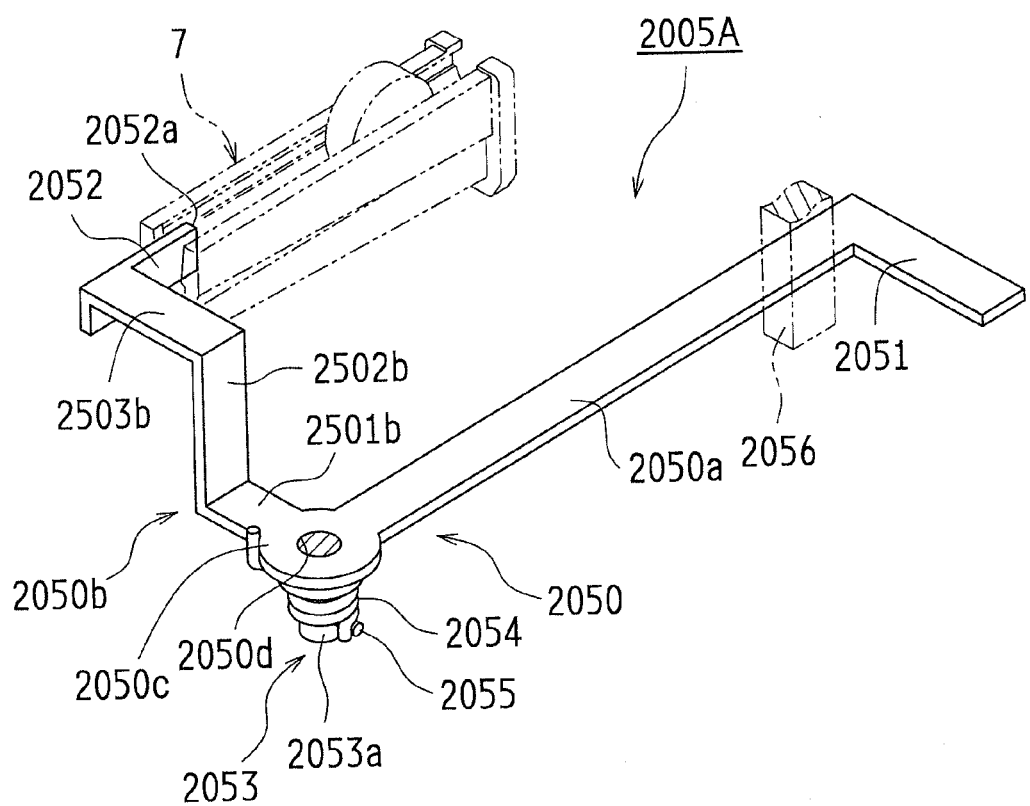
FIG. 34 is perspective view of a lock lever, etc. applied to the infusion pump shown in FIG. 32.
Figure 37:
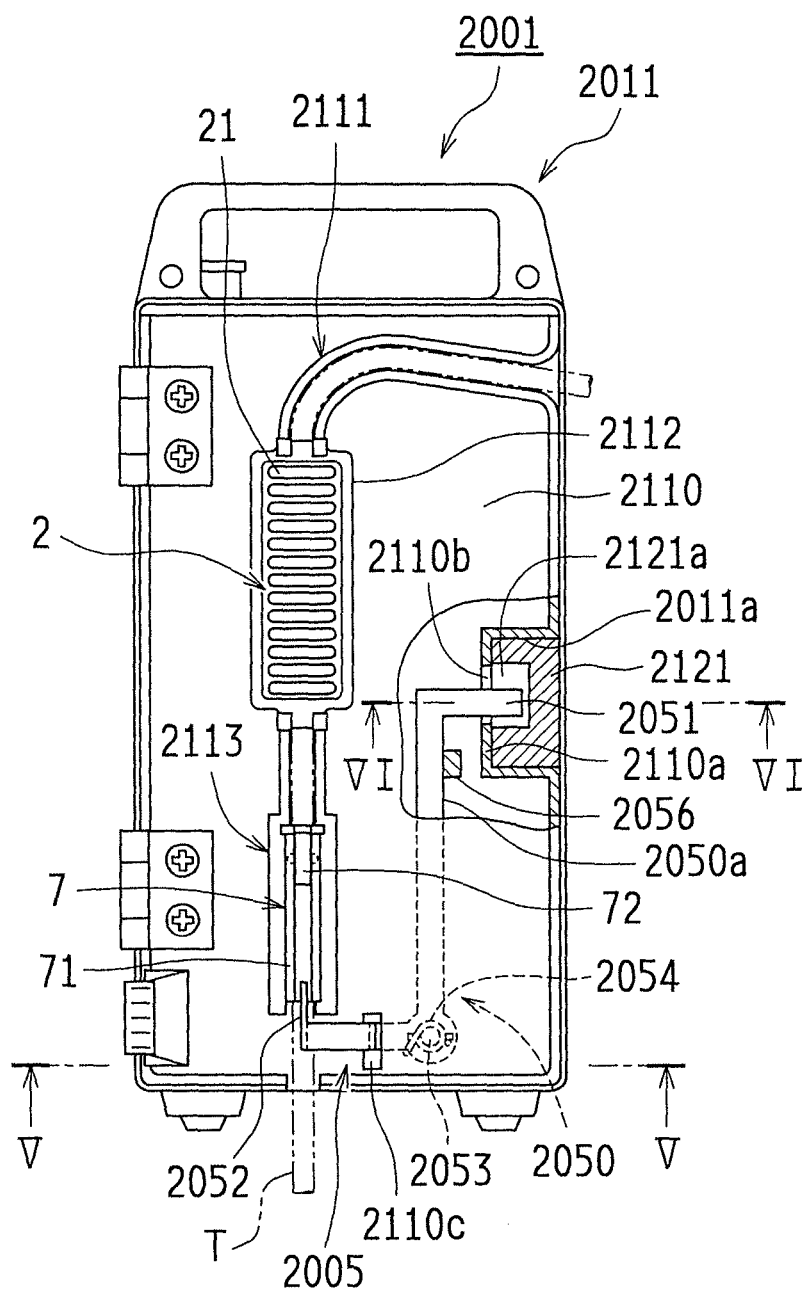
FIG. 37 is a schematic configuration of yet another exemplary infusion pump according to the present invention, in a state where the door (omitted in this figure) is locked from the state shown in FIG. 36 by rotational manipulation of a roller of the roller clamp.

In the door lock mechanism 2005 of the above structure, when the actuator 2052 of the lock lever 2005A is free, the lock piece 2051 stays at the locked position as shown in FIG. 32, FIG. 34 and FIG. 37 by the elastic force of the lock spring 2054. On the other hand, when a downward force (a force away from the pump unit 2112) is applied to the actuator 2052, the lock lever 2005A turns counterclockwise around the fulcrum shaft 2053 (counterclockwise as seen from the front of the pump body 2011). Then, when the actuator 2052 has reached the position shown in FIG. 35, FIG. 36 and FIG. 39(A) (a position corresponding to the block-side movement end of the roller 72), the lock piece 2051 stays at the unlocked position. In this example, the elastic force of the lock spring 2054 is set smaller than the force by which the roller 72 pushes the actuator 2052 when a nurse or someone else rotates the roller 72 of the roller clamp 7. Hence, a nurse or someone else can turn the lock lever 2005A against the elastic force of the lock spring 2054 by manipulating the roller 72.

—Description of Releasing/Blocking Operations and the like for the Roller Clamp—

The following description concerns a manner of setting the infusion tube T to the infusion pump 2001, and the releasing/blocking operations for the roller clamp 7, referring to FIG. 32 to FIG. 41.

(S1) First of all, in the infusion set S shown in FIG. 46, the roller 72 of the roller clamp 7 is manipulated to block the infusion tube T (the roller 72 is located at the block-side movement end).

Figure 35:
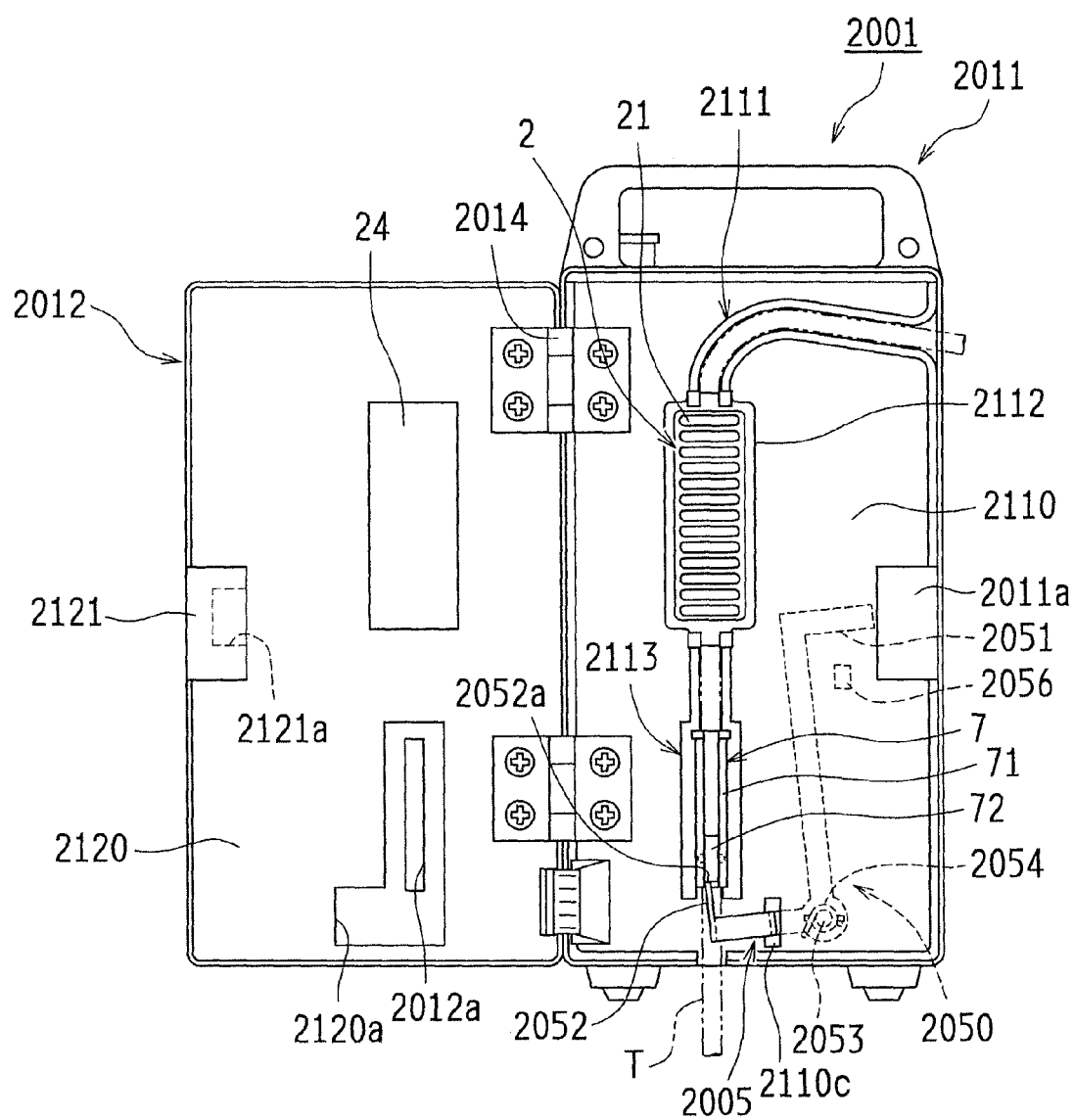
FIG. 35 shows a schematic configuration of yet another exemplary infusion pump according to the present invention, in a state where the door of the infusion pump is open and the roller clamp is held in the pump body.
Figure 36:
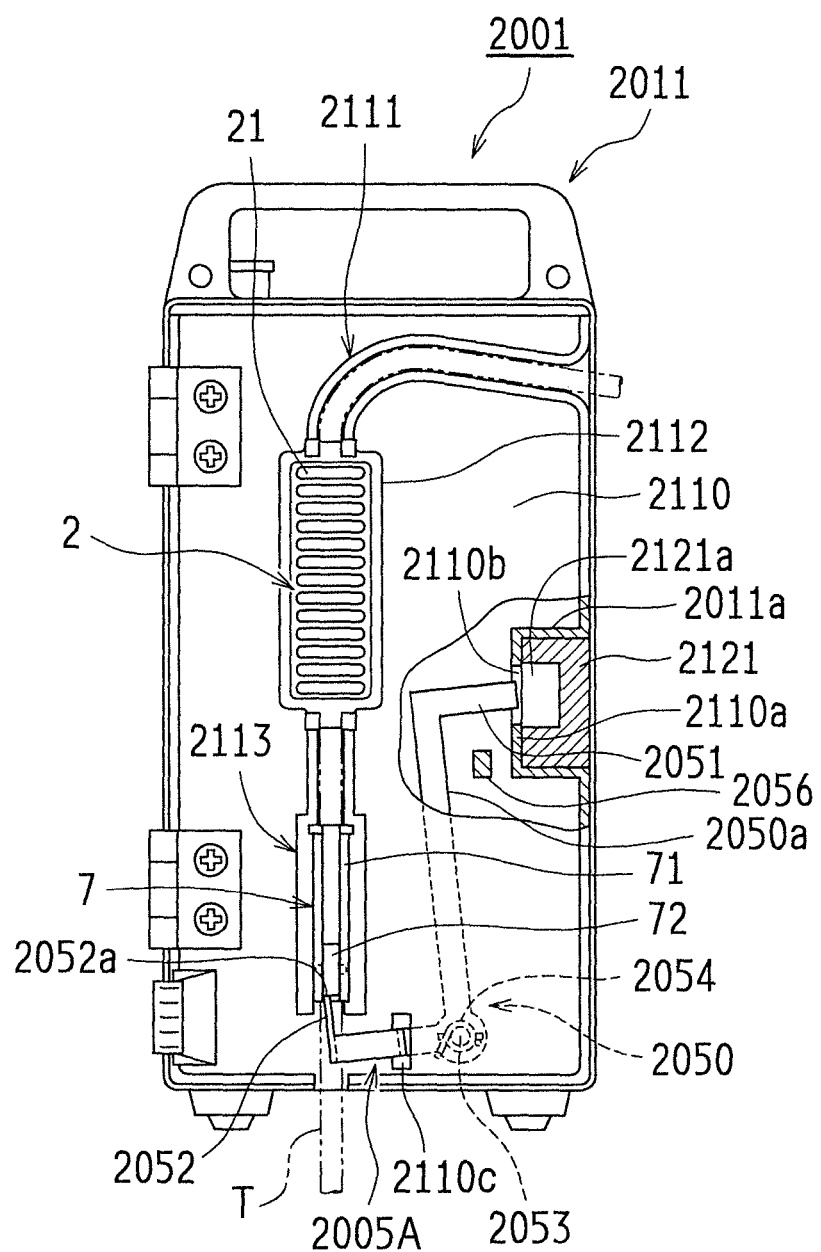
FIG. 36 is a schematic configuration of yet another exemplary infusion pump according to the present invention, in a state where the door (omitted in this figure) of the infusion pump is closed from the state shown in FIG. 35.

Next, while the door 2012 of the infusion pump 2001 is kept open (see FIG. 32), the roller clamp 7 is brought to the front face of the pump body 2011, and the clamp body 71 of the roller clamp 7 is fitted into the clamp holding part 2113 (the holding recess 2113a) of the pump body 2011 (see FIG. 35 and FIG. 40(A)), with the flange 71f being oriented to the top. Specifically, with the roller clamp 7 being kept above the clamp holding part 2113, the infusion tube T at a downstream side of the roller clamp 7 is pushed in between the actuator 2052 of the lock lever 2005A and the side wall 2113b of the clamp holding part 2113 (see FIG. 32 and FIG. 38), and the infusion tube T is inserted in the holding recess 2113a of the clamp holding part 2113 (an inner side relative to the actuator 2052). Then, with the infusion tube T being inserted in the holding recess 2113a, the roller clamp 7 and the infusion tube T are slid downwardly so as to fit the clamp body 71 into the holding recess 2113a. As a manner for holding the roller clamp 7 in the clamp holding part 2113, the roller clamp 7 can be fitted into the holding recess 2113a while the lock lever 2005A is turned by an index finger or the like toward the unlocked position (turned counterclockwise as seen from the front of the pump body 2011) or while the actuator 2052 is pushed down by the roller 72 of the roller clamp 7.

In the state where the roller clamp 7 is held by the clamp holding part 2113 of the pump body 2011 in the above explained manner, the end 2052a of the actuator 2052 in the lock lever 2005A abuts the outer periphery of the roller 72 which stays at the block-side movement end of the roller movement range, and the lock piece 2051 stays at the unlocked position, as shown in FIG. 35 and FIG. 40(A).

(S2) With the roller clamp 7 being fitted in the clamp holding part 2113, the infusion tube T at the upstream side of the roller clamp 7 is attached to the tube attachment guide 2111 and the pump unit 2112. After the tube is attached in this manner, the door 2012 is closed. In this state (where the door 2012 is closed), the roller 72 exposed at the front face of the door 2012 is manually rotated upwardly (rotated toward the tube release position, or the release-side movement end) (see FIG. 40(B)). During this upward movement of the roller 72, the lock lever 2005A turns toward the lock position (turns counterclockwise as seen from the front of the pump body 2011) by the elastic force of the lock spring 2054. At the moment when the actuator 2052 of the lock lever 2005A loses contact with the outer periphery of the roller 72 (when the actuator 2052 gets free), the lock piece 2051 comes to the locked position (the position shown in FIG. 37 to FIG. 39, etc.).

When effecting the operation (S2), if the roller 72 of the roller clamp 7 held by the clamp holding part 2113 of the clamp body 11 does not stay at the tube block position (if the actuator 2052 of the lock lever 2005A is free), the lock piece 2051 of the lock lever 2005A projects into the lock recess 2011a of the pump body 2011 by the elastic force of the lock spring 2054. Hence, if someone tries to close the door 2012 in this state, the engagement member 2121 of the door 2012 abuts (interfers with) the lock piece 2051, so that the door 2012 cannot be closed. Owing to this structure, if, for example, a nurse or someone else forgets to block the infusion tube T by the roller clamp 7 when attaching the infusion tube T to the infusion pump 2001, he/she can be informed of the error (failure to block the tube). In the case of such failure, the roller 72 of the roller clamp 7 held by the clamp holding part 2113 is rotated to the block-side movement end so as to move the lock piece 2051 to the unlocked position (so as to unlock the door). In this unlocked state, the door 2012 is closed, and the roller 72 is mamually rotated to the tube release position (the release-side movement end).

After the infusion tube is set in this manner, the infusion pump 2001 is driven to prime the infusion set S. Alternatively, the infusion set S may be primed in advance by a pressure difference before the infusion tube is set to the infusion pump 2001.

After the preparation of infusion treatment is completed by the above processes, the infusion pump 2001 is driven to start a prescribed infusion treatment (drip infusion).

(S3) When the cumulative time (or the cumulative dose) reaches a preset value after the infusion pump 2001 started running, the infusion pump 2001 is stopped. After the stop of the infusion pump 2001 is confirmed, the roller 72 exposed to the front face of the door 2012 is manually rotated downwardly (rotated toward the tube block position, or the block-side movement end). During this downward movement of the roller 72, the outer periphery of the roller 72 abuts the end 2052a of the actuator 2052 of the lock lever 2005A. From this moment, the lock lever 2005A turns toward the unlocked position (turns counterclockwise as seen from the front of the pump body 2011) against the elastic force of the lock spring 2054. When the roller 72 has reached the block-side movement end (when the infusion tube T is fully blocked), the lock piece 2051 is unlocked (see FIG. 6, etc.). Thereafter, the door 2012 is opened to remove the infusion tube T and the roller clamp 7 from the infusion pump 2001.

As described above, while the door 2012 is closed (locked), the infusion pump 2001 in this example maintains engagement of the lock piece 2051 of the door lock mechanism 2005 with the engagement member 2121 unless the roller 72 of the roller clamp 7 is manipulated to the tube block position. Hence, even if someone tries to open the door 2012 accidentally during infusion treatment, the infusion pump 2001 does not allow the door 2012 to be open. Hence, the infusion pump 2001 can prevent free flow due to an operational error.

Further, even if someone tries to open the door 2012 after the completion of infusion treatment but before the infusion tube T is blocked by the roller clamp 7, the infusion pump 2001 in this example does not allow the door 2012 to be open. Hence, the infusion pump 2001 can also avoids a trouble of removing the infusion tube T from the infusion pump 2001 while a user forgets to block the infusion tube T by the roller clamp 7 (in a situation where free flow may occur).

Additionally, the infusion pump 2001 in this example can prevent free flow by holding the roller clamp 7 of the infusion tube T in the pump body 2011, and thus does not require a special clamp. Therefore, this infusion pump can also prevent free flow when employed with a common infusion tube equipped with a roller clamp.

As described above, the infusion pump 2001 in this example can reliably prevent free flow due to operational errors by health-care professionals such as nurses or due to some other causes.

Incidentally, if the door 2012 of the infusion pump 2001 needs to be closed when the infusion pump 2001 is carried around or stored unused, the following operations can be applied.

In order to lock the door 2012, a plate, a stick or the like (or the roller 72 of the roller clamp 7) is inserted into the roller through hole 2012a of the door 2012 from the front face of the door, and is maneuvered to press down the actuator 2052 of the lock lever 2005A so as to locate the lock piece 2051 at the unlocked position. The door 2012 is closed in this unlocked state, and the plate, stick or the like is pulled out to lock the door 2012 fully closed. On the other hand, in order to unlock the door 2012, a plate, a stick or the like is inserted into the roller through hole 2012a of the door 2012 from the front face of the door, and is maneuvered to press down the actuator 2052 of the lock lever 2005A so as to locate the lock piece 2051 at the unlocked position. The door 2012 is opened in this unlocked state.

In the above example, the lock spring 2054 for biasing the lock piece 2051 toward the locked position is a torsion coil spring. However, this is a non-limiting example, and the lock spring used in the present invention may be any other spring (an elastic member), such as a compression coil spring and an extension coil spring, which can bias the lock piece 2051 (the lock lever 2005A) toward the locked position.

In the above example, the lock piece 2051 (the lock lever 2005A) is provided on the pump body 2011, and the engagement member 2121 is provided on the door 2012. However, the present invention should not be limited to this arrangement. Instead, the lock piece may be provided on the door 2012, and the engagement member may be provided on the pump body 2011.

Embodiment 2-2

The next description is directed to still another example of the infusion pump.

Similar to Embodiment 2-1 described above, an infusion pump in this example is a peristaltic finger infusion pump, and is equipped with a pump body 2011, and a door 2012 which closes on a front face (a tube attachment position) of the pump body 2011 (see FIG. 31, FIG. 32, etc.). The door 2012 is held swingably (in a freely turning manner) on the pump body 2011 by hinges 2014, 2014, and is capable of swinging between a fully closed position and a fully open position (for example, a 180-degree open position) with respect to the front face of the pump body 2011.

Except the arrangements to be described below, the infusion pump in this example is similar to Embodiment 2-1 described above, and hence detailed description of similar elements are omitted.

The infusion pump in this example is equipped with a roller position sensor 2600 and an electric door lock mechanism 2700 (neither shown).

The roller position sensor 2600 may be, for example, a known photoelectric sensor (reflective type) composed of a light-emitting element and a light-receiving element. When the roller 72 of the roller clamp 7 held by the clamp holding part 2113 in the pump body 2011 stays at the tube release position (the release-side movement end) (see FIG. 37), the roller position sensor 2600 outputs a roller detection signal (an ON signal). The roller position sensor 2600 may be a through-beam sensor in which a light-emitting element and a light-receiving element are opposed to each other. In addition to these photoelectric sensors, for example, it is also possible to use other known position/object detection means such as a limit switch which switches on (or switches off) when the roller 72 comes to the tube release position (the release-side movement end).

The electric door lock mechanism 2700 has, for example, a solenoid as an actuator, and is configured to lock the door 2012 closed when the output signal from the roller position sensor 2600 is ON, and to open (unlock) the door 2012 when the output signal from the roller position sensor 2600 is OFF.

In this example, the door 2012 is locked and unlocked in the following manner. While the door 2012 is closed and unlocked, the roller 72 of the roller clamp 7 held by the clamp holding part 2113 of the pump body 2011 is rotationally moved from the tube block position to the tube release position (the release-side movement end) (see FIG. 37). Due to this movement, the detection signal from a locked position sensor 600 is switched from OFF to ON, which activates the door lock mechanism 2700 to lock the door 2012. While the door 2012 is closed and locked, the roller 72 is rotationally moved to the tube release position. Due to this movement, the detection signal from the locked position sensor 600 is switched from ON to OFF, which deactivates the lock by the door lock mechanism 2700 to unlock the door 2012.

As described above, while the door 2012 is closed (locked), the infusion pump in this example also keeps the door 2012 locked unless the roller 72 of the roller clamp 7 is manipulated to the tube block position. Hence, even if someone tries to open the door 2012 accidentally during infusion treatment, this infusion pump does not allow the door 2012 to be open, and thus can prevent free flow by an operational error.

Further, even if someone tries to open the door 2012 after the completion of infusion treatment but before the infusion tube T is blocked by the roller clamp 7, the infusion pump in this example does not allow the door 2012 to be open. Hence, this infusion pump can also avoid a trouble of removing the infusion tube T from the infusion pump 2001 while a user forgets to block the infusion tube T by the roller clamp 7 (in a situation where free flow may occur). Furthermore, this infusion pump can prevent a failure to release the roller clamp 7 after the start of infusion treatment.

Other Configuration Examples for the Infusion Pump
Configuration Example (1)

The following description is directed to a different configuration example for an infusion pump.

As described above, a peristaltic finger infusion pump is equipped with a pump mechanism having, for example, a plurality of fingers aligned in a pump body, cams for advancing and retracting the fingers independently, and a pressing plate provided on the door of the pump in a manner opposed to tips of the fingers while the door is closed. An infusion tube (made of polyvinyl chloride or polybutadiene, for example) is connected to an infusion bag and is attached to the pump body (on the front side of the fingers). When the door is closed, the infusion tube is positioned between the fingers and the pressing plate. In this state, the cams cause the fingers to advance and retract independently. By such finger movements, the infusion tube is pressed successively by each of the fingers, so that infusion liquid can be fed by a peristaltic action (see, for example, JP 2008-113726 A, JP H05-076596 A, and JP H11-342199 A).

Generally, in this type of peristaltic finger infusion pump, the door is swingably held by the pump body via hinges. For example, if the infusion liquid falls on the floor or somewhere else, the hinges may get loose due to the impact of fall. The hinges may also get loose if the door has been repeatedly opened and closed for a vast number of times due to long-term use or other reasons. Loose hinges may cause an increase in the gap (distance) between the tips of the fingers and the pressing plate in the pump mechanism while the door is closed. If such an infusion pump is put into operation, the infusion tube is not completely blocked by a finger that has reached the most-advanced position, which may result in free flow (free fall of infusion liquid) and a drastic increase in flow rate of the infusion liquid. Further, in the case where the door has been deformed due to the impact of fall of an infusion pump or some other reasons, there may also be an increase in the gap between the tips of the fingers and the pressing plate in the pump mechanism while the door is closed. Similarly, if such an infusion pump is put into operation, the flow rate of the infusion liquid may increase drastically.

If a nurse or someone else overlooks an abnormal flow rate of the infusion liquid and continues infusion treatment, a prescribed amount of infusion liquid may not be administered to a patient (normal infusion treatment may be impossible). In consideration of this risk, this example aims to provide a peristaltic finger infusion pump which is capable of informing health-care professionals such as nurses if the flow rate of the infusion liquid is abnormal due to a fall of the pump or other reasons.

A means for achieving this object concerns an infusion pump equipped with a pump mechanism having a plurality of fingers aligned in one direction, cams for advancing and retracting the fingers independently, and a pressing plate provided on a door in a manner opposed to the tips of the fingers while the door is closed. The door closes on the front side of the fingers in a freely opening and closing manner. With the closure of the door, the infusion tube is positioned between the fingers and the pressing plate in the pump mechanism. In this state, each of the fingers is caused to advance and retract with respect to the infusion tube, so that infusion liquid is fed by a peristaltic action. This infusion pump is further provided with failure alarm means (for example, a control unit 3003, a display panel 3121, a buzzer 3009, etc.) which issues a failure alarm if, while the door is closed, a value about the gap between the tip of a particular finger and the pressing plate in the pump mechanism is greater than a predetermined acceptable value.

The infusion pump having this configuration issues a failure alarm if, while the door is closed, a value about the gap between the tip of a particular finger of the pump mechanism and the pressing plate provided on the door is greater than a predetermined acceptable value. Hence, while the door is closed, if the gap between the tip of a particular finger in the pump mechanism and the pressing plate gets greater due to a fall of the infusion pump or some other reasons and, as a result, if the flow rate of the infusion liquid has drastically increased, this infusion pump can inform health-care professionals such as nurses that the flow rate of the infusion liquid is abnormal. According to this configuration, it is possible to prevent infusion treatment under an abnormal flow rate of the infusion liquid.

Regarding the gap between the tip of a particular finger and the pressing plate while the door is closed, the acceptable value is set, for example, in the following manner. First, an upper limit of the gap (the gap between the tip of the particular finger and the pressing plate), at which a drastic increase in the flow rate of the infusion liquid (free flow) due to a fall of the pump or other reasons does not occur, is obtained by experiments, calculations, etc. Then, the acceptable value for the gap is set in accordance with this upper limit.

As a specific configuration, the infusion pump may be also equipped with gap detection means (for example, a distance sensor) which detects a gap between the tip of a finger at the most-retracted or most-advanced position and the pressing plate while the door is closed. While the door is closed, if the gap between the tip of the particular finger and the pressing plate provided on the door, as detected by the gap detection means, is greater than a predetermined acceptable value, the infusion pump is configured to issue a failure alarm.

In this case, one gap detection means (a distance sensor) may be provided at an upstream side (an upstream side in the infusion liquid feed direction) of the pump mechanism, and another gap detection means (another distance sensor) may be provided at a downstream side thereof. Even if the door is inclined to the pump body (the front wall) due to loose hinges, the values detected by the two gap detection means (the two distance sensors) ensure a correct judgement as to whether the gap between the tip of a particular finger and the pressing plate provided on the door is within a normal range (equal to or lower than the acceptable value) while the door is closed.

Incidentally, the gap between the tip of the fingers in the pump mechanism and the pressing plate provided on the door is correlated with the gap between the front wall of the pump body and the pressing plate provided on the door. Therefore, the infusion pump may also be configured to detect the gap between the front wall and the pressing plate, and to inform health-care projessionals such as nurses that the flow rate of the infusion liquid is abnormal, if the detected value is greater than the acceptable value.

As another specific configuration, the infusion pump may be also equipped with a limit switch which is turned on if the gap between the tip of a particular finger in the pump mechanism and the pressing plate provided on the door, while the door is closed, is greater than the acceptable value. If the limit switch is turned on while the door is closed, the infusion pump is configured to inform that the flow rate of the infusion liquid is abnormal. In this configuration, the limit switch may be turned off, instead of being turned on, if the gap between the tip of a particular finger in the pump mechanism and the pressing plate provided on the door, while the door is closed, is greater than the acceptable value.

Another means for achieving the above-mentioned object concerns an infusion pump equipped with a pump mechanism having a plurality of fingers aligned in one direction, cams for advancing and retracting the fingers independently, and a pressing plate provided on a door in a manner opposed to the tips of the fingers while the door is closed. The door closes on the front side of the fingers in a freely opening and closing manner. With the closure of the door, the infusion tube is positioned between the fingers and the pressing plate of the pump mechanism. In this state, each of the fingers is caused to advance and retract with respect to the infusion tube, so that infusion liquid is fed by a peristaltic action. This infusion pump is further provided with pressure detection means (for example, a pressure sensor) which detects a pressure applied to the pressing plate by the infusion tube. While the door is closed, if the pressure detected by the pressure detection means is smaller than a predetermined acceptable value, the infusion pump is configured to issue a failure alarm.

The infusion pump according to this configuration has a following feature. While the door is closed, if the gap between the tip of the most-advanced finger and the pressing plate provided on the door is normal, the pressing plate receives a maximum pressure from the infusion tube. On the other hand, due to the above-mentioned reasons (impact by a fall of the infusion pump, or other reasons), if the gap between the tip of the most-advanced finger and the pressing plate increases while the door is closed, the pressing plate receives a less pressure from the infusion tube. Focusing attention on this regard, the infusion pump of this configuration issues a failure alarm if, while the door is closed, the pressure detected by the pressure detection means (the pressure applied to the pressing plate) is smaller than a predetermined acceptable value.

While the door is closed, if the gap between the tip of a particular finger and the pressing plate gets greater due to a fall of the infusion pump or some other reasons and, as a result, if the flow rate of the infusion liquid has drastically increased, the infusion pump of this configuration can also inform health-care professionals such as nurses that the flow rate of the infusion liquid is abnormal. According to this configuration, it is possible to prevent infusion treatment under an abnormal flow rate of the infusion liquid.

Next, a specific configuration (a working example) of the infusion pump in this example is described with reference to FIG. 50 to FIG. 60.

An infusion pump 3001 in this example is a peristaltic finger infusion pump, and is equipped with a pump body (a casing) 3011, and a door 3012 which closes on a front face (a tube attachment position) of the pump body 3011. The door 3012 is held swingably (in a freely turning manner) on the pump body 11 by hinges 3013, 3013, and is capable of swinging between a fully closed position and a fully open position (for example, a 180-degree open position) with respect to the front face of the pump body 3011. The pump body 3011 and the door 3012 are equipped with a door lock mechanism 3005 which keeps the door 3012 in a closed state after the door 3012 is closed. The door lock mechanism 3005 is to be described later.

The pump body 3011 is equipped with a tube attachment guide (a guide groove) 3111. The tube attachment guide 3111 is composed of, from the upstream side in the infusion liquid feed direction, an upstream guide unit 3111a, a pump unit 3111b which is connected to the upstream guide unit 3111a and which has an enlarged rectangular shape, and a downstream guide unit 3111c. Tips of fingers 21 . . . 21 of the pump mechanism 2 (to be described later) are located in the pump unit 3111b.

The upstream guide unit 3111a of the tube attachment guide 3111 has a transversely curved (bent) shape. The downstream guide unit 3111c located downstream of the pump unit 3111b extends vertically in a straight line. The groove widths of the upstream guide unit 3111a and the downstream guide unit 3111c correspond to an outer diameter of the infusion tube T (made of polyvinyl chloride or polybutadiene, for example) connected to an infusion bag. The infusion tube T can be fitted in the upstream guide unit 3111a and the downstream guide unit 3111c so as to be attached to the infusion pump 3001.

The upstream guide unit 3111a is equipped with a tube clamp 3112. The tube clamp 3112 temporality holds the infusion tube T during the process of attaching the infusion tube to the infusion pump 3001. After the infusion tube is attached to the infusion pump, the clamp is automatically released on closure of the door 3012. Further, a clamp lever (not shown) is provided in the vicinity of the tube clamp 3112. While the infusion tube T is attached, the tube clamp 3112 can be manually released by the crank lever.

The pump body 3011 further includes a lever housing recess 3011a at a side end thereof (an end opposite to the hinges 3013), and a lock chamber 3011b provided at an inner side of the lever housing recess 3011a. The lever housing recess 30111a can accommodate a lock lever 3051 of a door lock mechanism 3005 to be described later. The lock chamber 3011b can accommodate a lock piece 3052 to be described later. At an upper part of the lock chamber 3011b, an engagement piece 3054 for engaging with a lock latch 3053 of the lock piece 3052 is provided.

Figure 51:
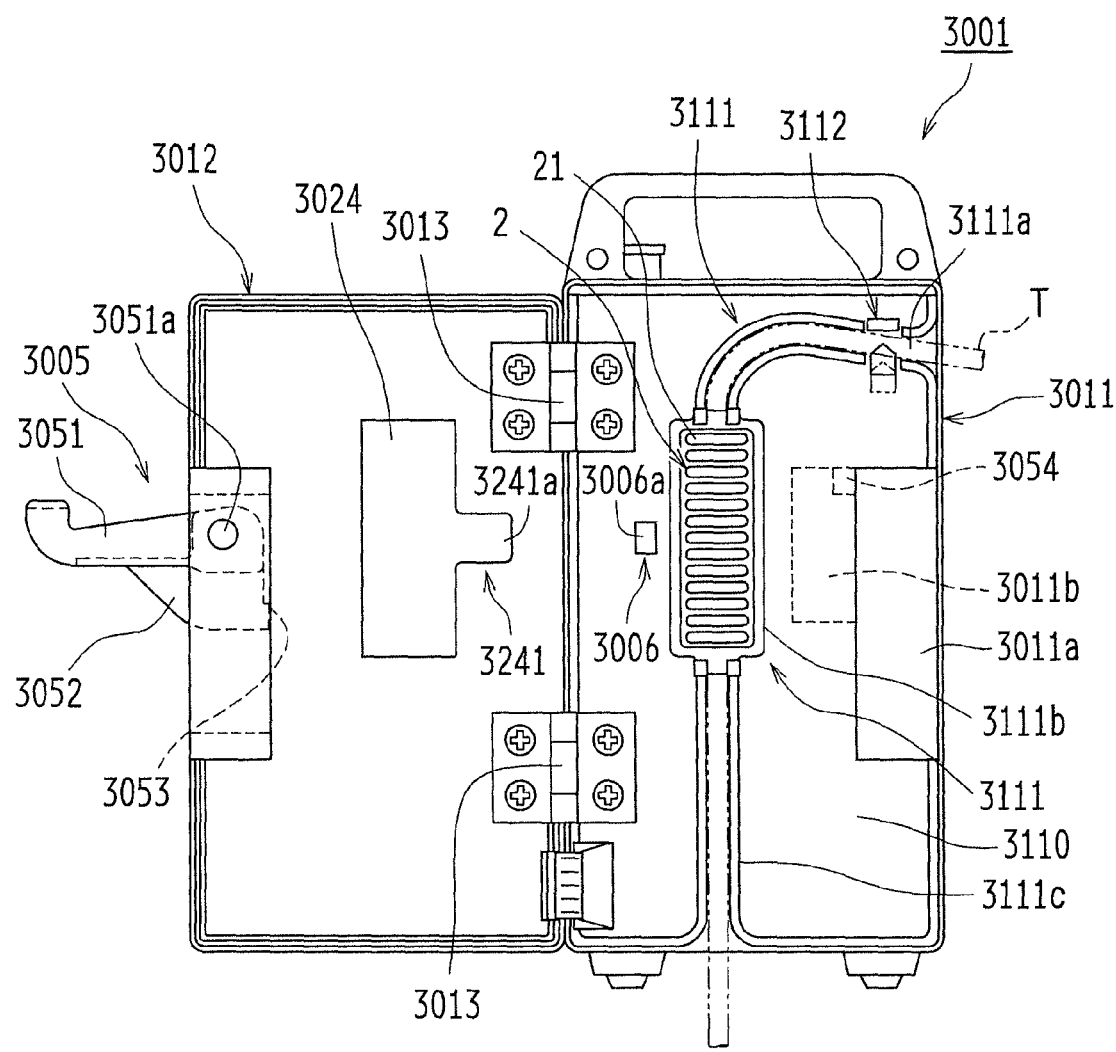
FIG. 51 shows a schematic configuration of still another exemplary infusion pump, in a state where the door of the infusion pump is open.
Figure 52:
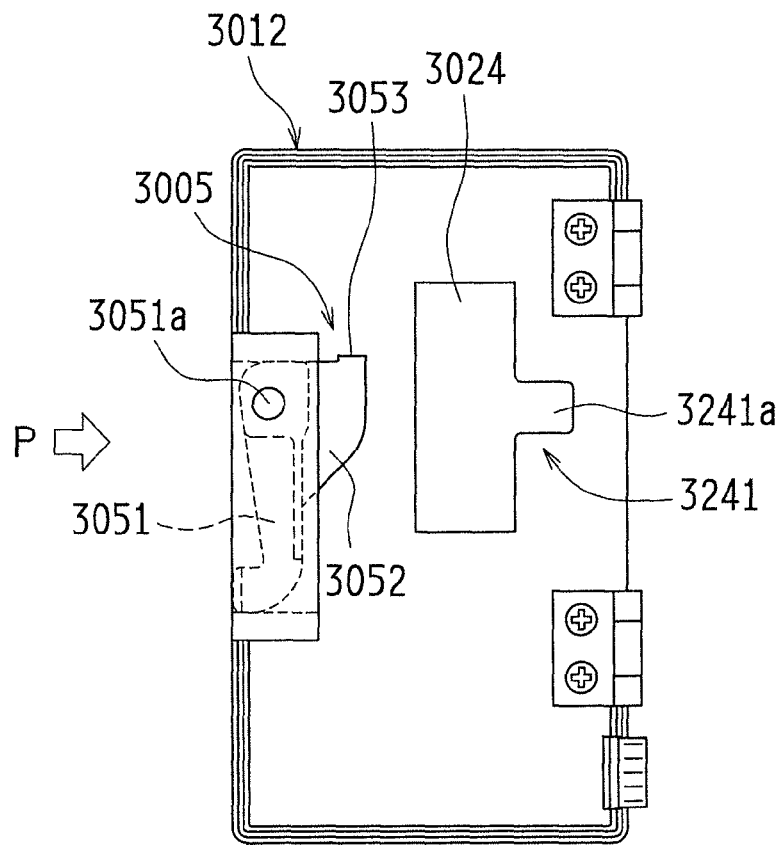
FIG. 52 illustrates the door shown in FIG. 51, with the lock lever being manipulated to a lock side.
Figure 53:
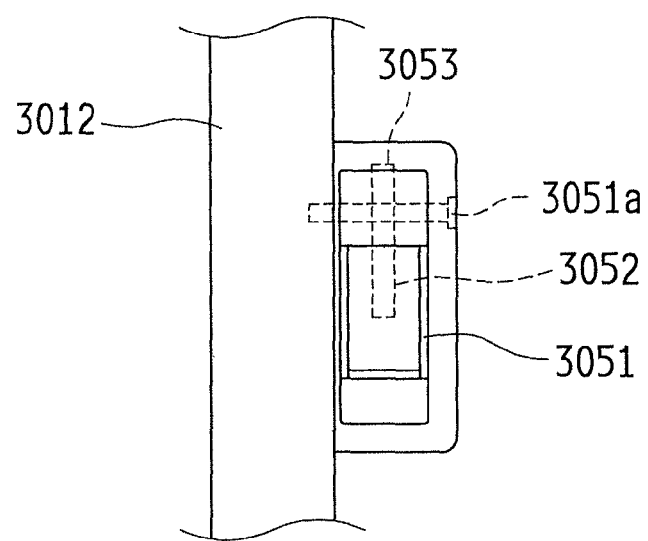
FIG. 53 is a view taken in the direction of Arrow P in FIG. 52.

The door 3012 further includes a lock lever 3051 at a side end thereof (an end opposite to the hinges 3013). The lock lever 3051 is rotatable around a rotation shaft 3051a, and swingable (for example, swingable by about 90 degrees) between a lock release position (an unlocked position) as shown in FIG. 51 and a locked position for locking the door 3012 (a position shown in FIG. 52 and FIG. 54). The lock lever 3051 is integrally provided with a lock piece 3052. A lock latch 3053 is provided at an edge of the lock piece 3052. When the lock lever 3051 is manipulated to the locked position, the lock latch 3053 engages with the above-described engagement piece 3054 in the pump body 3011 (see FIG. 54), thereby keeping the door 3012 fully closed. The lock lever 3051, the lock piece 3052, and the lock latch 3053 in the door 3012, and the engagement piece 3054 in the pump body 3011 constitute a door lock mechanism 3005. The door lock mechanism 3005 can be located at the locked position or the unlocked position by manipulation of the lock lever 3051.

The door 3012 is further provided with a pressing plate 3024 at an inner face thereof. While the door 3012 is closed, the pressing plate 3024 faces a tip 21b of a particular finger 21 (the most-retracted finger 21) in the pump mechanism 2 at a certain interval Ga (see FIG. 60). The pressing plate 3024 is integrally formed with a rectangular detection object 3241. A detection object surface 3241a of the detection object 3241 is coplanar with a pressing surface (a front surface) of the pressing plate 3024. The position of the detection object 3241 corresponds to the position of a distance sensor 3006 disposed in the pump body 3011 (details to be described later). While the door 3012 is closed, the detection object surface 3241a of the detection object 3241 is opposed to a detecting surface 3006a of the distance sensor 3006 (see FIG. 54 and FIG. 60).

An infusion tube T connected to an infusion bag is set in the infusion pump 3001 of the above configuration in the following manner. Namely, a process of setting the infusion tube T includes: opening the door 3012; fitting the infusion tube T in the order of [upstream guide unit 3111a], [tube clamp 3112], [pump unit 3111b], and [downstream guide unit 3111c] to attach the infusion tube T; closing the door 3012 after the infusion tube is attached; and locking the door 3012 closed by the door lock mechanism 3005 to complete the setting operation. In this example, as described above, the tube clamp 3112 in the upstream guide unit 3111a is released while the door 3012 is closed. When the door 3012 is opened after the finish of infusion treatment or for other purposes, the tube clamp 3112 blocks the infusion tube T, thereby preventing free flow.

—Pump Mechanism—

Next, a specific example of the pump mechanism 2 applied to the infusion pump 3001 in this example is described with reference to FIG. 55 to FIG. 58. Among the elements illustrated in FIG. 55 to FIG. 58, the eccentric cams 22 are not shown in section.

The pump mechanism 2 is composed of a plurality of fingers 21 . . . 21 (13 fingers in the example shown in FIG. 54) aligned in one direction (a direction along the infusion tube T attached to the pump body 3011), eccentric cams 22 . . . 22 for independently advancing and retracting the fingers 21, a camshaft 23 for rotating the eccentric cams 22, a pressing plate 3024 mentioned above, a retention frame 20, and the like.

A front face of the retention frame 20 is provided with slots 20a . . . 20a which positionally correspond to the fingers 21. Tips of the fingers 21 are located at the front face side (the infusion tube T side) in the retention frame 20 and are configured to project through the slots 20a. Axial movements (movements in axial directions of the camshaft 23) of the fingers 21 . . . 21 are restricted by the retention frame 20. The fingers 21 are plate-like members which can move (advance and retract) independently while effecting sliding movements with respect to each other.

Each finger 21 has a cam hole 21a. A disc-shaped eccentric cam 22 is fitted in the cam hole 21a and is capable of rotating therein. The eccentric cams 22 . . . 22 are mounted on the camshaft 23 in an integrally rotatable manner.

Figure 56:
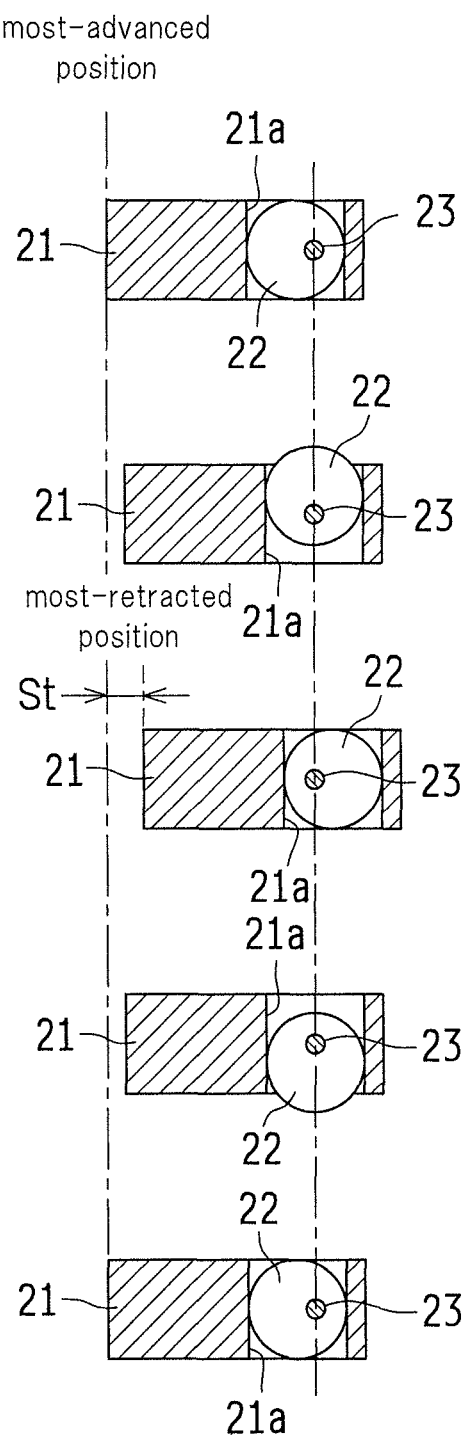
FIG. 56 illustrates a series of actions by a finger in the pump mechanism, wherein the finger is shown in section along a plane orthogonal to a camshaft.
Figure 58:
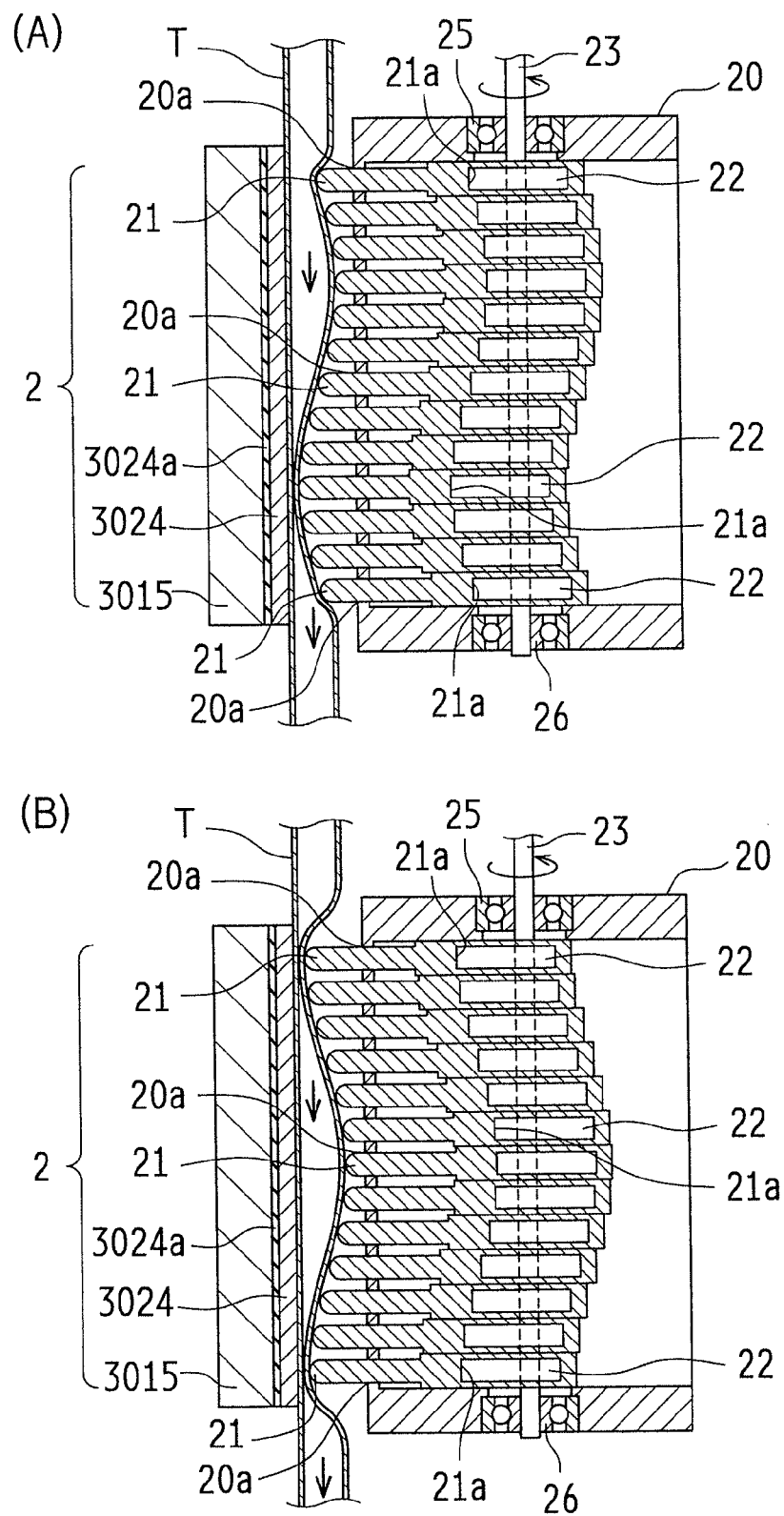
FIGS. 58(A) and 58(B) explain actions of the pump mechanism.

Each of the disc-shaped eccentric cams 22 has its center offset from the camshaft 23. As shown in FIG. 56, one rotation (360-degree rotation) of the camshaft 23 causes the tip of the finger 21 to effect one reciprocating motion between the most-advanced position (a tube block position) and the most-retracted position (a full tube release position). These eccentric cams 22 are mounted on the camshaft 23, with a predetermined phase difference from each other (a phase difference in a rotation direction of the camshaft 23). Specifically, the phase difference between the eccentric cams 22 . . . 22 mounted on the camshaft 23 is such that the tips of the fingers 21 . . . 21 aligned in the axial direction of the camshaft 23 form a substantially sinusoidal wave (Such a phase difference is obtained by dividing 360 degrees by the number of eccentric cams 22.). FIG. 56 shows the positions of a finger 21, with every 90-degree rotation of the camshaft 23.

Figure 55:
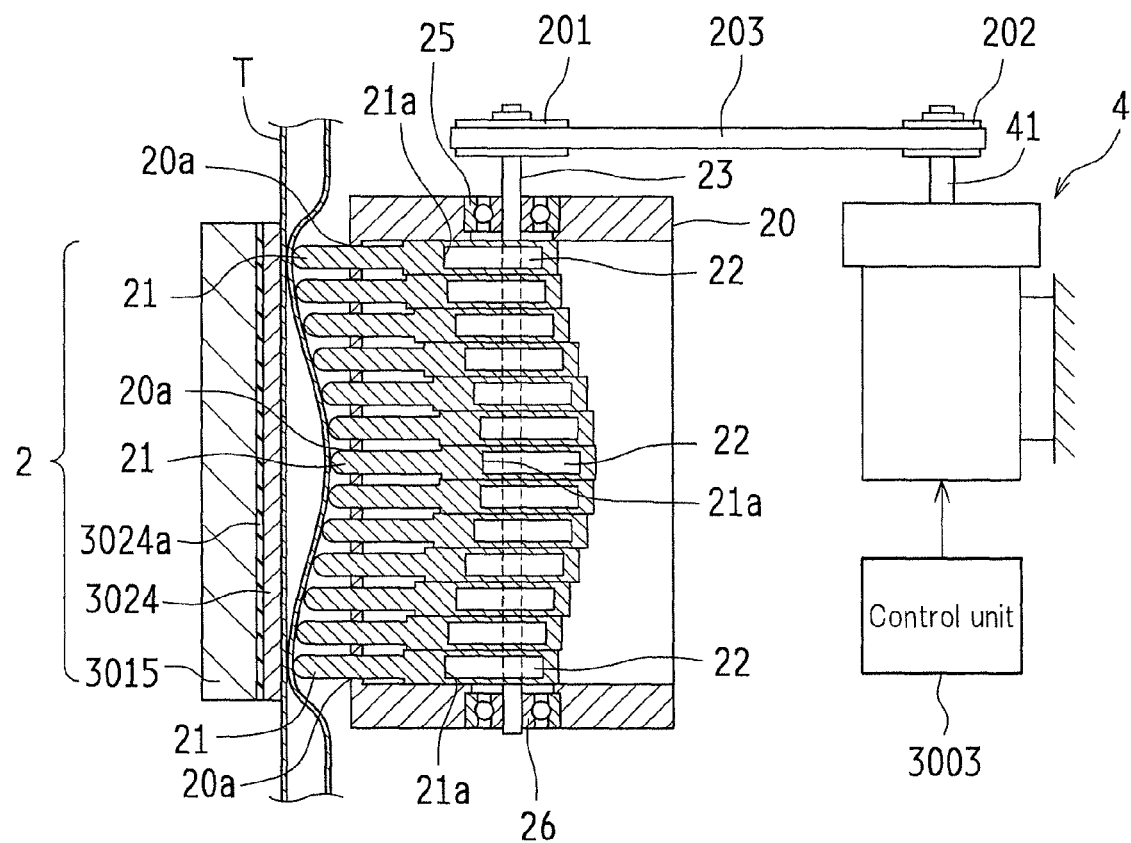
FIG. 55 shows a structure of a pump mechanism applied to the infusion pump.

As shown in FIG. 55, the camshaft 23 of the pump mechanism 2 is oriented vertically (in an alignment direction of the fingers 21 . . . 21). A lower end of the camshaft 23 is rotatably held by a bearing 26 provided in the retention frame 20. An upper part of the camshaft 23 penetrates upwardly through a wall of the retention frame 20. A penetration part of the camshaft 23 is provided with a bearing 25, which rotatably supports the upper part of the camshaft 23.

A timing pulley (an idler pulley) 201 is mounted at an upper end of the camshaft 23 in an integrally rotatable manner. A timing pulley (a drive pulley) 202 is mounted on a rotation shaft 41 of an electric motor (for example, a stepper motor) 4 in an integrally rotatable manner. A timing belt 203 is trained between the timing pulley 201 on the camshaft 23 and the timing pulley 202 on the rotation shaft 41. The camshaft 23 is driven to rotate by the electric motor 4. The drive (the number of revolutions) of the electric motor 4 is controlled by a control unit 3003. In this example, the electric motor 4 is powered by a battery built in the infusion pump 3001 or by a commercial power source.

When the camshaft 23 is driven to rotate by the electric motor 4, the eccentric cams 22 rotate in the cam holes 21a of the fingers 21. Along with the eccentric rotation of the eccentric cams 22, the fingers 21 advance and retract successively from upstream (upstream in the infusion liquid feed direction) to downstream. Specifically, as shown in FIGS. 57(A), 57(B) and FIGS. 58(A), 58(B), the tips of the fingers 21 move from upstream to downstream in a peristaltic wave-like pattern. Such advance and retraction (reciprocal movements) of the fingers 21 . . . 21 impart peristaltic movements to the infusion tube T positioned between the tips of the fingers 21 . . . 21 and the pressing plate 3024, thereby feeding infusion liquid in the infusion tube T from upstream to downstream. In this example, in order to alleviate an overload imposed on the infusion tube T by the fingers 21 . . . 21, a buffer sheet 3024a is provided between the pressing plate 3024 and a base plate 3015.

According to the infusion pump 3001 in this example, while the electric motor 4 is stopped, one or two of the fingers 21 . . . 21 in the pump mechanism 2 stay(s) at the most-advanced position (the full tube block position). While the door 3012 is closed, the one or two fingers 21 in the pump mechanism 2 block(s) the infusion tube T completely.

—Configuration of Control Unit, etc.—

Figure 59:
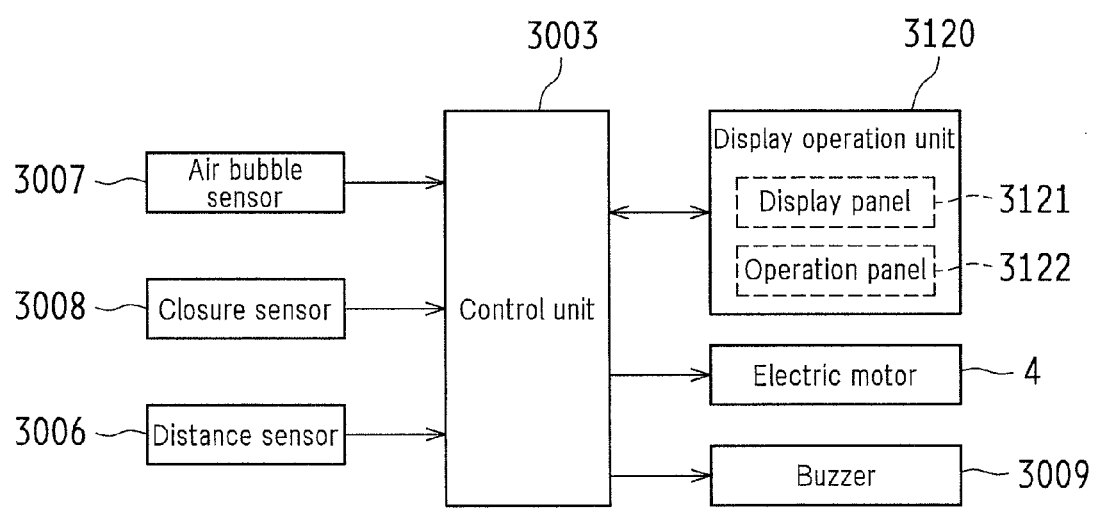
FIG. 59 is a diagram showing an example of a control system in the infusion pump.

The control unit 3003 is mainly configured by a microcomputer or the like. As shown in FIG. 59, the control unit 3003 is connected with an air bubble sensor (for example, an ultrasonic sensor) 3007 for detecting inclusion of air bubbles in the infusion tube T attached to the pump body 3011, a closure sensor 3008 for detecting whether the door 3012 is closed or some other condition, and a distance sensor 3006 to be described later. Output signals from these sensors are sent to the control unit 3003.

Figure 50:
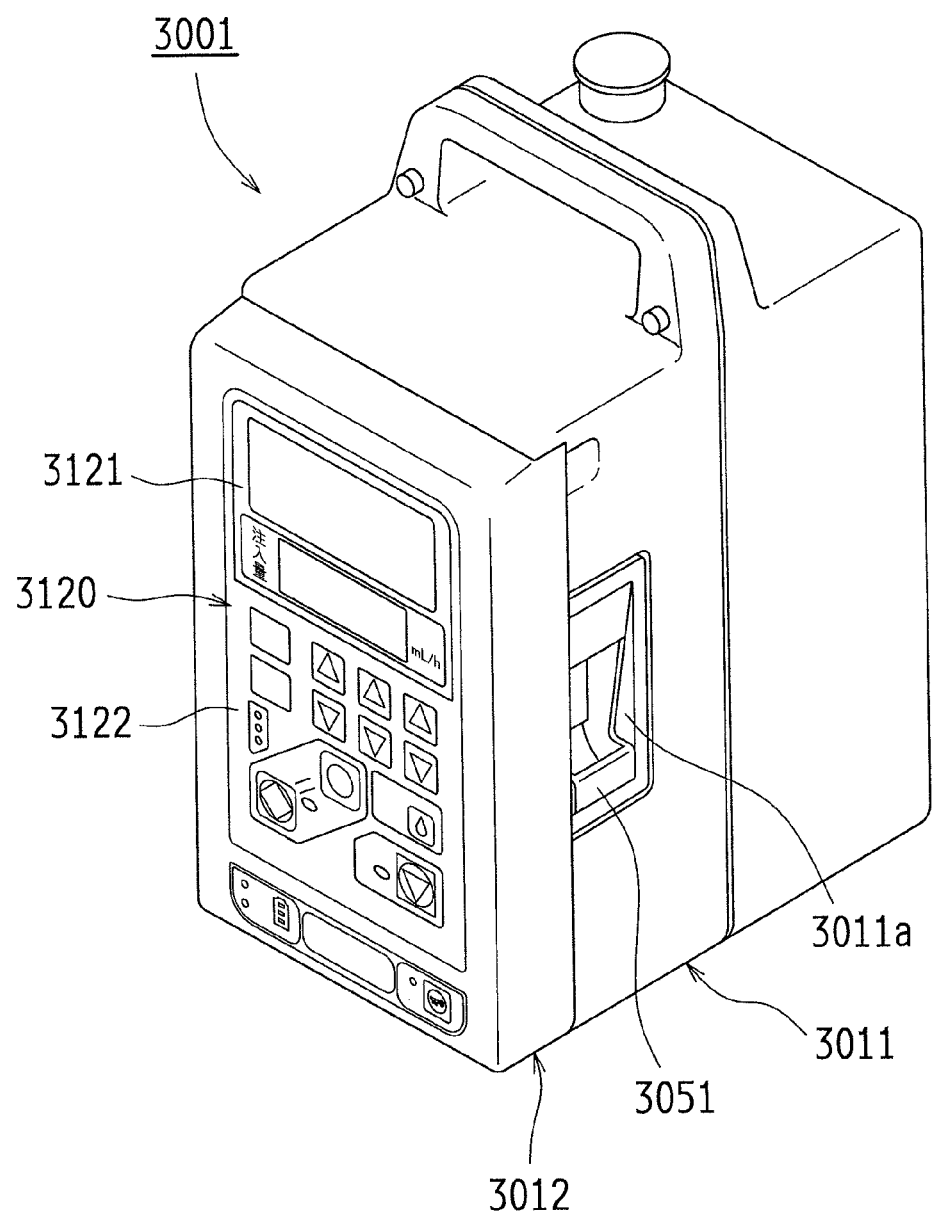
FIG. 50 is a perspective view showing an external appearance of still another exemplary infusion pump.

The control unit 3003 is further connected with the electric motor 4 for driving the pump mechanism 2 as mentioned above, a buzzer 3009, and a display operation unit 3120 provided at a front face of the door 3012 (see FIG. 50). The display operation unit 3120 is equipped with a display panel (a liquid crystal display) 3121 and an operation panel 3122.

The control unit 3003 can variably adjust the flow rate of the infusion liquid by controlling the number of revolutions of the electric motor 4 in the pump driving mechanism 2 based on a preset flow rate of the infusion liquid (an amount of feeding the infusion liquid per unit time) that is manually set (input) by an operation panel 3122 of the display operation unit 3120. In this example, the flow rate of the infusion liquid can be set, for instance, in a range between 1 mL/h and 1200 mL/h by an increment of [1 mL/h].

Additionally, the control unit 3003 displays operational information such as "flow rate of the infusion liquid (amount of infusion)" and "cumulative infusion time" on the display panel 3121 of the display operation unit 3120. The control unit 3003 further recognizes the length of air bubbles in the infusion tube T, based on an output signal of the air bubble sensor 7. If the length of an air bubble is greater than a predetermined value, the control unit 3003 displays an air-in-line warning on the display panel 3121 and simultaneously activates the buzzer 3009. Furthermore, the control unit 3003 displays information (for example, whether the door 3012 is securely closed) on the display panel 3121 based on an output signal of the closure sensor 3008.

Yet further, the control unit 3003 displays a message "abnormal flow rate" on the display panel 3121 and activates the buzzer 3009 by a process to be described below, based on an output signal of the distance sensor 3006.

—Features—

Features of the infusion pump 3001 in this example are hereinafter described.

Figure 60:
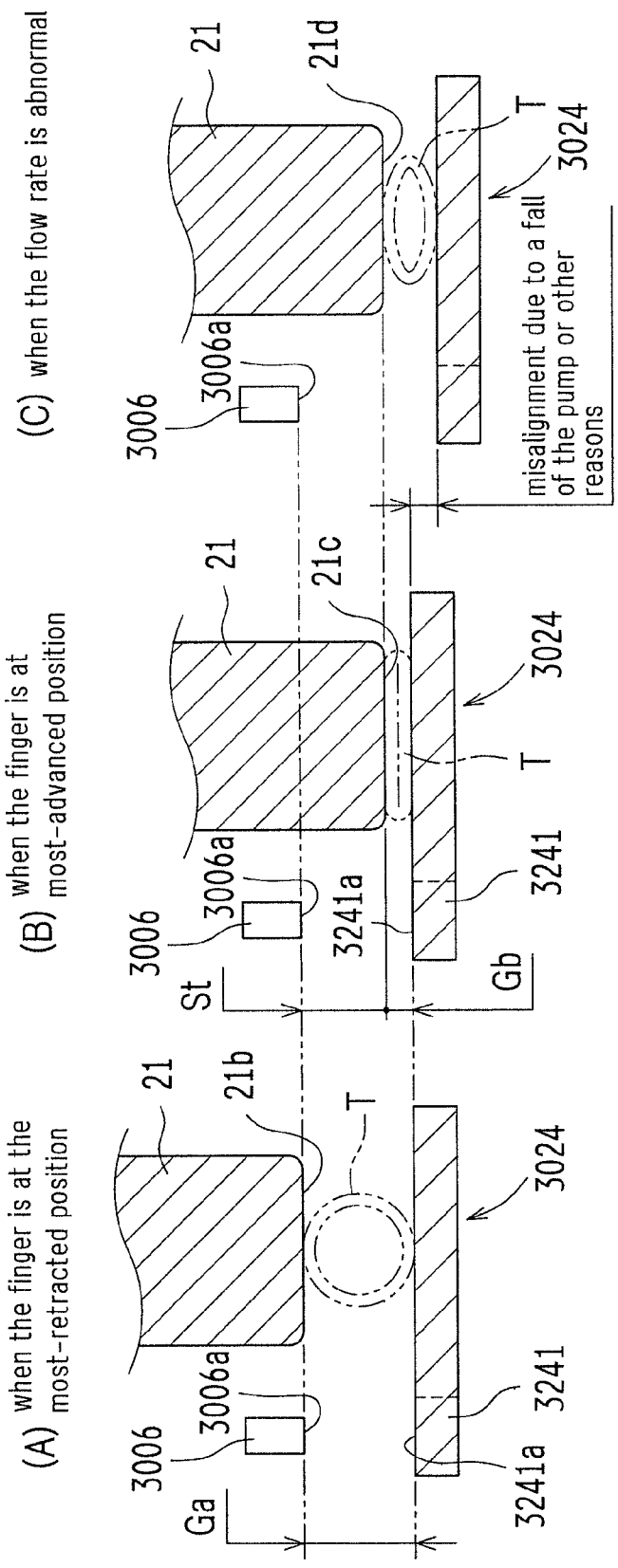
FIGS. 60(A), 60(B) and 60(C) illustrate positional relationships of a finger of the pump mechanism, a pressing plate, and a distance sensor, shown in section along a plane orthogonal to a camshaft of the pump mechanism.

In the finger infusion pump 3001, with a proviso that an infusion tube T is attached to the pump body 3011 and the door 3012 is closed, a gap Ga (see FIG. 60(A)) between a tip 21b of a most-retracted finger 21 (at the full tube release position) in the pump mechanism 2 and the pressing plate 3024 (the surface facing the fingers 21) provided on the door 3012 is designed to be the same as the diameter (the outer diameter) of the infusion tube T (when in an exact circle shape). Referring next to FIG. 60(B), a gap Gb between a tip 21b of the particular finger that has moved from the most-retracted position (the full tube release position) to the most-advanced position (the full tube block position) and the pressing plate 3024 is designed to be smaller by a predetermined value than twice the thickness t of the infusion tube T (Gb<2t). In FIG. 60 and FIG. 56, "St" means a stroke of a finger 21 moving from the most-retracted position to the most-advanced position.

In the infusion pump 3001 in this example, the door 3012 is swingably held by the pump body 3011 via hinges 3013, 3013. For example, if the infusion pump 3001 falls on the floor or somewhere else, the hinges may get loose due to the impact of fall. The hinges may also get loose if the door has been repeatedly opened and closed for a vast number of times due to long-term use or other reasons. Loose hinges may cause an increase in the gap between the tips 21b of the fingers 21 in the pump mechanism 2 and the pressing plate 3024 provided on the door 3012 while the door 3012 is closed (see FIG. 60(C)). If such an infusion pump is put into operation, the infusion tube T is not completely blocked by the finger 21 moving to the most-advanced position, which may result in free flow (free fall of infusion liquid) and a drastic increase in flow rate of the infusion liquid.

Further, in the case where the door 3012 has been deformed due to the impact of fall of an infusion pump or some other reasons, there may also be an increase in the gap between the tips 21*b* of the fingers 21 in the pump mechanism 2 and the pressing plate 3024 provided on the door 3012 while the door 3012 is closed. Similarly, if such an infusion pump is put into operation, the flow rate of the infusion liquid may increase drastically.

If a nurse or someone else overlooks an abnormal flow rate of the infusion liquid and continues infusion treatment, a prescribed amount of infusion liquid may not be administered to a patient (normal infusion treatment may be impossible).

In consideration of this risk, the infusion pump 3001 in this example is arranged to be capable of informing health-care professionals such as nurses if the flow rate of the infusion liquid is abnormal (has risen drastically) due to a fall of the infusion pump 3001 or some other reasons. A specific configuration fot this arrangement is described below.

Figure 54:
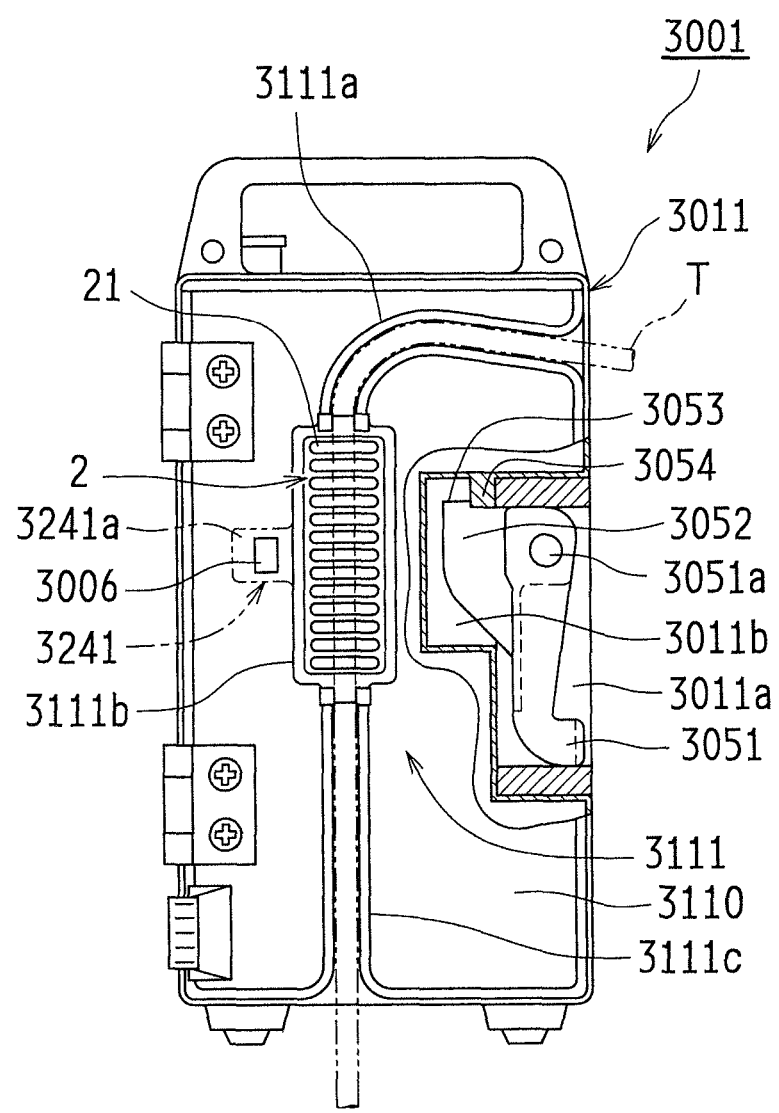
FIG. 54 is a schematic configuration of still another exemplary infusion pump, in a state where the door (omitted in this figure) of the infusion pump is closed.

In the infusion pump 3001 in this example, the pump body 3011 is equipped with a distance sensor 3006, as shown in FIG. 51, FIG. 54 and FIG. 60. The distance sensor 3006 is disposed near one side of the pump unit 3111*b*, at a vertically middle part (in the infusion liquid feed direction) relative to the pump unit 3111*b*.

The distance sensor 3006 is a reflective photoelectric sensor which detects a distance from a detecting surface 3006*a* to a detection object surface. The detecting surface 3006*a* of the distance sensor 3006 is in line with the tip 21*b* of the most-retracted finger 21 (at the full tube release position) in the pump mechanism 2, as shown in FIG. 60(A). Namely, the detecting surface 3006*a* of the distance sensor 3006 and the tip 21*b* of the most-retracted finger 21 are coplanar with each other and parallel to the front wall 110 of the pump body 3011 (see FIG. 51, etc.).

Also as described above, while the door 3012 is closed, the detecting surface 3006*a* of the distance sensor 3006 is opposed to the detection object surface 3241*a* of the pressing plate 3024 provided on the door 3012. In this opposed state, the distance sensor 3006 detects the gap (the distance) between the detecting surface 3006*a* of the distance sensor 3006 and the detection object surface 3241*a* of the pressing plate 3024, namely, the gap (Ga) between the tip 21*b* of the most-retracted finger 21 and the pressing plate 3024 provided on the door 3012 while the door 3012 is closed. An output signal from the distance sensor 3006 is sent to the control unit 3003.

Based on the output signal from the distance sensor 3006 while the door 3012 is closed, the control unit 3003 determines whether the gap between the detecting surface 3006*a* of the distance sensor 3006 and the detection object surface 3241*a* of the pressing plate 3024 (the gap between the tip 21*b* of the particular finger 21 and the pressing surface of the pressing plate 3024), is greater than a predetermined acceptable value Gath. If the gap detected by the distance sensor 3006 is greater than the acceptable value Gath, the control unit 3003 instructs the display operation unit 3120 shown in FIG. 50 and FIG. 49 to display a message "abnormal flow rate" on the display panel 3121, and activates the buzzer 3009, so that health-care professionals such as nurses can be informed of a failure.

In addition to the above manners of issuing a failure alarm, the control unit 3003 may also prohibit driving of the electric motor 4 in the pump mechanism 2 if, while the door 3012 is closed, the value detected by the distance sensor 3006 (the gap between the tip 21*b* of the particular finger 21 and the pressing surface of the pressing plate 3024) is greater than the acceptable value Gath.

The acceptable value Gath is set, for example, in the following manner. First, the gap (Gb: see FIG. 60) between the tip 21*b* of the most-advanced finger 21 (at the full tube block position) and the pressing surface of the pressing plate 3024 while the door 3012 is closed is taken as a parameter. Using this parameter, an upper limit $Gb_{LIM}$ of the gap (the gap between the tip of the particular finger and the pressing surface), at which free flow (due to a fall of the pump or other reasons) does not occur, is obtained by experiments, calculations, etc. Then, the acceptable value Gath is determined in accordance with the thus obtained upper limit. For example, the acceptable value Gath may be set as [Gath=St+$Gb_{LIM}$−margin]. In this formula, "St" means a stroke of a finger 21 moving from the most-retracted position to the most-advanced position (see FIG. 56 and FIG. 60).

As detailed above, while the door is closed, if the gap between the tip 21*b* of a particular finger and the pressing plate 3024 gets greater due to a fall of the infusion pump 3001 or some other reasons and, as a result, if the flow rate of the infusion liquid has drastically increased, the infusion pump 3001 in this example can inform health-care professionals such as nurses that the flow rate of the infusion liquid is abnormal. According to this configuration, it is possible to prevent infusion treatment under an abnormal flow rate of the infusion liquid, and to prevent overdose of infusion liquid to a patient.

—Modified Examples—

The above example employs one distance sensor 3006 (and the detection object surface 3241*a*). However, this is a non-limiting example, and the above example may employ two distance sensors 3006, one disposed at the upstream end and the other disposed at the downstream end relative to the pump unit 3111*b*. In this case, even if the door 3012 is inclined to the front wall 110 of the pump body 3011 due to the loose hinges 3013, the values detected by the two distance sensors 3006 ensure a correct judgement as to whether the gap between the tip of a particular finger 21 in the pump mechanism 2 and the pressing plate 3024 provided on the door 3012 is within a normal range (equal to or lower than the acceptable value) while the door 3012 is closed.

In the above example, the distance sensor is designed to detect the gap between the tip 21*b* of the most-retracted finger 21 and the pressing plate 3024 provided on the door 3012 while the door 3012 is closed. However, this is not a limitative example, and the distance sensor may be alternatively designed to detect a gap between the tip 21*b* of the most-advanced finger 21 and the pressing plate 3024 provided on the door 3012 while the door 3012 is closed. Also in this case, if the gap detected by the distance sensor is greater than the acceptable value ($Gb_{LIM}$−margin, as defined above), the control unit 3003 is arranged to instruct the display operation unit 3120 to display a message "abnormal flow rate" on the display panel 3121, and activates the buzzer 3009, so that health-care professionals such as nurses can be informed of a failure.

Incidentally, while the door 3012 is closed, the gap between the tip 21*b* of a particular finger 21 in the pump mechanism 2 and the pressing plate 3024 provided on the door 3012 is correlated with the gap between the front wall 110 of the pump body 3011 and the pressing plate 3024 provided on the door 3012. Therefore, the infusion pump may be also modified to detect the gap between the front wall 110 and the pressing plate 3024 by a distance sensor or the like, and to inform that the flow rate of the infusion liquid is abnormal, if the detected value is greater than the acceptable value.

In the above example, the distance sensor 3006 is a reflective photoelectric sensor. However, this is a non-limiting example, and the distance sensor may be of a different type such as a capacitance sensor and an ultrasonic sensor.

To issue a failure alarm, the above example uses the distance sensor 3006 and issues a flow rate failure alarm if the value detected by the distance sensor 3006 is greater than the acceptable value. For this purpose, the distance sensor 3006 may be replaced with a limit switch.

For example, a limit switch 3060 (not shown) may be provided at the position of the distance sensor 3006 shown in FIG. 51 and FIG. 54, ensuring that an actuator of the limit switch 3060 abuts the detection object 3241 of the pressing plate 3024 while the door 3012 is closed. The limit switch 3060 is configured to be turned off, if the gap between the tip of a particular finger 21 and the pressing plate 3024 provided on the door 3012 is equal to or lower than the acceptable value Gath. On the other hand, if the gap between the tip 21b of the particular finger 21 and the pressing plate 3024 exceeds the acceptable value Gath, the actuator of the limit switch 3060 is configured to leave a contact portion 241 of the pressing plate 3024 and to turn on the limit switch 3060. Also in this example, if the limit switch 3060 is in the ON state while the door 3012 is closed, the control unit 3003 instructs the display operation unit 3120 to display a message "abnormal flow rate" on the display panel 3121, and to activate the buzzer 3009, so that health-care professionals such as nurses can be informed of a failure.

Alternatively, the limit switch in this example may be turned off, if the gap between the tip 21b of the particular finger 21 in the pump mechanism 2 and the pressing plate 3024 provided on the door 21 exceeds the acceptable value while the door 3012 is closed.

[Configuration Example (2)]

Figure 61:
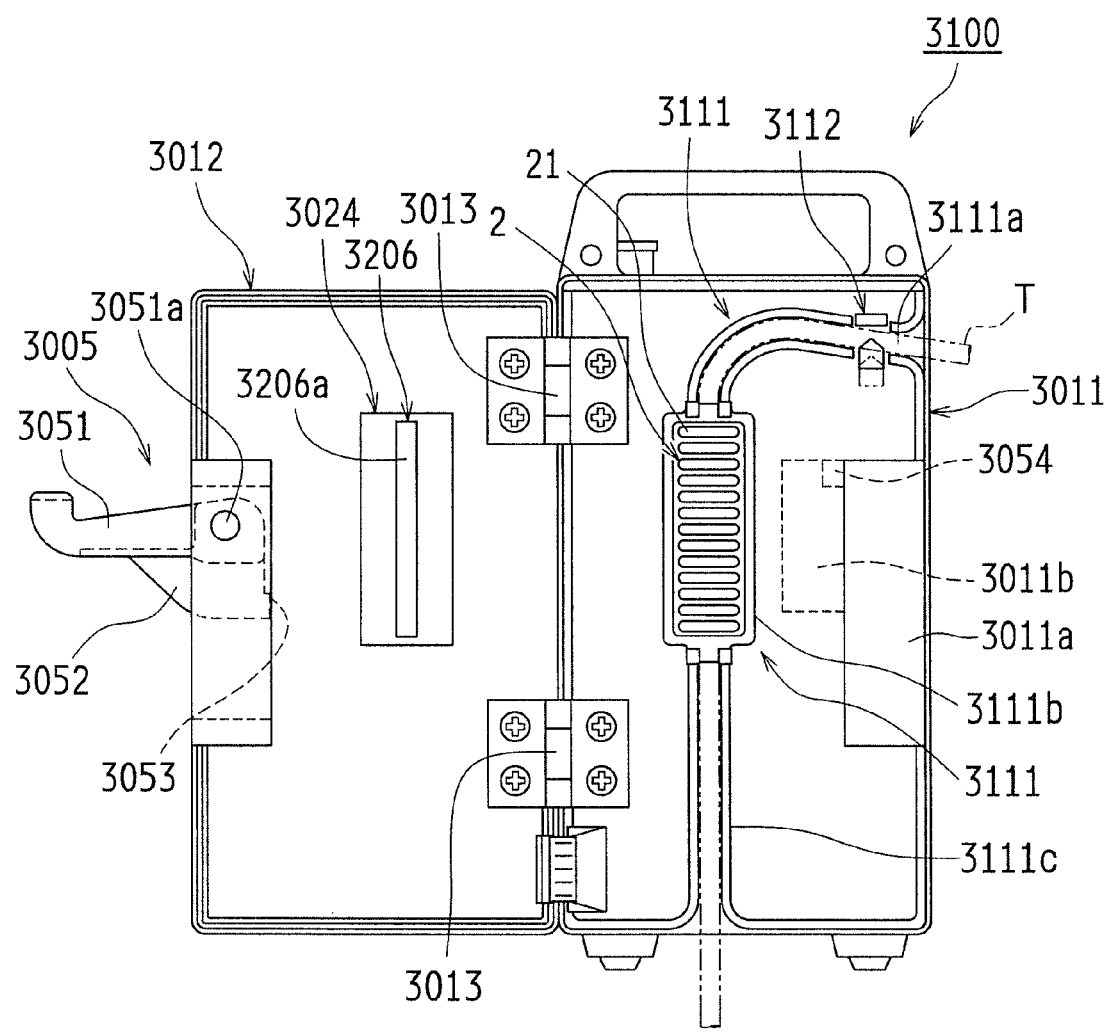
FIG. 61 shows a schematic configuration of a yet further exemplary infusion pump according to the present invention, in a state where the door of the infusion pump is open.

Referring to FIG. 61, another Configuration Example of the infusion pump is further described.

An infusion pump 3100 in this example is a peristaltic finger infusion pump, and is equipped with a pump body (a casing) 3011, and a door 3012 which closes on a front face (a tube attachment position) of the pump body 3011. The door 3012 is provided with a pressing plate 3024 in such a manner that the pressing plate 3024 faces a plurality of fingers 21 . . . 21 in the pump mechanism 2 while the door 3012 is closed.

Except the arrangements to be described below, the infusion pump 3100 in this example is similar to [Configuration Example (1)] described above, and hence detailed description of similar elements are omitted.

In the pressing plate 3024 provided on the door 3012, a pressure sensor 3206 is embedded. The pressure sensor 3206 is positioned to abut the infusion tube T attached to the pump unit 3111b of the pump body 3011 while the door 3012 is closed. Namely, the pressure sensor 3206 extends vertically (in a direction along the infusion tube T), approximately in a widthwise central part of the pressing plate 3024. A pressure-sensitive surface 3206a of the pressure sensor 3206 is coplanar with the pressing surface (the front surface) of the pressing plate 3024. An output signal from the pressure sensor 3206 is sent to the control unit 3003.

The pressure sensor 3206 may be, for example, a pressure sensor using a piezoelectric element, or a pressure sensor whose sensor portion is made of a pressure-sensitive conductive ink and which detects a change in a resistance value due to a load. Other types of pressure sensors are also applicable.

As described above, according to the infusion pump 3100 in this example, one (or two) of the fingers 21 . . . 21 in the pump mechanism 2 stay(s) at the most-advanced position (the full tube block position). Hence, after the infusion tube T is attached to the pump unit 3111b of the pump body 3011 and the door 3012 is closed, the one or two fingers 21 in the pump mechanism 2 block(s) the infusion tube T completely. While the infusion tube T is blocked completely, the pressing plate 3024 provided on the door 3012 receives a pressure from the infusion tube T.

In the infusion pump 3100 in this example, while the door 3012 is closed, if the gap Gb (see FIG. 60(B)) between the tip 21b of the most-advanced finger 21 and the pressing plate 3024 provided on the door 3012 is normal, the pressing plate 3024 receives a maximum pressure from the infusion tube T. On the other hand, while the door 3012 is closed, if the gap between the tip 21b of the most-advanced finger 21 in the pump mechanism 2 and the pressing plate 3024 increases due to the above-mentioned reasons (impact by a fall of the infusion pump 3100, or other reasons) (in the state shown in FIG. 60(C)), the pressing plate 3024 receives a less pressure.

Focusing attention on this regard, the infusion pump 3100 in this example is configured such that the pressure sensor 3206 detects a pressure applied to the pressing plate 3024 while the door 3012 is closed, and that an abnormal flow rate of the infusion liquid (a drastic increase in flow rate) is informed, based on the detected pressure (the pressure applied to the pressing plate 3024).

Specifically, the control unit 3003 determines whether the pressure applied to the pressing plate 3024 is smaller than a predetermined acceptable value Pth, based on an output signal from the pressure sensor 3206 while the door 3012 is closed. If the pressure applied to the pressing plate 3024 (the value detected by the pressure sensor 3206) is smaller than the acceptable value Pth, the control unit 3003 instructs the display operation unit 3120 to display a message "abnormal flow rate" on the display panel 3121, and activates the buzzer 3009, so that health-care professionals such as nurses can be informed of a failure.

The acceptable value Pth may be set, for example, in the following manner. First, with respect to the gap between the tip 21b of the most-advanced finger 21 (at the full tube block position) and the pressing plate 3024 while the door 3012 is closed, and with respect to the pressure applied by the infusion tube T to the pressing plate 3024 (a portion of the infusion tube T between one of the fingers 21 and the pressing plate 3024), the gap-pressure relationship is obtained by experiments, calculations, etc. Then, based on the gap-pressure relationship, a lower limit pressure $P_{LIM}$ (the pressure applied to the pressing plate 3024), which corresponds to the upper limit gap $Gb_{LIM}$ at which free flow does not occur as mentioned above, is obtained. Finally, the acceptable value Pth for the pressure applied to the pressing plate 3024 while the door 3012 is closed is determined in accordance with the thus obtained lower limit pressure $P_{LIM}$. For example, the acceptable value Pth may be set as [Pth=$P_{LIM}$+margin].

As detailed above, while the door is closed, if the gap between the tip 21b of a particular finger and the pressing plate 3024 gets greater due to a fall of the infusion pump 3100 or some other reasons and, as a result, if the flow rate of the infusion liquid has drastically increased, the infusion pump 3100 in this example can inform health-care professionals such as nurses that the flow rate of the infusion liquid is abnormal. According to this configuration, it is possible to prevent infusion treatment under an abnormal flow rate of the infusion liquid, and to prevent overdose of infusion liquid to a patient.

Also in this example, the control unit 3003 may prohibit driving of the electric motor 4 in the pump mechanism 2, if the pressure value detected by the pressure sensor 3206 while the door 3012 is closed is smaller than the acceptable value Pth.

In the above example, the pressure applied to the pressing plate 3024 is detected by the pressure sensor 3206 provided at the front face of the pressing plate 3024. However, the present invention should not be limited thereto, and the pressure applied to the pressing plate 3024 may be detected by a load sensor such as a strain gauge provided at the back face of the pressing plate 3024 or the like.

—Other Embodiments—

In the various examples described above, the pump mechanism in the infusion pump is, but should not be limited to, a peristaltic finger pump mechanism. As far as being capable of feeding infusion liquid in an infusion tube, other types of pump mechanism are also applicable. Specific examples include a roller pump mechanism, and a pump mechanism equipped with an organic actuator module in a V-shaped structure as disclosed in, for example, JP 2010-136853 A.

INDUSTRIAL APPLICABILITY

The present invention is applicable to infusion pumps employed for administration of a medical drug solution to a body or for similar treatment.

DESCRIPTION OF THE REFERENCE NUMERALS 1 infusion pump
11 pump body
112 pump unit
113 clamp holding recess
114 guide groove
117 clamp holding part
117a holding recess
12 door
123 clamp holding recess
13, 403 door lock mechanisms
131, 431 lock levers
131a, 431a rotation shafts
132, 432 lock pieces
133, 433 lock latches
134, 434 engagement pieces
435 gear
2 pump mechanism
3, 503 roller movement mechanisms
31, 531 roller sliders
31a, 531a block-side pushing pieces
31b, 531b release-side pushing pieces
321, 532 rack gears
322 pinion gear
323 electric motor (actuator)
323a rotation shaft
5 control unit
6 lock detection sensor
7 roller clamp
72 roller
72a, 72b rotation shafts
S infusion set
B infusion bag
T infusion tube
2001 infusion pump
2011 pump body
2011a lock recess
20110b through hole
112 pump unit
113 clamp holding part
2012 door
2012a roller through hole
2121 engagement member
2121a engagement hole
2123 operation recess
2005 door lock mechanism
2005A lock lever
2051 lock piece
2052 actuator
2053 fulcrum shaft
2054 lock spring (torsion coil spring)
2055 pin
2056 positioning member

The invention claimed is:

1. An infusion pump comprising a pump mechanism for pressing an infusion tube and feeding infusion liquid in the infusion tube in one direction, a pump body equipped with the pump mechanism, a door for covering an infusion tube attachment position in the pump body in a freely opening and closing manner, and a door lock mechanism for locking the door closed,
wherein the pump body comprises a clamp holding part for holding a roller clamp equipped with a roller, and a roller movement section that moves the roller of the roller clamp held by the clamp holding part, the roller clamp being configured to block or release the infusion tube in response to movement of the roller, and
wherein the roller movement section is configured to move the roller of the roller clamp in coordination with an operation for locking the door lock mechanism and to locate the roller of the roller clamp at a position for releasing the infusion tube when the door lock mechanism comes into a locked state, and is configured to move the roller of the roller clamp in coordination with an operation for unlocking the door lock mechanism and to locate the roller of the roller clamp at a position for blocking the infusion tube when the door lock mechanism comes into an unlocked state.

2. The infusion pump according to claim 1,
wherein the roller movement section comprises a movement mechanism that allows the roller of the roller clamp held by the clamp holding part to move between the infusion tube release position and the infusion tube block position, an actuator for activating the movement mechanism, a lock detection sensor for detecting whether the door lock mechanism is at a locked position, and a control unit,
wherein the control unit controls activation of the actuator based on a detection result by the lock detection sensor, and
wherein the control unit is configured to locate the roller of the roller clamp at the infusion tube release position when the door lock mechanism is at the locked position, and is configured to locate the roller of the roller clamp at the infusion tube block position when the door lock mechanism is not at the locked position.

3. The infusion pump according to claim 1,
wherein the door lock mechanism is configured to lock or unlock the door in response to turning manipulation of a lock lever,
wherein the roller movement section comprises a manipulation force transmission mechanism which converts a turning manipulation force of the lock lever into a force for moving the roller of the roller clamp held by the clamp holding part, and wherein the roller movement section is configured to locate the roller of the roller clamp at the infusion tube release position when the lock lever of the door lock mechanism is manipulated to a locked position, and to locate the roller of the roller clamp at the infusion tube block position when the lock lever of the door lock mechanism is manipulated to an unlocked position.

4. An infusion pump comprising a pump mechanism for pressing an infusion tube and feeding infusion liquid in the infusion tube in one direction, a pump body equipped with the pump mechanism, and a door for covering an infusion tube attachment position in the pump body in a freely opening and closing manner,
- wherein the pump body comprises a clamp holding part for holding a roller clamp equipped with a roller, the roller clamp being configured to block or release the infusion tube in response to movement of the roller,
- wherein the infusion pump is configured to expose a part of the roller of the roller clamp to an outside through an opening formed in the door, while the roller clamp is held by the clamp holding part and the door is closed,
- wherein the infusion pump further comprises a door lock mechanism for locking the door closed,
- wherein the door lock mechanism comprises a lock piece and an engagement member which are engageable with each other, and
- wherein the door lock mechanism is configured to allow the lock piece and the engagement member to be engaged with each other and thereby to lock the door closed, while the door is completely closed and the roller of the roller clamp held by the clamp holding part is located at a tube release position, and the door lock mechanism is also configured to allow the lock piece and the engagement member to be disengaged from each other and thereby to unlock the door, while the door is completely closed and the roller of the roller clamp held by the clamp holding part is located at a tube block position.

5. The infusion pump according to claim 4,
- wherein the door lock mechanism comprises a lock lever which is capable of turning around a fulcrum axis and which has the lock piece at an end of the lock lever, an actuator which is provided at another end of the lock lever and which is capable of contacting the roller of the roller clamp held by the clamp holding part, and a lock spring for biasing the lock lever to a locked position at which the lock piece and the engagement member are engaged with each other,
- wherein, while the actuator of the lock lever is free, the lock piece is located at the locked position at which the lock piece and the engagement member are engaged with each other by an elastic force of the lock spring, and
- wherein, while the door is closed and when the roller of the roller clamp held by the clamp holding part is manipulated to move to the tube block position, the actuator of the lock lever abuts the roller during the movement of the roller and is displaced against the elastic force of the lock spring, and the lock piece is located at an unlocked position.

* * * * *